US010496790B2

(12) United States Patent
Mark et al.

(10) Patent No.: US 10,496,790 B2
(45) Date of Patent: Dec. 3, 2019

(54) SYSTEM FOR DYNAMIC LOCATION-AWARE PATIENT CARE PROCESS CONTROLS

(71) Applicant: Mobile Heartbeat, LLC, Waltham, MA (US)

(72) Inventors: Jacob Mark, Boston, MA (US); Sajikumar Aravind, Burlington, MA (US); Michael Allen Kellstrand, Braintree, MA (US)

(73) Assignee: Mobile Heartbeat, LLC, Waltham, MA (US)

( * ) Notice: Subject to any disclaimer, the term of this patent is extended or adjusted under 35 U.S.C. 154(b) by 975 days.

(21) Appl. No.: 14/673,478

(22) Filed: Mar. 30, 2015

(65) Prior Publication Data

US 2016/0012196 A1 Jan. 14, 2016

Related U.S. Application Data

(60) Provisional application No. 61/971,887, filed on Mar. 28, 2014, provisional application No. 62/031,089, (Continued)

(51) Int. Cl.
*G06F 19/00* (2018.01)
*G06F 21/31* (2013.01)
(Continued)

(52) U.S. Cl.
CPC .......... *G06F 19/3418* (2013.01); *G06F 19/00* (2013.01); *G06F 21/31* (2013.01); (Continued)

(58) Field of Classification Search
None
See application file for complete search history.

(56) References Cited

U.S. PATENT DOCUMENTS 7,603,112 B2   10/2009 Huomo et al.
8,041,581 B2   10/2011 Mitchel et al.
(Continued)

FOREIGN PATENT DOCUMENTS

WO      2015/149073 A1    10/2015

OTHER PUBLICATIONS

International Preliminary Report on Patentability of PCT/US2015/023389 dated Jun. 16, 2016, all pages.
(Continued)

*Primary Examiner* — Devin C Hein
(74) *Attorney, Agent, or Firm* — Kilpatrick Townsend & Stockton LLP

(57) ABSTRACT

A system having a system backend having a backend processor configured to define a patient clinical team associated with a patient clinical process comprising of a series of patient clinical tasks effected within the healthcare facility, each patient clinical task with an associated patient clinical task location within the healthcare facility, a group of mobile devices communicably connected via a network to the system backend, each mobile device being associated with and configured for use by at least one care member of the patient clinical team, a low energy (LE) beacon array arranged in a predetermined relationship with and differentiating between different patient clinical task locations, and communicably connected to each of the mobile devices that is configured to resolve its proximity, from the beacon array, relative to the at least one patient clinical task location. The backend processor is configured to dynamically enhance the patient clinical team by dynamically changing in real-time a predetermined characteristic of the patient clinical team based on the resolved proximity of each mobile device associated with each care member of the patient clinical team.

38 Claims, 25 Drawing Sheets

Related U.S. Application Data filed on Jul. 30, 2014, provisional application No. 62/032,172, filed on Aug. 1, 2014.

(51) Int. Cl.

| | | |
|---|---|---|
| *G06F 21/44* | (2013.01) | |
| *G06Q 10/00* | (2012.01) | |
| *G16H 40/20* | (2018.01) | |
| *G06Q 50/22* | (2018.01) | |

(52) U.S. Cl.
CPC ............. *G06F 21/44* (2013.01); *G06Q 10/00* (2013.01); *G06Q 50/22* (2013.01); *G16H 40/20* (2018.01); *G06F 2221/2111* (2013.01)

(56) References Cited

U.S. PATENT DOCUMENTS

| | | | |
|---|---|---|---|
| 8,041,583 | B2 | 10/2011 | Albro et al. |
| 8,060,492 | B2 | 11/2011 | Nair et al. |
| 8,229,358 | B2 | 7/2012 | Caudevilla Laliena et al. |
| 8,254,902 | B2 | 8/2012 | Bell et al. |
| 8,326,651 | B2 | 12/2012 | McLaren et al. |
| 8,355,672 | B2 | 1/2013 | Hinsey |
| 8,359,643 | B2 | 1/2013 | Low et al. |
| 8,428,614 | B2 | 4/2013 | Wolfe |
| 8,516,075 | B2 | 8/2013 | Seetharam et al. |
| 8,583,560 | B1 | 11/2013 | Burger |
| 8,615,413 | B2 | 12/2013 | McKee et al. |
| 8,656,060 | B2 | 2/2014 | Kyriazis et al. |
| 9,058,410 | B2 | 6/2015 | McKee et al. |
| 2003/0137455 | A1 | 7/2003 | McReynolds |
| 2004/0100377 | A1 | 5/2004 | Brackett |
| 2005/0136845 | A1* | 6/2005 | Masuoka .............. G01S 5/0294 455/67.14 |
| 2007/0184852 | A1 | 8/2007 | Johnson et al. |
| 2009/0132586 | A1* | 5/2009 | Napora .................. G16H 40/20 |
| 2010/0305972 | A1 | 12/2010 | McLaren et al. |
| 2011/0106565 | A1* | 5/2011 | Compton .............. G06Q 50/22 705/3 |
| 2012/0042039 | A1* | 2/2012 | Mark .................... G06F 19/327 709/217 |
| 2012/0095779 | A1* | 4/2012 | Wengrovitz ........... G16H 40/20 705/3 |
| 2012/0290311 | A1 | 11/2012 | Tara |
| 2013/0074171 | A1 | 3/2013 | Mark |
| 2014/0330945 | A1* | 11/2014 | Dabbiere ............ H04L 41/0843 709/220 |
| 2015/0248230 | A1 | 9/2015 | Mark |

OTHER PUBLICATIONS

U.S. Appl. No. 61/939,104, filed Feb. 12, 2014, all pages.

International Search Report, International Application No. PCT/US2015/023389, dated Aug. 28, 2015.

Office Action dated Feb. 28, 2019 in related foreign European application No. EP 15769644.4, 5 pgs.

* cited by examiner

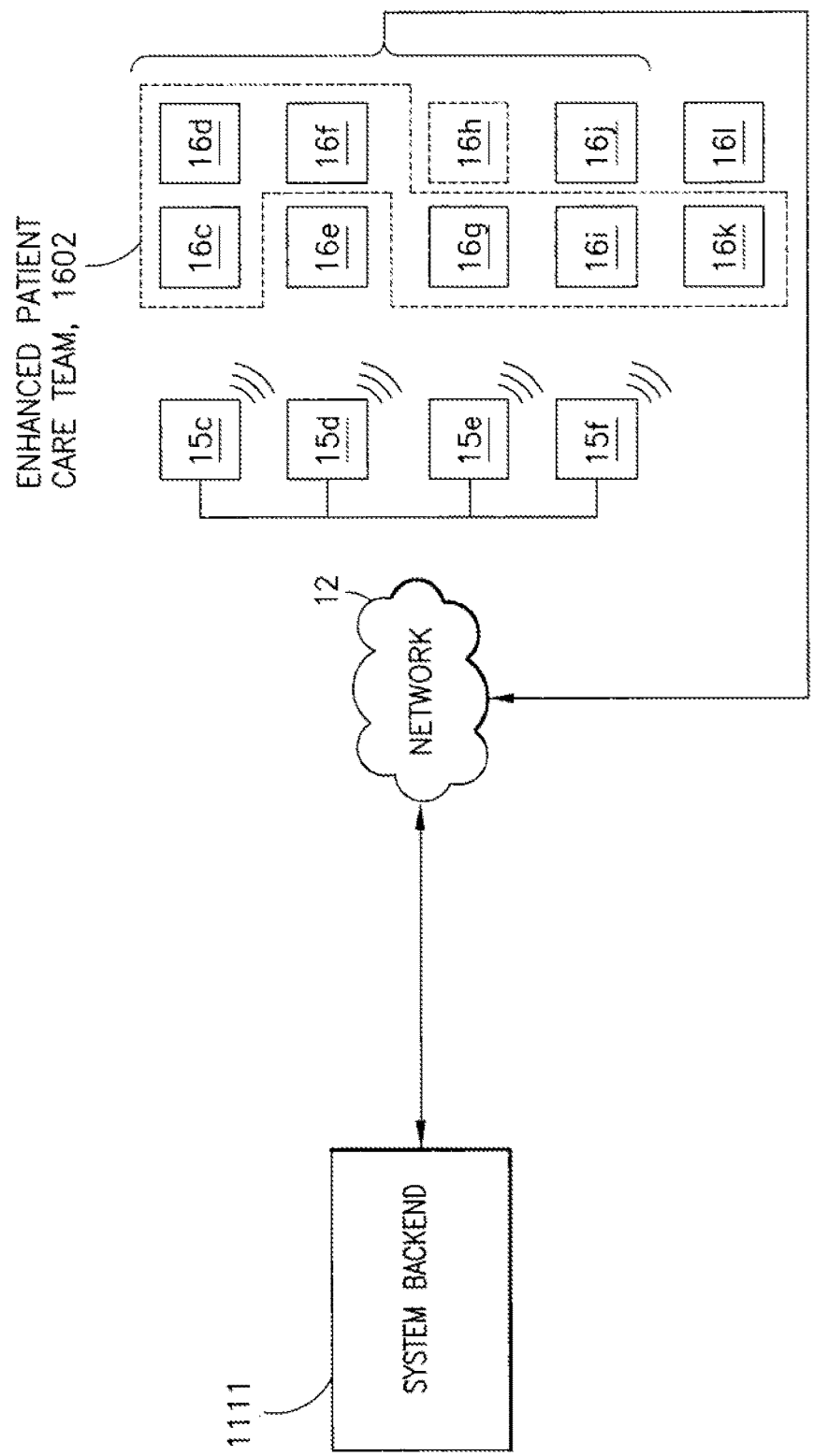

SYSTEM FOR DYNAMIC LOCATION-AWARE PATIENT CARE PROCESS CONTROLS

RELATED APPLICATIONS

This application is the nonprovisional of U.S. Provisional Patent Application No. 61/971,887 filed Mar. 28, 2014, U.S. Provisional Patent Application No. 62/031,089, filed Jul. 30, 2014, and U.S. Provisional Application No. 62/032,172, filed Aug. 1, 2014, the disclosures of which are incorporated herein by reference in their entirety.

BACKGROUND

1. Field

The aspects of the exemplary embodiment generally relate to controlling an aspect of clinical process by using location-based data correlated with clinical tasks of a clinical process.

2. Brief Description of Related Developments

The current method of controlling a patient care team involves manually setting up and controlling patient care teams. The current methods, however, may be supplemented or improved by location-aware methods dynamically enhance patient care teams. Location-aware methods may also be leveraged to dynamically track patient care assets.

BRIEF DESCRIPTION OF THE DRAWINGS

The foregoing aspects and other features of the disclosed embodiments are explained in the following description, taken in connection with the accompanying drawings, wherein:

FIGS. 16A-B illustrates a schematic representation of an overview of the system for dynamically enhancing a patient care team.

DETAILED DESCRIPTION OF THE EMBODIMENT(S)

Although the aspects of the disclosed embodiment will be described with reference to the drawings, it should be understood that the aspects of the disclosed embodiment can be embodied in many alternate forms. In addition, any suitable size, shape or type of elements or materials could be used.

Although the aspects of the exemplary embodiment will be described in the context of a in a medical, hospital or clinical context it should be noted that the disclosed embodiment encompasses any situation where a physical process is used to control physical tasks. This may include, for instance, warehouse, retail, factory, offices or any other situations where multiple workers or project-workers may be working concurrently on a series of physical tasks to complete a common objective. For clarity and simplicity purposes, physical process pathways are also referred to as clinical processes within this application and pertain to a clinical or hospital context. Similarly, physical tasks are referred to as clinical tasks within this application and also pertain to a clinical or hospital context.

Figure 1:
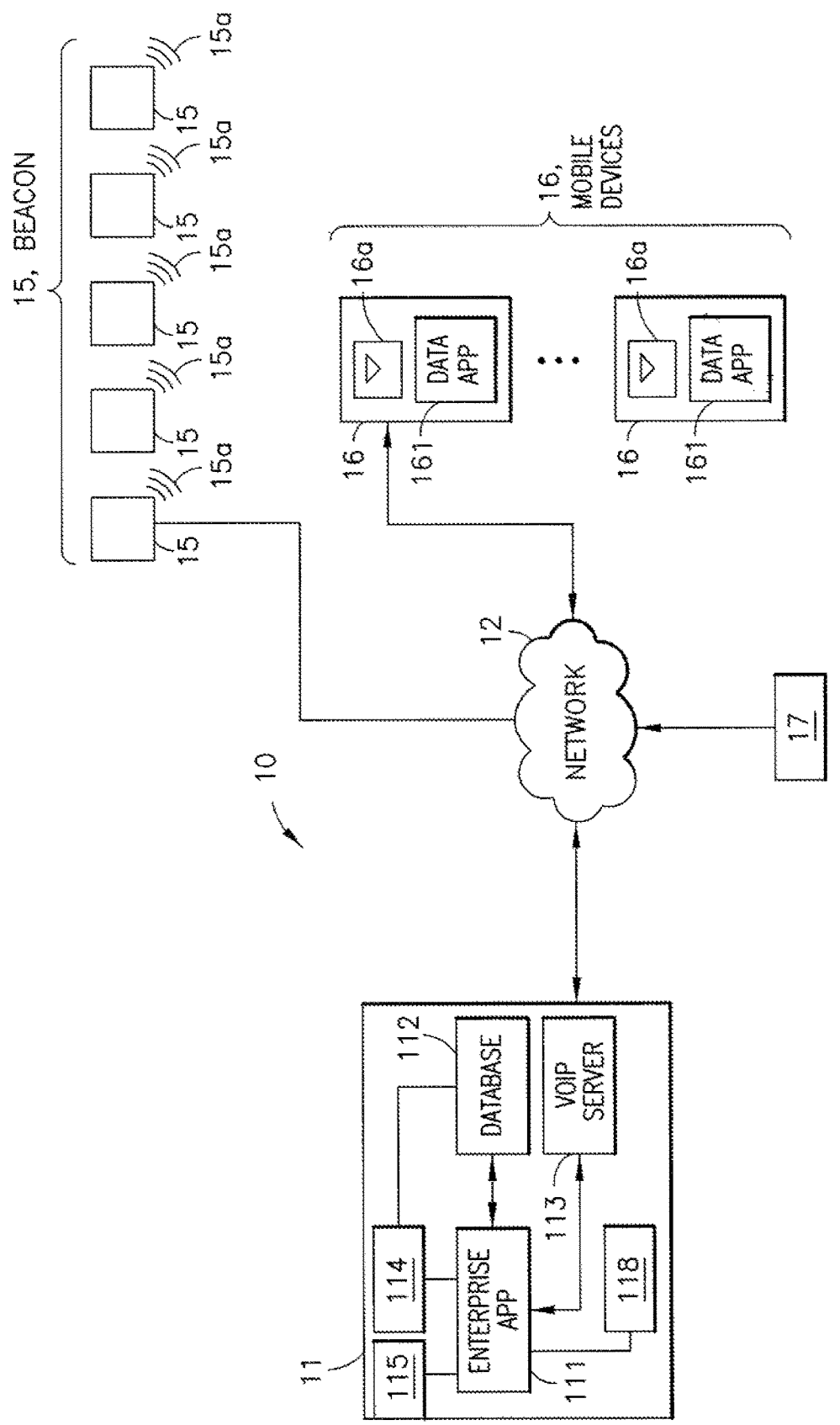
FIG. 1 illustrates a schematic representation illustrating an overview of the system for controlling an aspect of clinical process by using location-based data.

FIG. 1 illustrates an exemplary schematic diagram illustrating the system. Although the present invention will be described with reference to the embodiment shown in the drawings, it should be understood that the present exemplary embodiments can be used individually or in any suitable combination thereof. Although the aspects of the disclosed embodiment will be described with reference to the drawings, it should be understood that the aspects of the disclosed embodiment can be embodied in many alternate forms. In addition, any suitable size, shape or type of elements or materials could be used.

Referring to FIG. 1, a system backend 11 is depicted. In one aspect of the disclosed embodiment, the system backend 11 is in the form of a general purpose computer system or server system. In alternate aspects of the disclosed embodiment, the system backend 11 can also be multiple computers or servers or any other suitable device. In another aspect of the disclosed embodiment, the system backend 11 may be a cloud service provider where processing may be performed by means of a distributed computing system wherein the system backend is operating on many servers or computers concurrently or in parallel. In other aspects of the disclosed embodiment, the system backend 11 is virtual hardware, for example, a virtual server running within a cloud service provider running the system backend 11. The system backend 11 further comprise a mobile device management server 114. The mobile device management server 114 is a module which is configured to manage and control the functionalities of a mobile device remotely according to a predetermined system of rules or criteria. The mobile device management server 114 may be configured to limit access to certain functionalities of a mobile device that may be in communication with the system backend 11 but also provide other functionalities such as but not limited to providing different user interface features and/or enabling applications as will be described further below. The mobile device management server 114 which can also activate "log-in" functionalities, i.e. turning on a Mobile Heartbeat app, which was described in the Workflow and Resource Management System with Integrated Bi-Directional Communications as described in U.S. patent application Ser. No. 13/027,158, filed on Feb. 14, 2011, which was previously incorporated by reference in its entirety. Furthermore, backend 11 can communicate over a network 12 with mobile devices 16 that also communicate over network 12. In one embodiment, the network 12 is a wireless network. The wireless network may be an 802.11 network, but may also be Bluetooth, Bluetooth LE, GSM, RF or any other suitable form of network. In another embodiment, the network 12 is a wired network. Through the network 12, the backend 11 is able to enable a variety of data communication technology, for example, but not limited to voice-over-IP, video-over-IP, text messaging, public switched telephone networks, or any other form of bi-directional communication. This may take the form of, for example, a voice over IP telephony server 113. The backend may also run an enterprise application 111 within a server environment or a cloud environment. The enterprise application 111 is implemented using a computer code comprising instructions that may be executed by a processor or multiple processors within the backend 11. The code may be embodied in a computer-readable medium such as a magnetic or optical disk, programmable memory chip, or any other non-transitory computer-readable medium. The enterprise application may communicate with a database 112 and access and update the information within the database. The database 112 may be a login database comprising a database containing information pertaining to user logins, personalized settings and data, and any other suitable credential information. The enterprise application 111 acts as the controller for the workplace and resource system. The login database may be used as part of an automated login system, for example, the one described in Automated Login Initialization On Detection of Identifying Information (hereinafter "Quick Launch") as described in U.S. patent application Ser. No. 13/616,483 filed on Sep. 14, 2012, the disclosure of which is incorporated by reference herein in its entirety. The enterprise application 111 acts as a controller for the clinical process control and presentation system. The server environment upon which the enterprise application 111 runs may take the form of, for example, Java servlets, or any other suitable environment upon which an enterprise application may execute. Login management application 114 may also be on the backend 11 to manage users and device logins. In accordance to an embodiment, the system backend 11 may be configured for any sort of suitable reasonable use and may not be dedicated specifically for login procedures.

The system backend 11 is configured to manage a clinical process that comprises a series of clinical tasks for the care of a common patient which have a predetermined end. Each of the clinical tasks of the clinical process is associated with a clinical task location and each of the clinical task locations for a physical task is different from the clinical task locations of another physical task. The system backend 11 maintains a clinical process directory representing a list of patients or a list of clinical processes. The clinical process directory is comprised of a number of selectable elements which may be represented and interacted with on a mobile device 16 (to be described in greater detail below). Each of the clinical tasks in the series of clinical tasks for a clinical process corresponds to different selectable elements within the clinical process directory so that each selectable element represents a different clinical task and its associated clinical task location.

Referring still to FIG. 1, an array of low energy (LE) beacons (also referred to as "Beacons") 15 is shown. The array of Beacons may be arranged in a predetermined relationship that may allow for differentiating between different physical locations. For the purposes of this application, references to location may also refer to the proximity of a predetermined point such as within the proximity of a low energy beacon 15. It should be noted that the beacons 15 may substantially correspond to the beacons described in the "SYSTEM FOR LOCATION-AWARE CONTROL OF PROCESS PATHWAYS" as described in U.S. Provisional Patent Application No. 61/971,887, filed on Mar. 28, 2014, U.S. Provisional Patent Application No. 62/031,089, filed Jul. 30, 2014, and U.S. Provisional Application No. 62/032,172, filed Aug. 1, 2014, which were previously incorporated by reference in their entirety. In one aspect of the disclosed embodiment, each Beacon 15 represents a physical location within an array space. The Beacons 15 allows for objects to resolve, roughly, where they are relative to an array space by resolving which Beacons 15 they are in proximity with. In other aspects, the Beacons 15 may also allow for objects to resolve where they are relative to a space by resolving Beacons 15 that they are in proximity with as well as measuring the changes in proximity to various Beacons 15 to determine relative movements of the object. In the clinical context of a hospital or healthcare facility, a Beacon 15 is placed in every hospital room, every ward and every surgical room. However, in other contexts, a Beacon 15 may be placed anywhere near a physical location to represent that physical location—for instance, different storage racks in a storage warehouse or departments within a retail store or any other suitable example. In other words, the Beacons 15 may be placed such that they are in an arrangement with some locational relationship relative to each other and subdivides locations into sublocations by which localization may be determined. In alternate aspects, there may be a grid overlay on the floor plan of a location with a Beacon 15 placed within the overlay grid at regular intervals. Each Beacon 15 may have a Beacon transceiver 15A which may each broadcast a Beacon signal which identifies each particular beacon. In one aspect of the disclosed embodiment, the Beacon transceiver 15a may transmit via Bluetooth® Low Energy (BLE). However, in alternate aspects, any suitable form of beacon may be used. For instance, a Beacon 15 may transmit simple RF signals, or may be RFID based, NFC, a Wi-Fi signaling device or any other suitable means of broadcasting a Beacon 15 signal. In yet other aspects, more exotic means of Beacon 15 signals may be used, for instance, infrared or visible light beacons.

It should be further noted that, in one aspect of the disclosed embodiment, the array of Beacons 15 are arranged in such away with overlapping zones between the Beacons 15 and between arrays. For instance, a mobile device 16 may detect more than one low energy beacon signal, especially in a densely situated location. For instance, on a hospital floor, the beacon signals may bleed through the floors or through the walls. In a locale with many beacons, a mobile device 16 may also be within the proximity of a multiple of beacons. However, the mobile device 16 may be able to detect each of the beacon signals and discriminate or resolve which beacon it is closest in proximity based on the beacon signals received by the mobile device 16. It should be also noted that, in one aspect of the disclosed embodiment, the low energy beacon 15 arrays is distributed separately, one on each floor. For instance, one set of array may be for a first floor and a second set of the low energy beacon array may be arranged on the second floor. This is possible where the location is divided up into different locations such as wards. There may be an issue of bleed through where beacon signals from different arrays are detected by a mobile device. In such situations, it may be possible for a mobile device to discriminate which beacon is the proper beacon to use for proximity purposes based on which distinct array the mobile device 16 is assigned or associated with. For instance, a nurse assigned to work only on a particular floor or wing may have a mobile device 16 which may only use the low energy beacon signals from the array on the floor assigned to them and disregard signals from other floors or other wards detectable because of bleed through.

Referring still to FIG. 1, a number of fungible mobile devices 16 may communicate over the network 12. As described previously, the network 12 may be a wireless network in some embodiments. The wireless network may be an 802.11 network, but may also be Bluetooth, WiMAX, BLE, RF, GSM or any other suitable form of network. In other embodiments, the network 12 may also be a wired network. In one aspect of the disclosed embodiments, the mobile devices 16 may be generally fungible devices as previously noted, that is, one mobile device 16 may be interchangeable with any other mobile device 16. Thus, mobile device 16 may store no personalized settings or data desirable for operation, instead relying on data received from the system backend 11 by means of a device data application 161. However, in other aspects of the disclosed embodiment, the mobile device 16 may be unique to the user, but configured so that functionalities available within the system are locked or blocked when no longer logged in. The availability of the functionalities of the mobile device 16 based on the state of the mobile device 16 (e.g. whether the mobile device 16 is logged in or not) is described in greater detail the system described in SYSTEM FOR SETTING AND CONTROLLING FUNCTIONALITIES OF MOBILE DEVICES as described in U.S. Provisional Patent Application 61/939,104 filed on Feb. 12, 2014, and Nonprovisional U.S. application Ser. No. 14/621,281, filed Feb. 12, 2015, the disclosures of which are incorporated by reference herein in their entireties. The mobile device 16 has a mobile device processor. In one aspect of the disclosed embodiment, the mobile device processor is a CPU or System on a Chip (SOC), but in alternate aspects, the mobile device processor may be any suitable processor. The mobile processor may be used to execute a data application 161. The data application 161 may communicate with backend 11 through the data module 116, for example via Web Services such as SOAP protocols, or any other suitable communications protocols and may be capable of accessing and updating data stored within the database 112, possibly through the login manager 114. The device data application 162 may take the form of a native application designed to run as computer code executed by mobile device 16. The computer code may be embodied in a computer-readable medium stored on mobile device 16 such as magnetic or optical disk, programmable computer chip or any other non-transitory computer-readable medium. In other embodiments, the device data application 161 may also take the form of a non-native application, for example, a Java-based application running on a virtual machine or a web-based application such as an HTML5 application. In other aspects of the disclosed embodiment, the mobile devices 16 may also be in the form of Personal Digital Assistants (PDAs), computer terminals, or any other suitable device capable of running the device data application 166 described above. Other devices may also be able to communicate with backend 11 through the network 12 as described above.

Each of the mobile devices 16 may further have a beacon signal receiver 16a. The beacon signal receiver 16a may be used to receive a Beacon signal from a Beacon transceiver 15a and may be in communication with the Beacon transceiver 15a. The mobile device 16 may further receive the Beacon signal and allow the mobile device 16 to resolve the mobile device 16's proximity based on the beacon signal received from the array of Beacons 15 and to correlate the mobile device 16's proximity with a physical task location. The mobile device 16 may then signal the mobile device 16 proximity to the system backend 11. The beacon signal receiver 16a may receive Bluetooth® Low Energy (BLE) signals. However, in alternate aspects, any suitable form of beacon signal may be received. For instance, the beacon signal receiver 16a may receive simple RF signals, or may be RFID based, NFC, a Wi-Fi signaling device or any other suitable means of receiving a Beacon signal. The beacon signal receiver 16a may also receive more exotic means of signaling, including with infrared or visible light signals.

It is noted that each of the mobile devices 16 may have a different predetermined characteristic relating to effecting at least one of the clinical tasks of a clinical process and altering the state of a corresponding clinical process. The predetermined characteristic may include, for instance, the functional groups or the user that the mobile device 16 is associated with (e.g. in the system backend 11). The functional groups or user permissions may be similar to those described in, for example, the one described in SYSTEM FOR SETTING AND CONTROLLING FUNCTIONALITIES OF MOBILE DEVICES as described in U.S. Provisional Patent Application 61/939,104 filed on Feb. 12, 2014, and U.S. application Ser. No. 14/621,281, filed Feb. 12, 2015, the disclosures of which were previously incorporated by reference in their entirety. Referring still to FIG. 1, the system backend 11 may further have a location-based module 118. The system backend 11 may use the location-based module 118 to register a device proximity signaled from the mobile device 16 (which the mobile device 16 resolved from the signals received from the Beacon transceiver 15a with the beacon signal receiver 16a). The system backend 11 may correlate the mobile device proximity with the location of a clinical task of a clinical process generated by the system backend 11. The system backend 11 may further be configured to initiate a predetermined action associated with the state of a clinical task based on the mobile device proximity. The system backend 11 may further be configured to determine whether a mobile device 16 is available to receive a communication related to a corresponding clinical task based on the proximity resolved by the mobile device with respect to the clinical task.

Figure 1A:
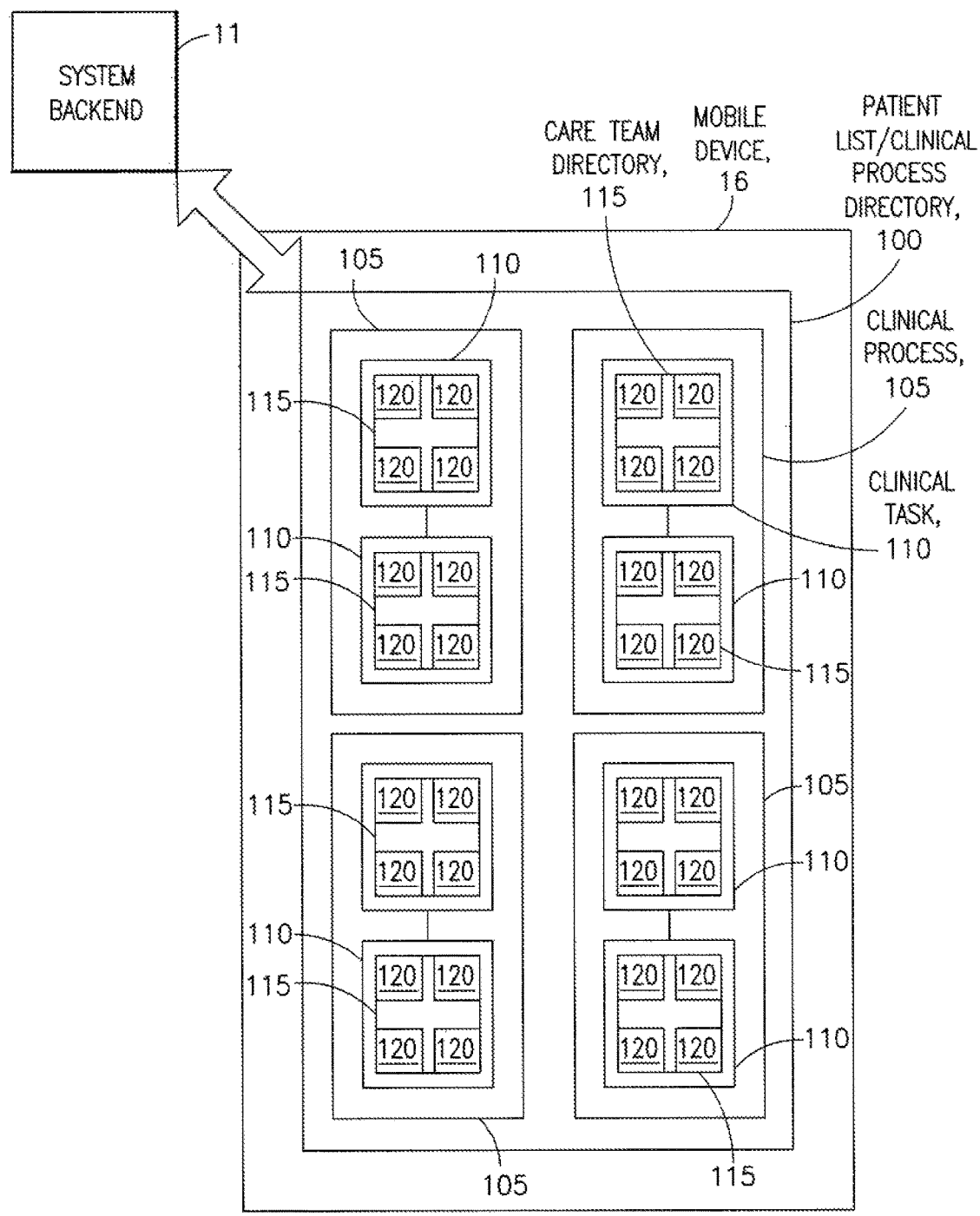
FIG. 1A illustrates a block diagram illustrating the communication between a system backend and a mobile device.

It is noted that the mobile devices 16 are in communication with the system backend 11. Referring now to FIG. 1A, a diagram illustrating the communication between system backend 11 and mobile devices 16 is shown. In one aspect of the disclosed embodiment, the mobile devices 16 are configured to present (e.g. on a user interface on the display of a mobile device 16) a list of patients corresponding to a clinical process directory 100 to a user. Each listed patient of the list of patients presented by the mobile device 16 is received from and dynamically updated by the system backend 11. In one aspect of the disclosed embodiment, the list of patients 100 presented by the mobile device substantially corresponds to a listing of clinical processes. The list of patients is described in greater detail in SYSTEM FOR SETTING AND CONTROLLING FUNCTIONALITIES OF MOBILE DEVICES as described in U.S. Provisional Patent Application 61/939,104 filed on Feb. 12, 2014, and Non-provisional U.S. application Ser. No. 14/621,281, filed Feb. 12, 2015, which were previously incorporated by reference in their entirety. The patient list disclosed in U.S. application Ser. No. 14/621,281 provides the user of the mobile device 16 with a patient centric access to clinical processes maintained by the system backend 11. The mobile device 16 is further configured to receive and present (e.g. on the user interface on the display of mobile device 16) one or more clinical process directory 105 from the system backend 11, each clinical process directory substantially corresponding to each listed patient (e.g. each clinical process) as described in U.S. application Ser. No. 14/621,281. The clinical process directory 105 is comprised of different selectable elements where each selectable element of the clinical process directory represents a different clinical task 110 and its location. The selectable elements are selectable by the user via the device user interface as will be described in further detail below. In one aspect, the predetermined characteristics of the mobile device 16 enable a user to alter the state of a corresponding selectable element within the clinical process directory 105. Altering the state of a selectable element within the clinical process directory is changing the state of a clinical task 110 and may include, for example, signaling that a user is on the way to a clinical task 110 and the associated clinical task location based on a resolved location of a mobile device 16. However, in other aspects, altering the state of a selectable element may also include escalating a clinical task 110. In one aspect of the disclosed embodiment, each of the selectable elements (e.g. clinical tasks 110) within the clinical process directory further corresponds to a care team directory 115 associated with each patient clinical task. The care team directory 115 is generated and dynamically updated by the system backend 11 and includes a listing of available care members of a patient clinical team associated with a patient clinical task. The care team directory 115 maintained by the system backend 11 and presented by the mobile device 16 may comprise one or more care team directory selectable elements 120. The care team directory selectable elements 120 may be associated with a care member of a patient clinical team (e.g. each of the different selectable elements represents a different corresponding member of the clinical team that is associated with the corresponding clinical task 110 of the clinical process 105) and reflect the availability of the care member of the patient clinical team based on the care member's location and/or proximity. In other aspects, the selectable elements within the clinical process directory 100 also corresponds to any suitable information in a clinical setting and pertaining to a clinical process, for example, clinical laboratory work or laboratory results. The system backend 11 is able to maintain and dynamically update the clinical process directory 100, the clinical process 105, clinical task 110 and the care team directory 115 based on the resolved proximities of the mobile devices 16 within the system. The dynamically updated clinical process directory 100, the clinical process 105, clinical task 110 and the care team directory 115 is also dynamically represented on the mobile devices 16 in real time. The dynamical enhancement and updating of care team directories 115 is described below in greater detail.

Referring again to FIG. 1, in one aspect of the disclosed embodiment, the system backend 11 also has an Application Programming Interface (API) module 117. The enterprise application 111 can communicate with the API module 117. The API module 117 provides an interface for a third party user 17 to access clinical data from a generated clinical process 105 (e.g. clinical process directory 100, the clinical process 105, clinical task 110 and the care team directory 115) corresponding to a particular patient with the system backend 11 substantially in real time. In one aspect of the disclosed embodiment, third party users 17 include third party application makers which request access to at least a portion of the information associated with the clinical process directory 100. The access third party user 17 has with the API module 117 will allow the third party user 17 access to the clinical process directory 105 and care team directory 115 and to generate a user interface substantially similar to that of the representation of the clinical process directory 100 and care team directory 115 on the mobile device 16. In one aspect of the disclosed embodiment, third party users 17 may include, for instance, web developers making healthcare tracking portals, widget makers which display information related to patients or any other suitable application. Third party users 17 can also include suitable hardware manufacturers, for instance, those that create devices for tracking a clinical process 105. For instance, this may include bedside displays or smart watches or wearable devices or any other suitable devices which may access a patient's clinical process 105. In one aspect of the disclosed embodiment, the API module 117 functions as an intermediary interface between the third party user 17 and the enterprise application 1111. The third party user 17 can access the clinical process directory 100 and care team directory 115 generated by the system backend 11 by making calls to the API 117. It is noted that any changes to the state of the clinical process directory 100, or clinical processes 105, clinical tasks 110 or care team directory 115, whether caused by a mobile device 16 or by the system backend 11 will immediately and dynamically available on all devices which can access the API module 117.

Figure 2:
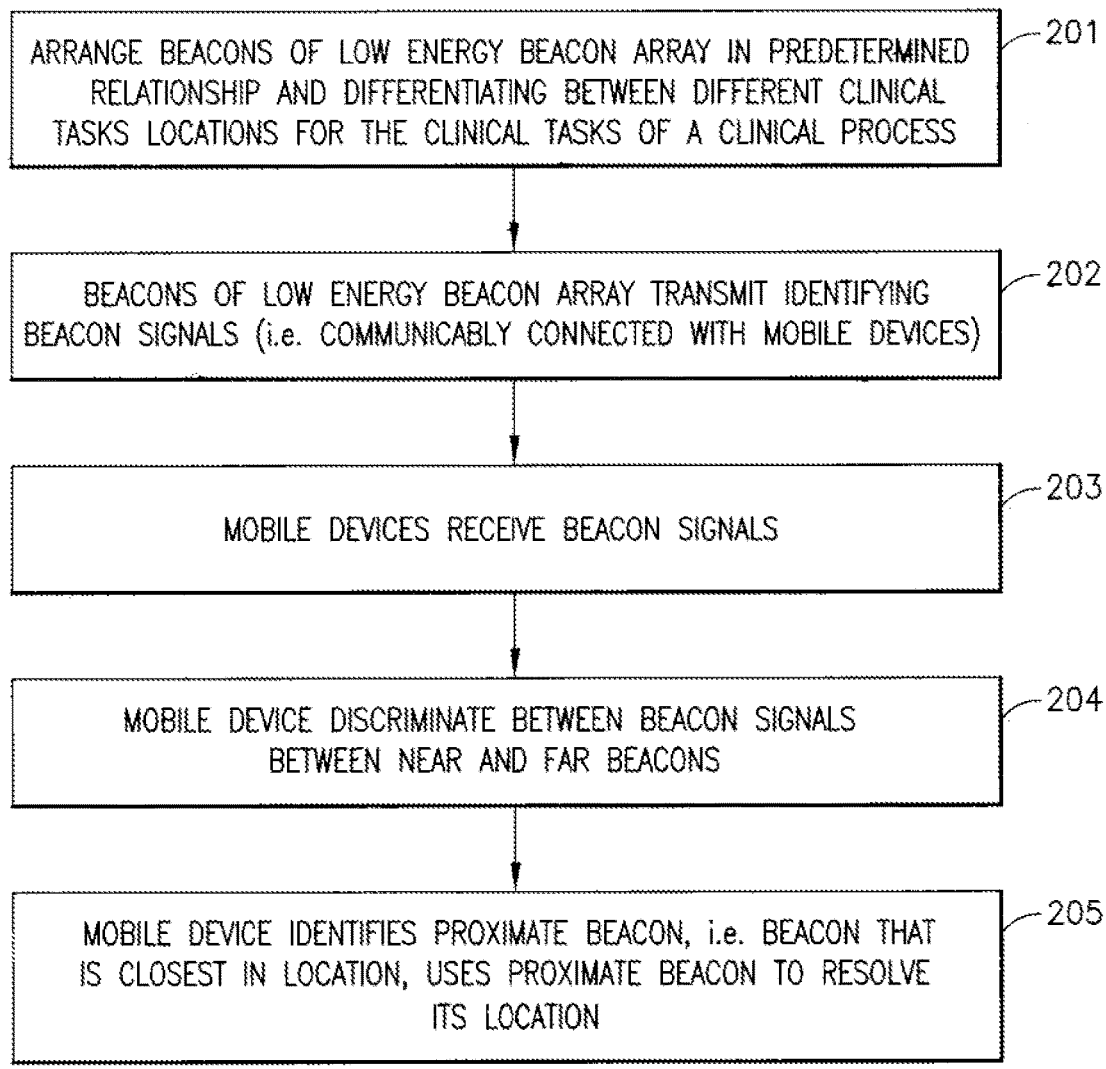
FIG. 2 illustrates an exemplary flowchart of the operation of the system.

Referring now to FIG. 2, an exemplary flowchart of the operations of the localization system is shown. At block 201, the Beacons 15 of the low energy beacon array is arranged in a predetermined relationship (for instance, in each location of an array space) which allow differentiating between different clinical task locations for the clinical tasks of a clinical process. At block 202, the Beacons 15 transmit identifying beacon signals. In one aspect of the disclosed embodiment the Beacons 15 are communicably connected to mobile devices 16. At block 203, the mobile devices 16 receive the Beacon 15 signals. At block 204, the mobile device 16 can discriminate between the Beacon 15 signals between near and far Beacons 15. At block 205, the mobile device 16 identifies the proximate Beacon 15 (e.g. the Beacon that is the closest in proximity) and uses the proximate Beacon 15 to resolve the proximity of the mobile device 16.

Figure 3:
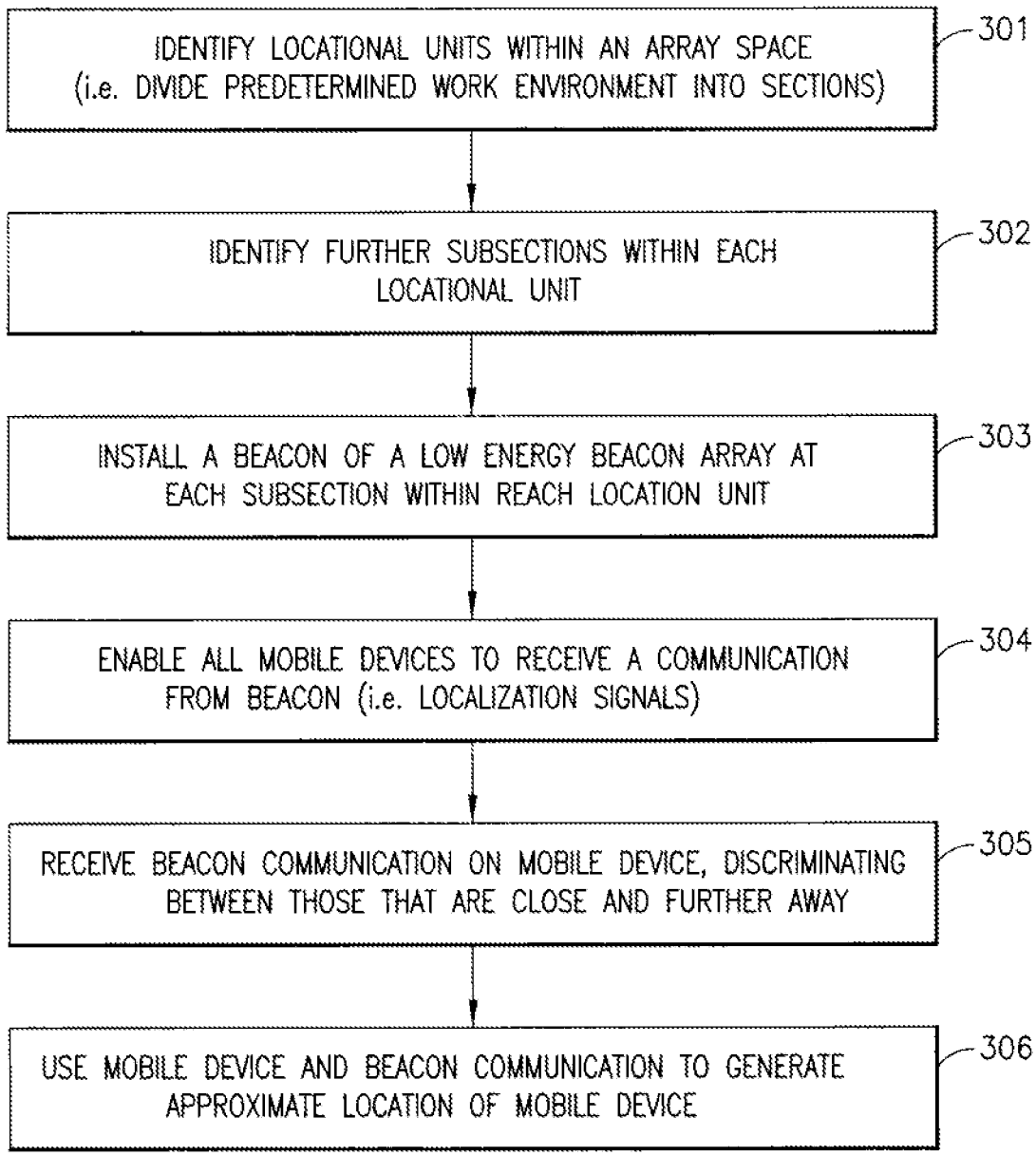
FIG. 3 illustrates another exemplary flowchart of the operation of the system.

Referring now to FIG. 3, another exemplary flowchart of the operations of the localization system is shown. At block 301, the locational units within an array space (i.e. a predetermined work environment) is identified. In one aspect of the disclosed embodiment, the array space is a hospital or a healthcare facility in this context that is divided into different wards or wings. At block 302, further subsections of each locational unit may be identified. For instance, once a hospital has been divided into different wards or wings, the wards or wings may further be divided into smaller locational subunits or subsections. For instance, a ward may be divided up into beds or rooms. In alternate aspects, it may be divided up into any suitable form of subunits, for instance—hallways, offices, etc. At block 303, a Beacon 15 of the low energy beacon array is installed at each subsection within each locational unit. At block 304, each mobile device 16 is configured or enabled to receive a communication from the Beacon 15. As noted, in one aspect, this communication is a beacon signal transmitted by the Beacon signal transceiver 15a and received by the Beacon signal receiver 16a. In alternate aspects, these may be any suitable form of localization signals. At block 305, the mobile devices 16 receive the beacon signals with the beacon signal receiver 16a and discriminate between the beacons that are closes and further away. The mobile device 16 may use this to identify the proximate beacon (i.e. the one closes to the mobile device) and use this to resolve the proximity of the mobile device 16 at block 306 to a Beacon 15.

Figure 5:
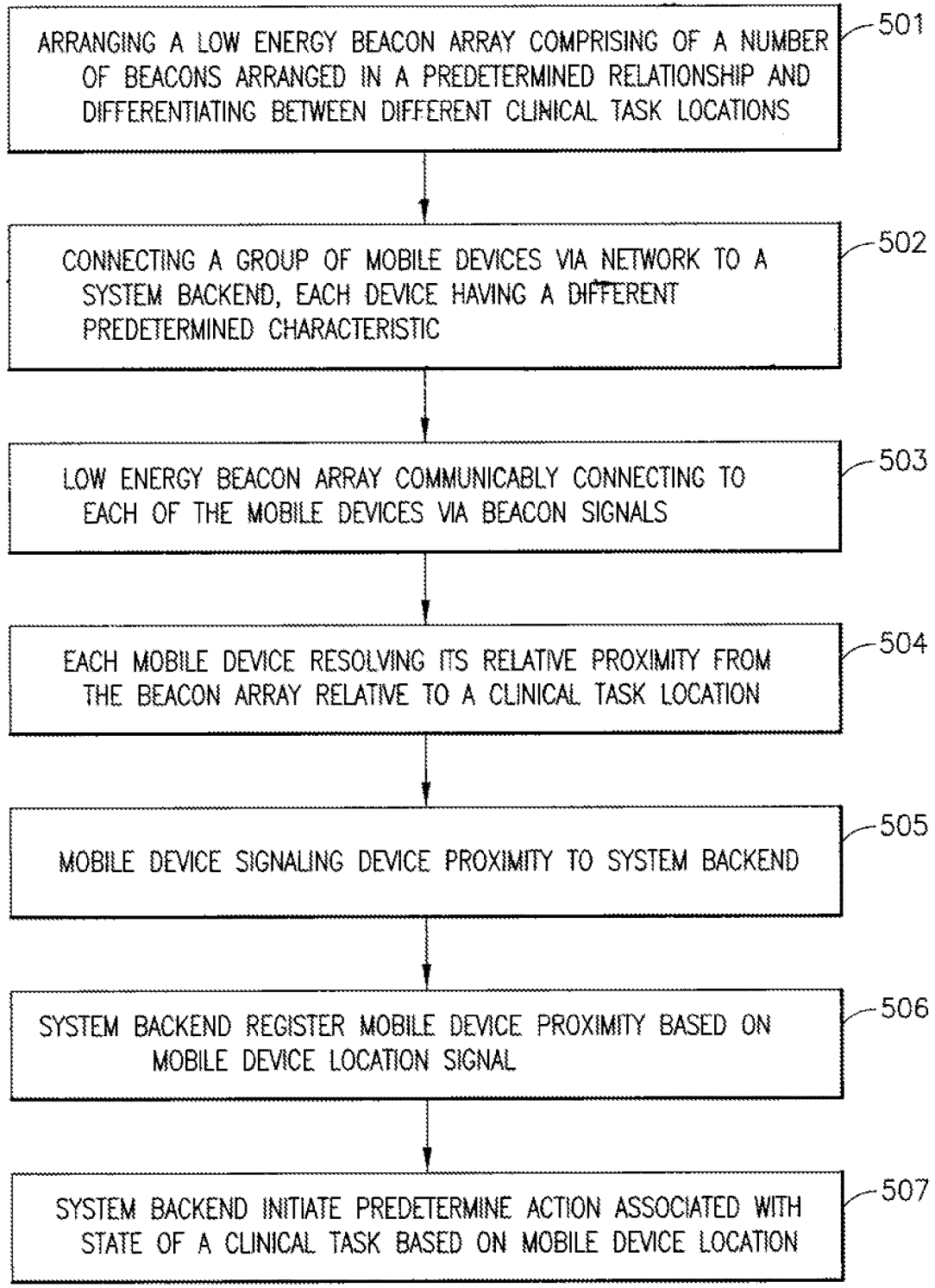
FIG. 5 illustrates another exemplary flowchart of the operation of the system.

Referring now to FIG. 5, yet another exemplary flowchart of the operations of the localization system may be shown. At block 501, the Beacons 15 of the low energy beacon array is arranged in a predetermined relationship (for instance, in each location of an array space) which allow differentiating between different clinical task locations for the clinical tasks 110 of a clinical process 105. At block 502, a group of mobile devices 16 are connected via the network to the system backend, each mobile device 16 may have a different predetermined characteristic. As noted above, the predetermined characteristics may be different functional groups or user permissions associated with each mobile device 16 similar to those described in, for example, the one described in SYSTEM FOR SETTING AND CONTROLLING FUNCTIONALITIES OF MOBILE DEVICES as described in U.S. Provisional Patent Application 61/939,104 filed on Feb. 12, 2014, and Non-provisional U.S. application Ser. No. 14/621,281, filed on Feb. 12, 2015, the disclosures of which were previously incorporated by reference their entireties. At block 503, the low energy beacon array of Beacons 15 may be communicably connected to each of the mobile devices 16 via beacon signals (i.e. localization signals). Each mobile device 16 can resolve its relative proximity from the beacon array relative to a clinical task 110 location in block 504. At block 505, each mobile device 16 may signal its resolved relative mobile device proximity to the system back 11. At block 506, the system backend 11 registers the mobile device 17 proximity based on the mobile device 16 localization performed at block 504. At block 507, the system backend 11 initiates a predetermined action associated with the state of a clinical task based on the resolved mobile device proximity at block 507. The system backend 11 In one aspect of the disclosed embodiment, the predetermined actions include changing a state of the clinical task 110 within the clinical process 105. In other aspects, the predetermined actions include registering the real time presence of a mobile device 16 relative to the location represented by a clinical task 110. The predetermined action may also be selecting between sending and not sending a communication to the mobile device 16 based on registering the mobile device real time presence at the proximity represented by the clinical task. The mobile devices 16 is configured to receive communications from the system backend 11 related to a clinical process 105. For instance, the communication may be, for instance, an alarm generating signal or a signal turning off an alarm on the mobile device. The predetermined action may also be escalating an alarm to another of the mobile devices based on the real time presence of the mobile device 16 and other mobile devices 16. The predetermined action may also include mapping the group of mobile device 16 proximities as well as tracking the real time presence of each of the mobile device 16 with respect to a clinical task 110. In yet alternate aspects, the predetermined action may be registering and tracking of each mobile device 16 proximity and real time presence relative to a corresponding clinical task 105. In alternate aspects, any suitable predetermined action may be used.

Figure 4:
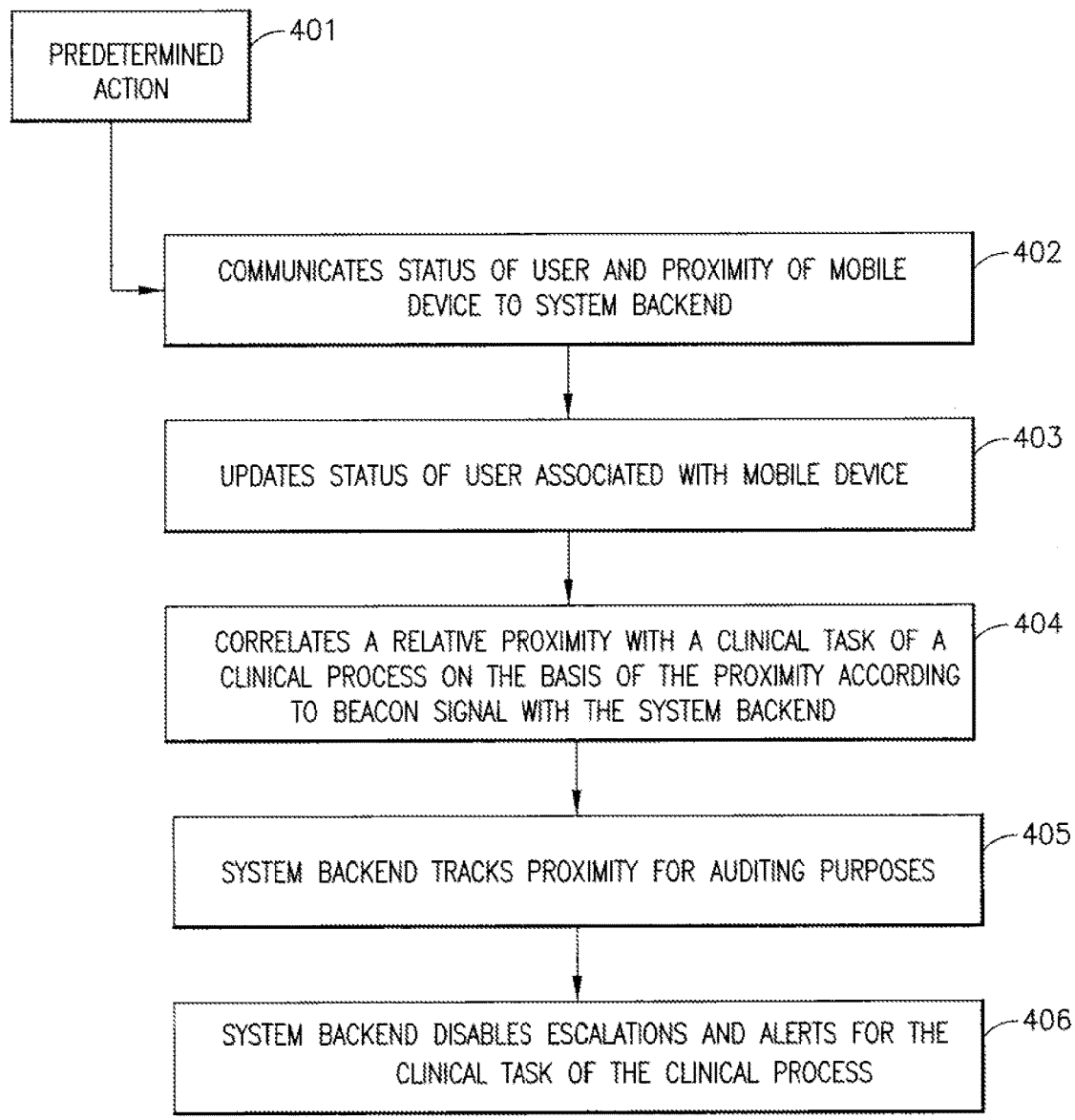
FIGS. 4-4A illustrates another exemplary flowchart of the operation of the system.

Referring to FIG. 4, several exemplary examples of predetermined actions as disclosed in FIG. 5 may be shown. The predetermined actions may include multi-stepped actions. For instance, the predetermined action 401 may include block 402 where the mobile device communicates status of the user and a relative proximity of a mobile device 16 to the system backend 11. The system backend 11 in block 403 can update the status and relative proximity of a user associated with the mobile device 16 based on the information received in block 402. In one aspect of the disclosed embodiment, this updated status and relative proximity of a user can manifest in an updated care team directory 115, or an updated clinical process directory 105 which will be described in greater detail below. The system backend 11 can further correlate the mobile device's relative proximity with a clinical task 110 of a clinical process 105 on the basis of the resolved proximity according to the detected beacon signal. That is, the system backend 11 can determine whether the resolved proximity for a mobile device 16 correlates to a proximity or location associated with a physical task. For example, if a clinical task 110 of a clinical process 105 has a location or proximity associated with a particular room, if the mobile device 16's resolved proximity is near the beacon found in that particular room, then the system backend 11 will be able to correlate the resolved proximity with the location associated with the clinical task 110 of the clinical process 105. The system backend 11 may be able to determine that when a mobile device 16 has been detected within the proximity of the particular location of the clinical task 110, then it would appear that the user of the mobile device 16 has arrived to address that clinical task 110 of the clinical process 105. At block 405, the system backend 11 may track mobile device proximity for auditing purposes, for example, to see how quickly users are arriving at locations associated with clinical tasks 110 of a clinical process 105 in response to alerts or notifications. In alternate aspects, any other data used for auditing performance may be suitable. At block 406, the system backend 11 may also disable escalations or alerts for a clinical task of the clinical process 105 based on the mobile device 16 proximity. For instance, if a user's mobile device 16 arrives to be within proximity of a location associated with a clinical task 110 of a clinical process 105, the system backend 11 may disable the alerts or notifications associated with that clinical task 110 because a user has arrived to address that clinical task 110. On the other hand, in other situations, if no user arrives to the location associated with the clinical task 110, the system backend 11 will escalate the alert to a higher level to ensure that the clinical task is completed. In yet other situations, the system may be used to enhance patient care teams and improve patient care dynamically, on a real-time or on a substantially real-time basis. Dynamic enhancement of patient care teams (e.g. generating a dynamically updated care team directory 115) is described further below in greater detail.

Figure 4A:
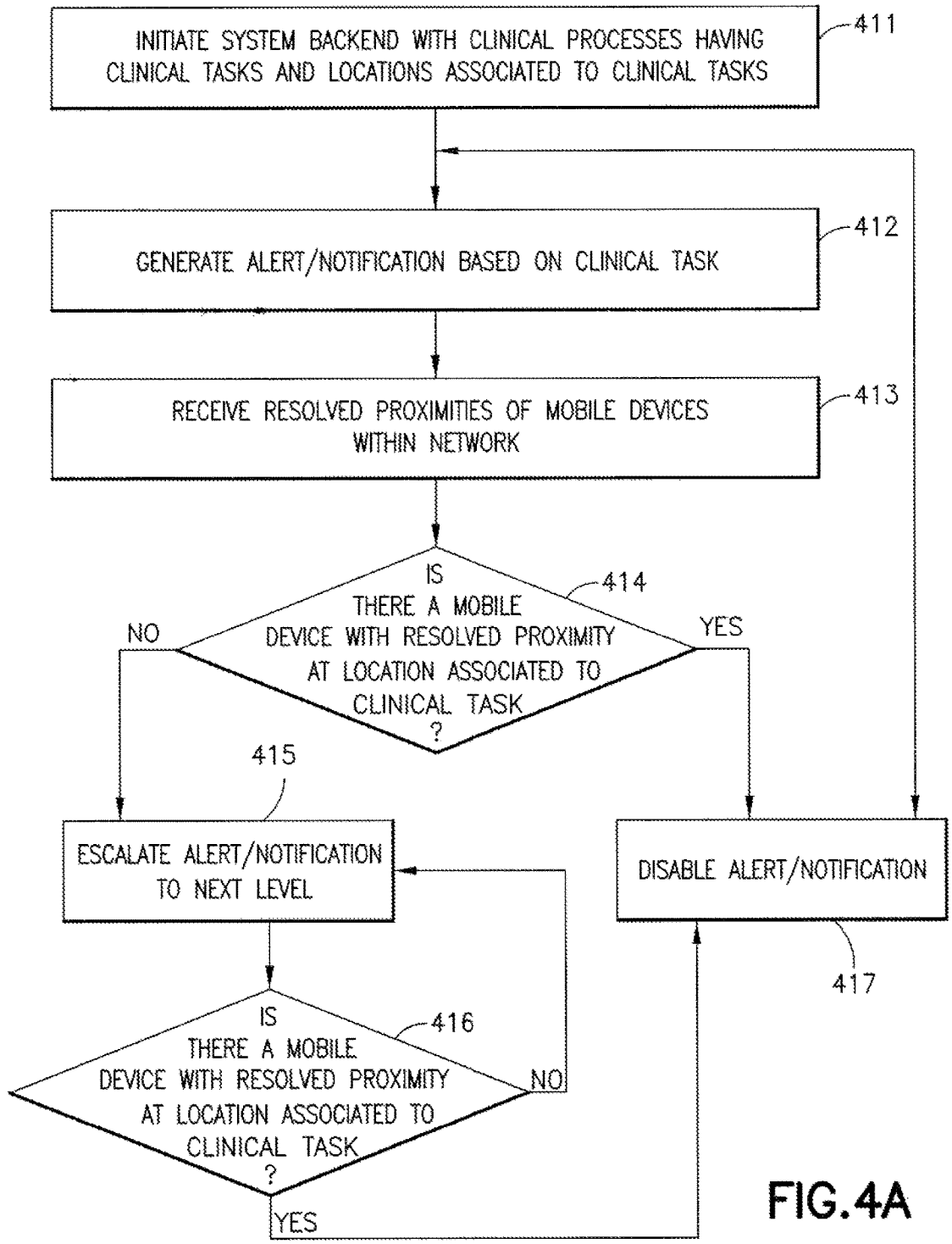

Referring now to FIG. 4A, a flowchart illustrating an exemplary operation of alerts escalations may work. At block 411, a system backend 11 is initialized with a clinical process directory 100, which, as noted is communicated to a mobile device 16 and presented on the mobile device 16 in the form of a patient list. The clinical process directory 100 maintained by the system backend 11 and communicated to the mobile device 16 has one or more clinical process 105c. Each clinical process 105 includes at least one clinical task 110. Each of the clinical tasks 110 may have a location or proximity or beacon associated with the clinical task 110. At block 412, the system backend 412 generates an alert/notification based on a clinical task 110 of the clinical process 105. At block 413, the system backend 11 may receive resolve proximities of the mobile devices 16 within the network 12 that are communicating with the system backend 11. At block 414, the system backend 11 determines whether there is a mobile device 16 with a resolved proximity that is at the location associated to the clinical task with the alert/notification that is still currently active. If there is a mobile device 16 with a resolved proximity at the location associated with the physical task, the flow goes to 417, where the system backend 11 disables the alert/notification. This may mean, for example, that the system backend 11 recognizes that a mobile device 16 has arrived at the location associated with the clinical task 110 in order to resolve the clinical task 110. However, if at block 414, no mobile devices 16 with resolved proximities at the location associated with the physical task, the flow may go to block 415, where the system backend 11 may escalate the alert/notification to the next level. This may mean, for instance, whereas generally, the alert/notification is generally sent to one or a small number of individuals, as the alert is escalated, the alert is brought to the attention of more and more individuals—for instance, supervisors or managers to ensure that the clinical task 110 is resolved. In one aspect of the disclosed embodiment, the system backend 11 is configured to dynamically enhance a care team directory 115 for a clinical task 110 by expanding the number of the care team members 120 as part of the care team directory 115 associated with the clinical task 110. This ensures that the alert will be sent to the most members of the care team with respect to a clinical task 110. The dynamic enhancement of the care team directory 115 is described below in greater detail. The system backend 11 at block 416 also checks to see if there is a mobile device 17 with are solved proximity at the location associated with the clinical task 110 periodically. If a mobile device 16 has a resolved proximity at the location associated with the clinical task, the escalated alert/notification is disabled and the flow returns to 417. If, however, there is not, the flow returns to block 415 where the query will continue until some user responds to the alert/notification.

Figure 6:
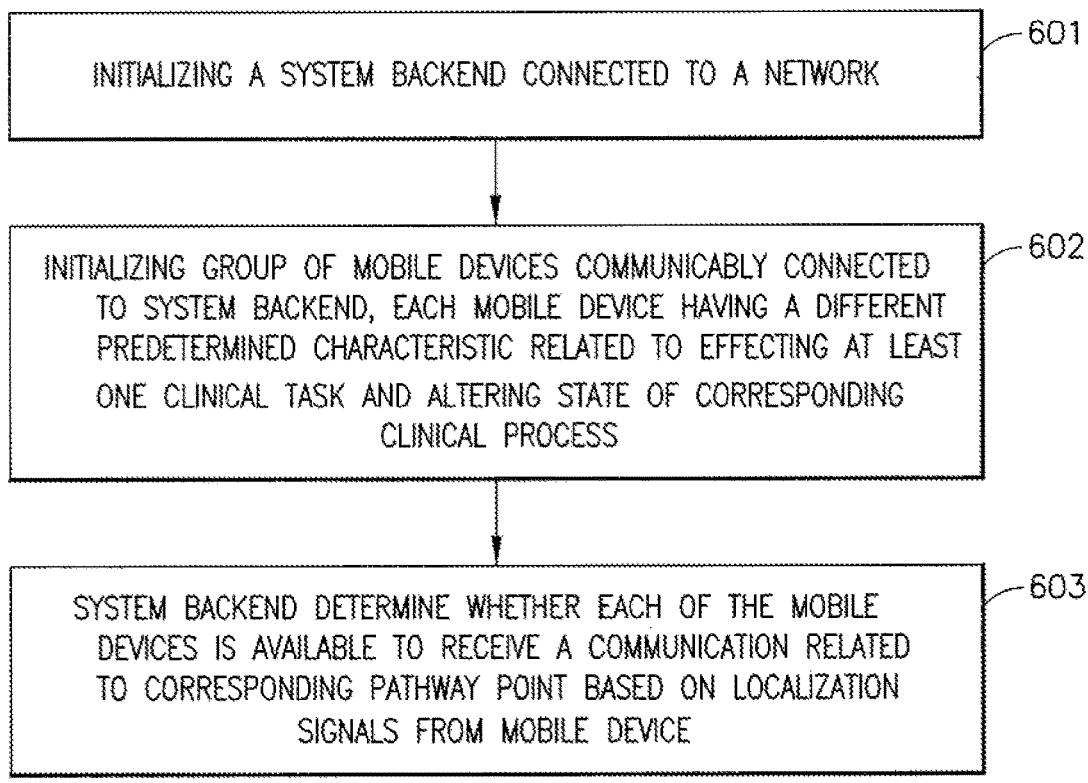
FIG. 6 illustrates another exemplary flowchart of the operation of the system.

Referring now to FIG. 6, yet another exemplary flowchart of the operations of the system may be shown. At block 601, a system backend connected to a network is initialized. At block 602, a group of mobile devices 16 is initialized, each mobile device communicably connected to the system backend 11. Each mobile device may have a different predetermined characteristic related to the effecting of at least one physical task and altering the state of a corresponding clinical process related to that clinical task. At block 603, the system backend 11 determines whether each of the mobile devices 16 may be available to receive a communication related to the corresponding clinical task based on localization signals from the mobile device 16.

Figure 7:
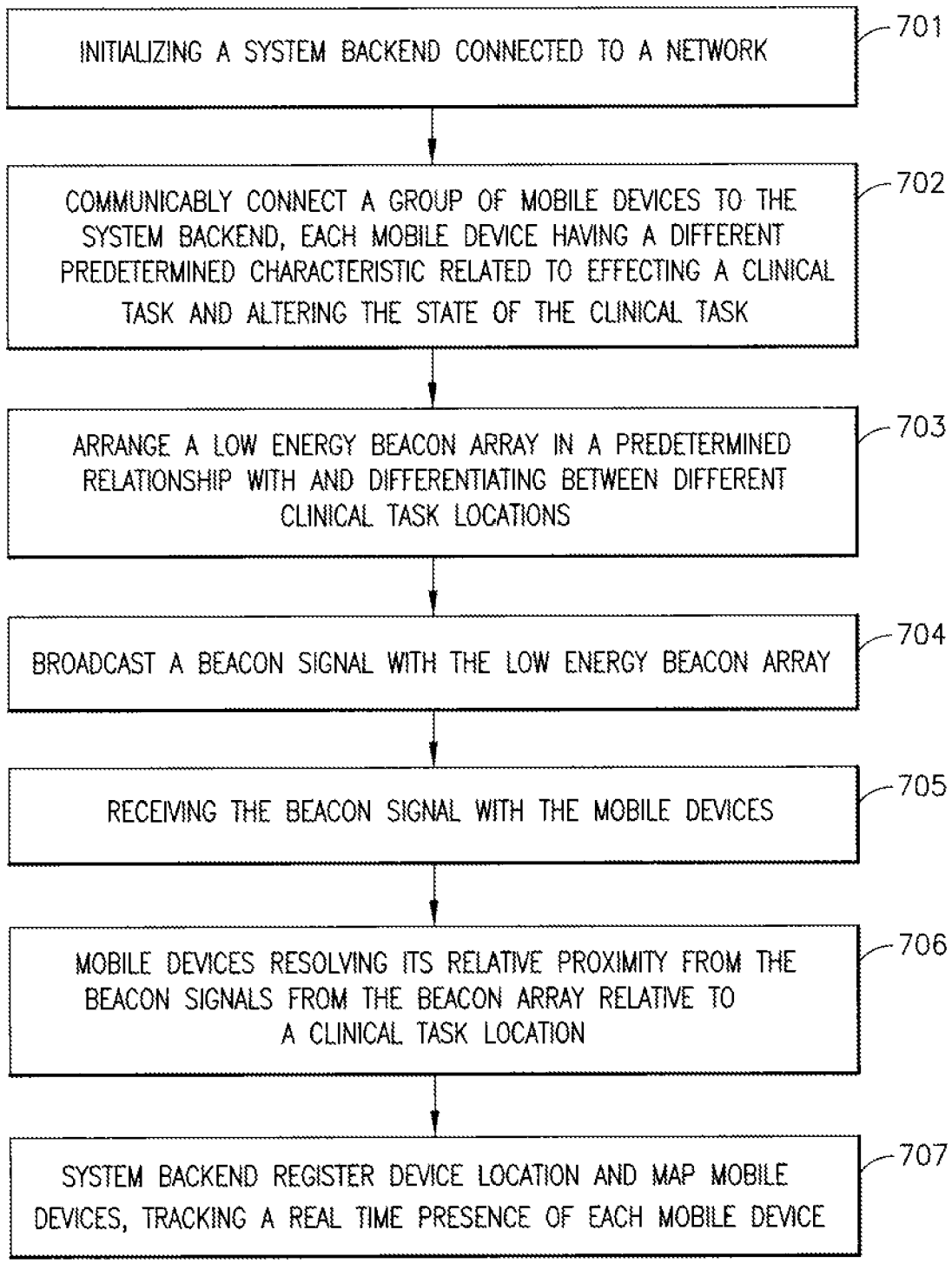
FIG. 7 illustrates another exemplary flowchart of the operation of the system.

Referring now to FIG. 7, yet another exemplary flowchart of the operations of the system may be shown. At block 701, a system backend 11 connected to the network is initialized. At block 702, a group of mobile devices 16 may be communicably connected to the system backend 11, each mobile device having a different predetermined characteristic related to effecting a physical task and altering the state of a corresponding clinical task. At block 703, a low energy beacon array of Beacons is arranged in a predetermined relationship with and differentiating between different clinical task locations. At block 704, each Beacon 15 of the low energy beacon array broadcasts a beacon signal. At block 705, the mobile devices 16 receive the beacon signal with the beacon signal receiver 16a. At block 706, each mobile device 16 resolves its proximity from the beacon signal from the low energy beacon array relative to a clinical task location of a clinical process. At block 707, the system backend 11 registers each mobile device's proximities and map each of the mobile devices 16, allowing the system backend 11 to track a real-time proximity of each mobile device 16.

The Beacons 15 may also facilitate other actions by leveraging the localization capabilities of mobile devices 16 using the beacons 15. For instance, as noted previously, the beacons 15 may facilitate a means to dynamically enhance patient care teams and to enhance clinical work flows and improve patient care in a substantially real-time basis. This may be accomplished in an instance of a patient care clinical process 105 having multiple patient clinical tasks 110 (for example, medicine, diagnostics, patient laboratory work, etc.). Within this patient care context, there are multiple individuals (i.e. members of a patient care team) involved in facilitating and carrying out the clinical process 105. The patient care team may include, for example, nurses, doctors, lab technicians and any other suitable members of a patient care team. The patient care team may also include, for instance, administrators, managers and overseers for each group. The patient care team members within a patient care system may be dynamically selected within a healthcare facility (which may be integrated or distributed). Each of the patient care team members may be associated with a mobile device 16. Each of the mobile devices 16 may be able to resolve its relative proximity based on the beacons 15 similar to what is described above. Based on the resolved proximity of each mobile device 16 (and, by extension, each patient care team member), the system backend 11 may, dynamically and in real-time, make enhancements to the patient care team to generate a care team directory 115. With knowledge of the respective resolved proximities of each patient care team member, the system backend 11 may dynamically generate, in real-time, a care team directory 115 by determining status (e.g. whether a patient care team member is busy with another task) or by determining availability (whether a patient care team member is within a certain facility) of the patient care team members. In other aspects, the system backend 11 may also further enhance a patient care team by other criteria in addition to the resolved proximities of each patient care team member. Such criteria may include, for instance, manually entered status of each patient care team members on their mobile devices 16 (e.g. if a patient care team member indicated that they are on a break or if they are having a meal).

Figure 15:
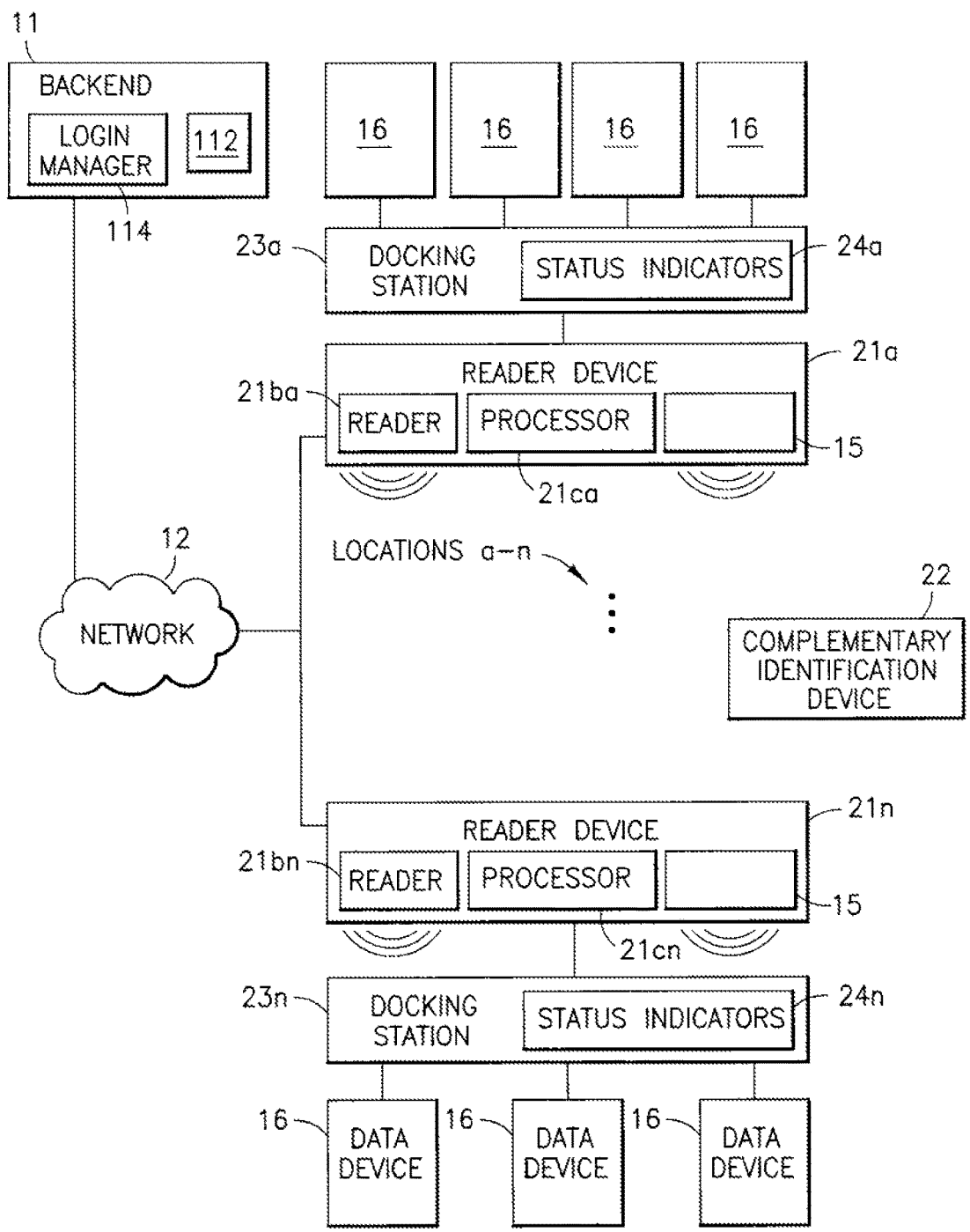
FIG. 15 illustrates a schematic representation illustrating an overview of the system utilizing a system for proximity-based automated login operations.
Figure 16A:
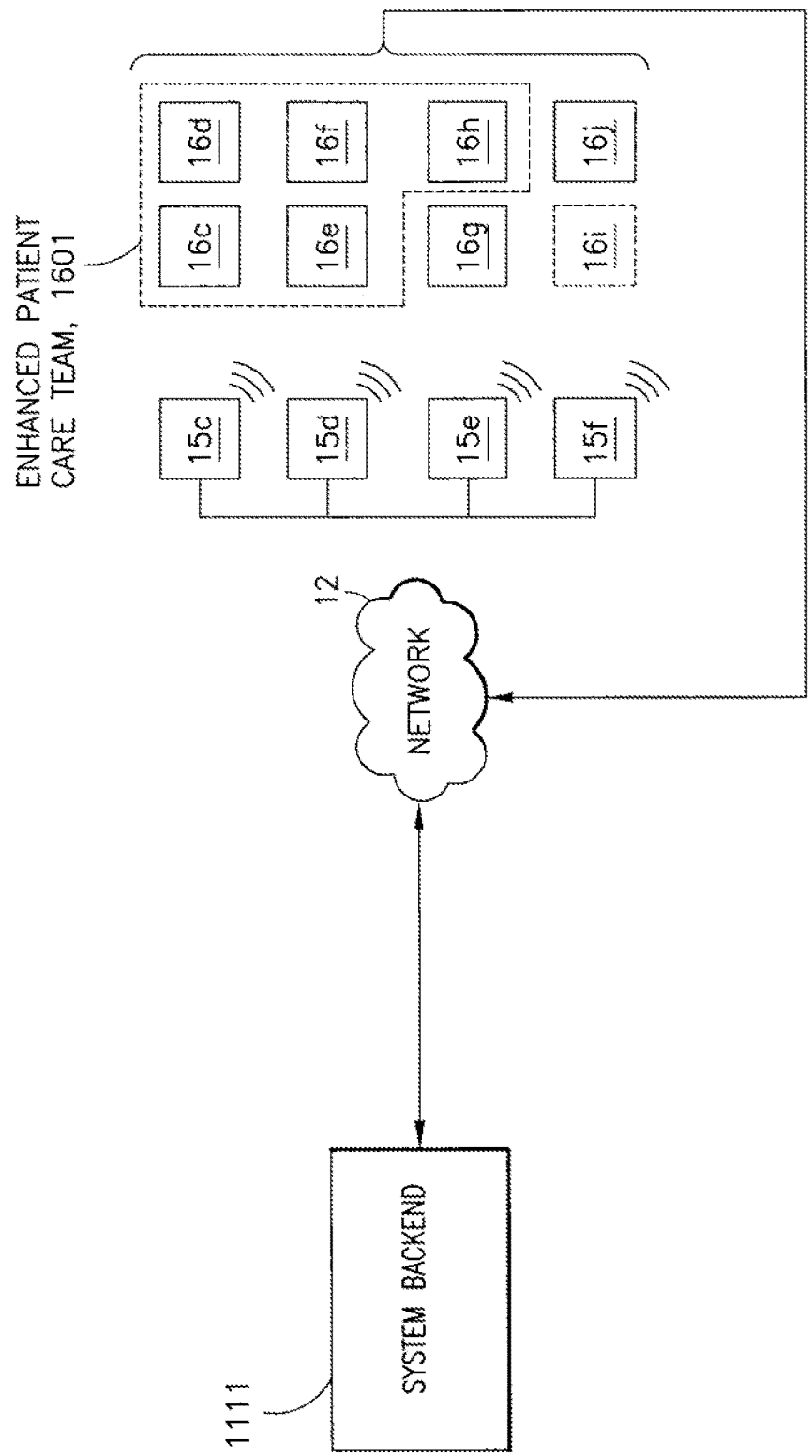

Referring now to FIGS. 16A and 16B, an example of the enhancing a patient care team is shown. In one aspect of the disclosed embodiment, the enhanced patient care team is represented on the mobile device as the care team directory 115 and is communicated to the mobile device 16 from the system backend 11. The system backend 11 is able to dynamically resolve care team members of a patient clinical team by dynamically updating a care team directory 115. As noted previously, the care team directory 115 is generated by the system backend and is presented by the mobile device 16 as one or more care team directory selectable elements 120 associated with an available patient care team member based on the resolved proximity of each patient care team member according to their associated mobile device 16. In FIG. 16A, a total group of patient care team members 16*c-j* is shown. The total group of patient care team members 16*c-j* includes all of the care members of a patient care team within a hospital, healthcare facility or clinical facilities responsible for the patient care, or patient care related task for a given patient(s). The system backend 11 can dynamically identify and generate the patient care team. For example, the patient care team may include all of the nurses assigned (in a backend registry) to take care of a particular patient during his stay (e.g. with respect to a clinical process for a particular patient), and are linked via responsive mobile device 16*c-j* to patient system backend 11 during a common predetermined period of time (e.g. a normal shift period) as well as all of the doctors, laboratory technicians and administrators who are tasked to provide care to that particular patient similarly connected to the backend. The low energy beacons 15*c-f* may substantially correspond with the beacon 15 described previously and are arranged within an array space. The low energy beacons 15*c-f* may also be detectable by mobile devices 16*c-j*, which also substantially corresponds with the mobile device 16. Each of the mobile devices 16*c-j* is associated with a particular member of a patient care team. This association may be tracked in real time by the system backend 11 as described in greater detail herein. Each mobile device 16*c-j* may be configured to resolve its relative proximity based on the detected proximity to one or more of the low energy beacons 15*c-f*. The respective resolved proximities may enable the system backend 11 to determine the relative positions of each patient care team member within a healthcare facility (or across multiple facilities). The system backend 11 may be configured to dynamically generate the patient care team based on the automated login initialization described in greater detail further herein (see FIG. 15). As may be realized, the care team members may be coupled or linked, via their mobile devices 16*c*-16*j* to each other, sharing various functions and data on their devices with respect to the given patient(s). The care team members, and more specifically the respective mobile devices 16*c*-16*j* associated with each member of the patient care team (for the purposes of simplicity, the patient care team member and his/her associated mobile device 16*c-j* are interchangeably used), as well as functions and data associated therewith are dynamically modified, thereby enhancing information and function of the care team members, and hence of the patient care team, based on proximity data. The system backend 11 may thus dynamically enhance or generate the enhanced patient care team 1601 (corresponding to the care team directory 115) based on the resolved proximities of each patient care team member (represented by mobile devices 16*c-j*). Such enhancement may be performed by the system backend 11 whenever a change in status, based on the resolved proximities of the mobile devices 16*c-j*, is detected. Such enhancement operations may be performed iteratively (that is, whenever a change is detected, that is, in real-time or substantially real-time) or it may be done after sufficient changes (change quantum), based on the resolved proximity of mobile devices 16*c-j*, is detected. For example, the system backend 11 can dynamically change the state (e.g. the availability) of the care team directory selectable elements 120 associated with patient care team member based on the patient care team member's location or current availability based on the resolved proximity of the patient care team member's mobile device. In other aspects, the enhancement may be performed at any suitable timeframe to enable substantially dynamic updating and enhancing of the updated patient care team 1601. The enhanced patient care team 1601 may be one which is filtered by proximity to a predetermined location or locations related to a given clinical process 105 (for example, when patient team members automatically login within the predetermined location(s) or logout within the predetermined location(s)). Mobile device 16*i*, shown in phantom in FIG. 16A) is representative of devices not included by the backend 11 as part of the enhanced patient care team 1601 (e.g. devices) not yet logged into by a patient care team member of the facility. Further, a patient care team member associated by the backend 11 with a particular patient process, but not (based on resolved proximity) within the predetermined location(s) related or bound to the given patient care process (for instance, represented by mobile device 16*j*) will also not be included as part of the enhanced patient care team 1601 (e.g. the respective device may be dynamically decoupled from the shared functions and data of the team and the functionality and shared information of the team member's mobile devices 16 is dynamically changed by the system backend 11 to reflect decoupling or removal of a patient care team member). All of these changes are reflected as dynamically updated changes of state of the care team directory selectable elements 120 within a care team directory 120 maintained by the system backend 11 and presented by a mobile device 16. Further, even if a mobile device 16 is within such related predetermined resolved location (for example, represented by mobile device 16*g*), if the patient care team member associated with the mobile device 16*g* is disassociated with a particular patient care process, then that patient care team member will also not be included as part of enhanced patient care team 1601. Similarly, the system may dynamically enhance the patient care team members by adding patient care team members to the given enhanced patient care team 1601 based on resolved proximity in a manner similar to, but opposite to that described above. By leveraging the localization capabilities of the mobile devices 16*c-j* and the beacons 15*c-f*, the system backend 11 is able to create an enhanced patient care team 1601 that comprises a subset of the relevant and available patient care team members to enhance the operation of a patient care process.

Referring now to FIG. 16B, the enhanced patient care team 1601, as noted before, is updated and enhanced by the system backend 11 based on changes related to proximity data for the mobile devices 16*c-j* (and FIG. 16B schematically illustrates the system with the enhanced patient care team 1601 having a different enhancement or enhanced status). The changes related to proximity data is represented as changes in the state of a care team directory selectable element 120 of a care team directory 115 generated by the system backend 11 and presented by the mobile devices 16. This may include instances where a change in resolved proximities for each of the mobile devices of the enhanced patient care team 1601 is detected (i.e. the system backend iteratively updates and enhances the patient care team 1601 based on resolved proximity data). For instance, where the patient care team members associated with mobile devices 16*e* and 16*h* (shown in phantom in FIG. 16B) are no longer within proximity of a predetermined location(s) related to a patient care process (for example, the patient care team member may have left the healthcare facility or is in another part of the facility that is not related to a clinical process 105), the system backend 11 dynamically removes them from the enhanced patient care team 1601. In cases where a patient care team member was not originally within proximity to a predetermined location(s) related to a clinical process 105, the enhanced patient care team 1601 may be incrementally updated to include the patient care team member. This may occur, for example, when a patient care team member enters the proximity of predetermined location(s) related or bound to the given clinical process 105 or when a patient care team member logs into their mobile device 16. For example, the patient care team member associated with mobile device 16g was not part of the enhanced patient care team 1601 in FIG. 16A where the patient care team member was not within proximity to a predetermined related or bound to the given patient care process. However, upon entering the proximity of the predetermined location, the system backend 11 may dynamically update the enhanced patient care team 1601 to include the patient care team member associated with mobile device 16g. Further, where new patient care team members are added to the system (for instance, mobile devices 16k and 16l), the system backend 11 can take them into account and determine whether they are to be included as part of the enhanced patient care team 1601 based on their respective resolved proximities. In the example shown in FIG. 16B, mobile device 16k was included as part of the enhanced patient care team 1601, but mobile device 16l was not. As noted previously, the enhanced patient care team 1601 may be continuously updated and enhanced based on the resolved proximities of the mobile devices 16c-j. The enhancement of the patient care team 1601 may occur whenever a change in a resolved proximity for a patient care team member (represented by mobile devices 16c-j) is detected by the system backend.

Figure 16C:
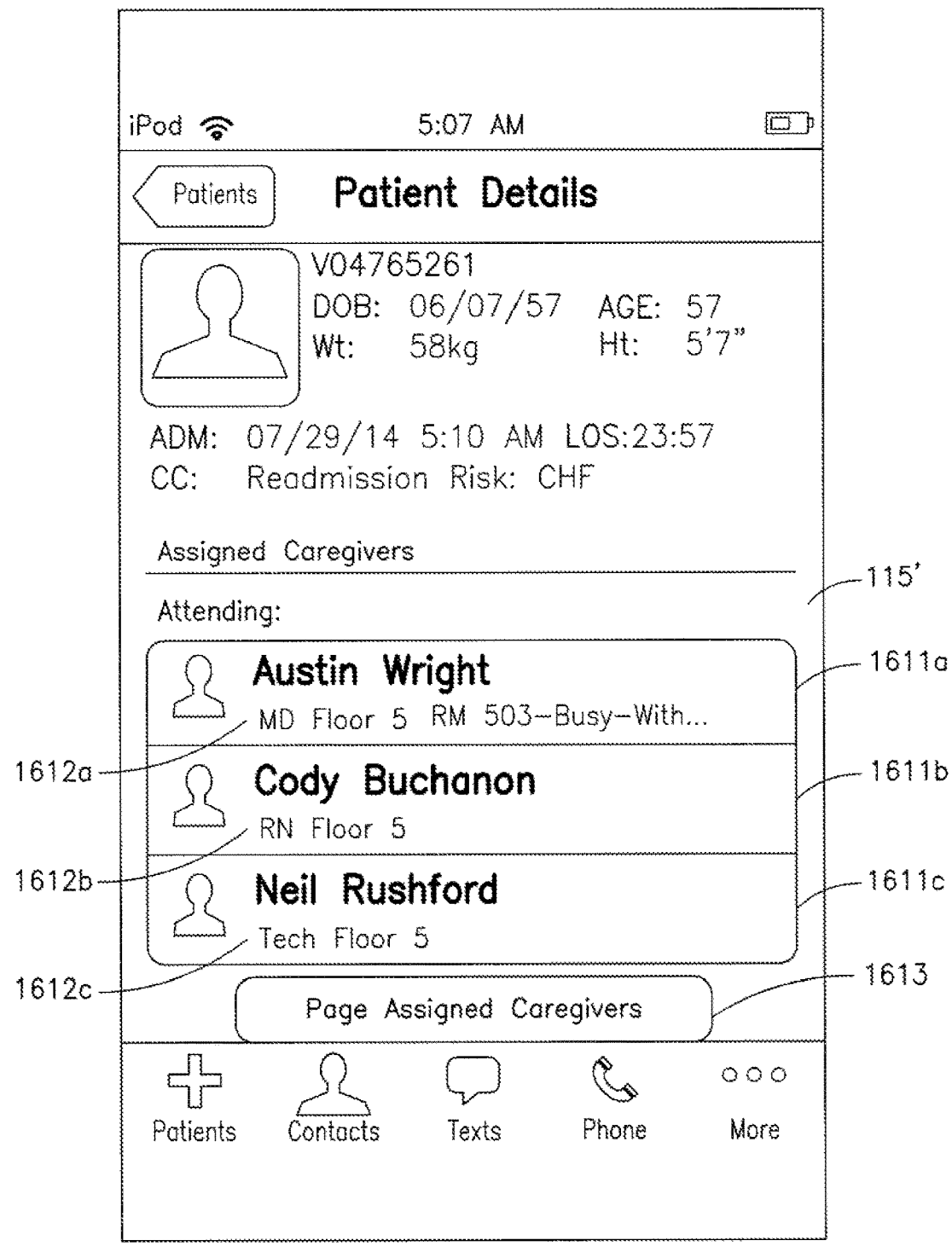
FIG. 16C illustrates an exemplary user interface of a real-time clinical team directory.

The enhanced patient care team 1601 may facilitate and enable many functionalities within a clinical process 105. By grouping patient care team members within the enhanced patient care team 1601, simplified interactions between patient care team members are possible. Instead of situations where a patient care team member must identify another patient care team member related to a patient care process, track down that other patient care team member and communicate with the other patient care team member, the enhanced patient care team 1601 greatly simplifies communications with other patient care team members by providing easy access to patient care team members associated with a clinical process 105 and within proximity to predetermined location(s) related or bound to the given patient care process. For instance, the enhanced patient care team 1601 may be leveraged for generating real-time care team directories 115. As may be realized, the care team directories 115 serve, in one aspect, as a representation (such as may be represented on the mobile device 16 of each patient care team member) of the enhanced patient care team 1601. These real-time care team directories 115, in effect, simplify communication within an enhanced patient care team 1601 by creating a directory of other patient care team members associated with the clinical process 105 and within proximity to location(s) associated with the patient care process. This allows for patient care team members to have a simplified method to find other patient care team members who are working with to effect a patient care process. This is illustrated by FIG. 16C, which shows an exemplary real-time care team directory 115' related to a particular patient care process of a given patient and represented on a mobile device 16. The icons or facets 1611a-1611c of the directory 115' corresponds to the members of the patient care team or the enhanced patient care team 1601 illustrated in FIGS. 16A-16B and described previously. The facets embody, for example, functionalities and data shared with patient care team members. In the exemplary aspect show in FIG. 16C that the real-time care team directory 115' includes resolved proximity data 1612a-c for each patient care team member 1611a-c as well as status information for each patient care team member 1611a-c. The real-time clinical directory 1610 may also include a functionality to page or contact (see page function 1613) all of the patient care team members of an enhanced patient care team 1601. As may be realized, the directory 1610 is enhanced in accompaniment with the enhancement of the patient care team 1601 (e.g. proximity filtering patient care team members as previously described) and the corresponding links between team members, exemplified here by the contact or "page" functionality is commensurately enhanced by proximity resolution.

Figure 16D:
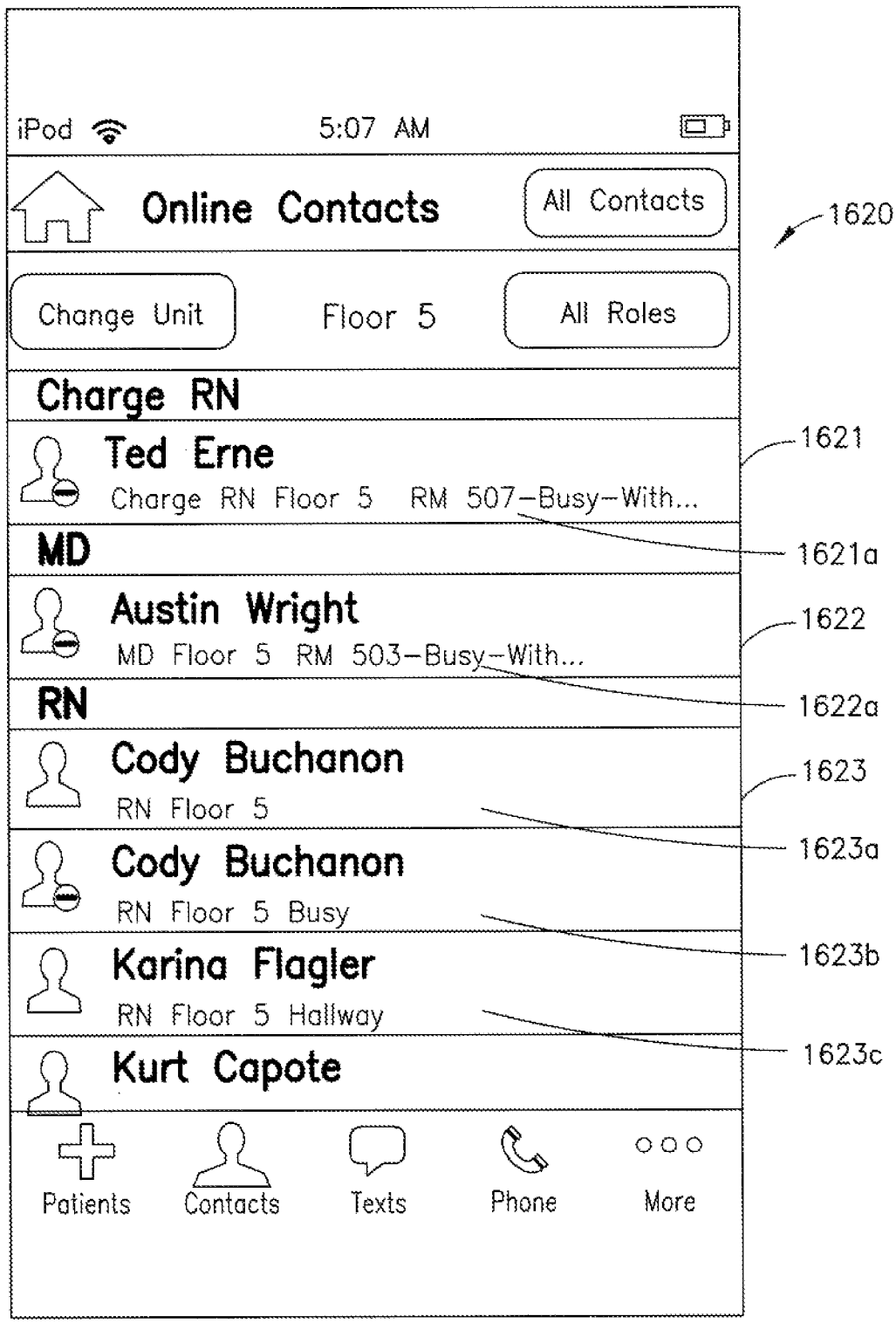
FIG. 16D illustrates another exemplary interface of a real-time clinical team directory.

In another aspect of the disclosed embodiment, the real-time care team directory 115 is also represented in the form of a dynamically updated contact directory for an organization or subdivision of an organization. For example, referring now to FIG. 16D, a real-time clinical directory 1620 is shown listing the patient care team members for a subdivision (in this case, the 5$^{th}$ Floor of a patient care facility). In alternate aspects, any suitable subdivision may be represented, including, for example, the entire patient care facility or multiple facilities. As can be seen in FIG. 16D, the real-time clinical directory 1620 may be dynamically generated and grouped according to patient care team member functional groups in addition to location. For example, the real-time clinical directory 1620 is into different job roles/functional groups (for instance, Charge RNs 1621, MDs 1622 and RNs 1623). The different job roles/functional groups 1621-1623 may include a listing of relevant patient care team members along with their resolved locations 1621a, 1622a, 1623a-c).

The enhanced patient care team 1601 may also be leveraged for simplifying the sharing of patient care data based on the resolved proximities of mobile devices 16c-l. For instance, relevant patient care data associated to a patient care process may be automatically shared among the enhanced patient care team 1601 so that the patient care team members associated with a patient care process and are in proximity to location(s) associated with the patient care process will have simplified access to the patient care data as they are facilitating and effecting the patient care process. The patient care data may include, for instance, patient laboratory results, patient data, patient medical histories, radiology data, prescription data or any other suitable patient data used in the patient care context.

The enhanced patient care team 1601 may also allow for simplified communications, notifications and alerts based on resolved the proximities of mobile devices 16c-l. These communications may include, for instance, enhanced asynchronous secure texting or messaging, enhanced paging, enhanced notifications, enhanced alerts, or enhanced voiced communications. In other aspects, any suitable means of communications which may be enhanced by proximity information may be facilitated. For example, enhanced asynchronous secure texting may be possible based on the enhanced patient care team 1601 and updated patient care team 1602. The enhanced asynchronous secure texting may not necessarily be directed to any particular patient care team member, but instead to the enhanced patient care team

1601. Thus, the asynchronous secure messaging will be routed to members of the enhanced patient care team 1601 based on their respective resolved proximities. For example, a member of the enhanced patient care team 1601 may send a communication to all of the other members of the enhanced patient care team 1601. The communication will be automatically and dynamically routed by the system backend 11 to the members of the enhanced patient care team 1602 within proximity to predetermined location(s) related or bound to the given patient care process without further action by the communication sender. In one aspect, the messages may be further dynamically routed by system backend 11 according to proximity to the message sender—that is, the parties closest in proximity will receive the messages first, before the message is propagated to members of the enhanced patient care team 1601 further away from the message sender. In alternate aspects, the messages may be sent to all members of the enhanced patient care team 1601 substantially at the same time. In the event that communications are ignored or not read, the system backend 11 may further escalate the messages based on the enhanced patient care team 1601, for example, by escalating the messages to other members of the enhanced patient care team 1601 based on their proximity to predetermined locations related or bound to the given patient care process ensuring that someone within the enhanced patient care team 1601 will be able to get crucial communications and data. In an aspect of the disclosed embodiment, this dynamic routing may also be available for voice communications—for example, voice over IP (VOIP) communications. The enhanced patient care team 1601 and 1602 may also help improve alerts and notifications between all parties of the enhanced patient care team 1601. For example, notifications and alerts related to a patient care process can be pushed along as it is being propagated between the members of the enhanced patient care team 1601 within proximity to the predetermined location(s) related or bound to the given patient care process. If a member of the enhanced patient care team 1601 does not respond to the alerts or notifications, the alert or notification may be pushed or escalated to additional members of the enhanced patient care team 1601 by the system backend 11. This may be accomplished by, for instance, expanding the range of the predetermined location(s) related or bound to the given patient care process to reach more patient care team members. In one aspect of the disclosed embodiment, the enhanced patient care team 1601 and updated patient care team 1602 may also allow for discrimination and filtering of communication type and content according to proximity to the predetermined location(s) related or bound to the given patient care process.

The enhanced patient care team 1601 and updated patient care team 1602 may also allow for grab and go activation of mobile devices 16 for busy clinicians. Where the system backend 11 is aware of proximity and locational data for each mobile device 16 and is also aware of which patient care team members are working and which are about to start, the system backend may automatically activate mobile devices 16 for incoming patient care team members. This simplified or substantially automated activation of mobile devices 16 may be based on proximity of the mobile devices 16 to a predetermined location(s) related or bound to the given patient care process. For instance, where within a predetermined location(s) related or bound to the given patient care process, the system backend 11 may update the enhanced patient care team 1601 to reflect certain patient care team members leaving or logging out of their mobile devices 16. This may occur when, for instance, certain patient care team members leave the area as their duty shift ends. In this situation, the system backend 11 may automatically activate and login mobile devices 16 for patient care team members who are arriving or starting their duty shift based on proximity information. This automatic login based on proximity information may be used in conjunction with the automated login system described in Automated Login Initialization On Detection of Identifying Information (hereinafter "Quick Launch") as described in U.S. patent application Ser. No. 13/616,483 filed on Sep. 14, 2012, the disclosure of which is incorporated by reference herein in its entirety. This automated login system may facilitate a more efficient operation of patient care processes.

Figure 16E:
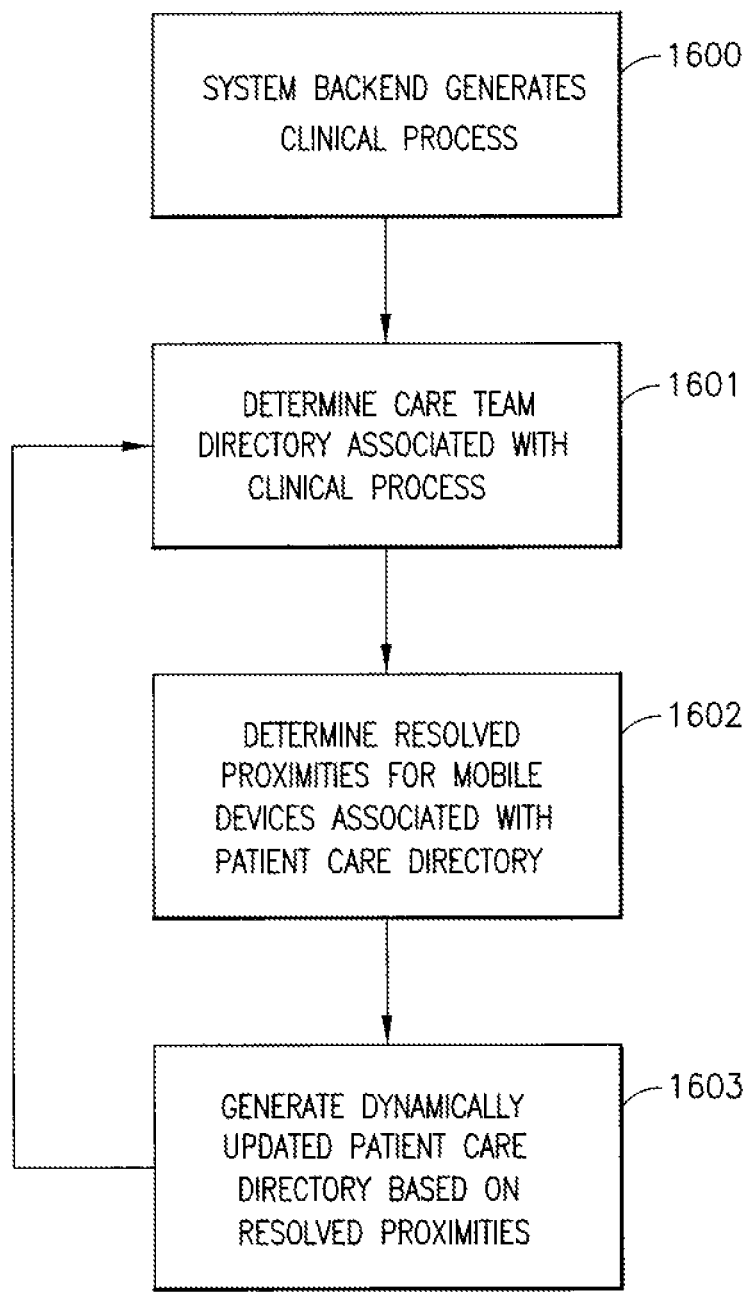
FIG. 16E illustrates an exemplary flow chart of the operation of the system.

Referring now to FIG. 16E, a block diagram illustrating the enhancement of a patient care team is shown. At block 1600, the system backend 11 is initialized and generates patient care processes. At block 1601, the system backend determines the patient care team members associated with a patient care process. At block 1602, the system backend determines the resolved proximities for the patient care team members associated with a patient care process. As noted above, this is accomplished by enabling the mobile devices 16c-k to resolve their respective relative proximities based on the beacons 15c-f and sending this information to the system backend 11. At block 1603, the system backend 11 generates enhanced patient care teams 1601 based on the resolved proximities of the mobile devices 16c-k. The enhancements are substantially similar to those described above. After the enhanced patient care team 1601 is generated by the system backend, the system backend 11 may return to block 1601 and repeat the process to generate updated patient care teams 1602.

Figure 17:
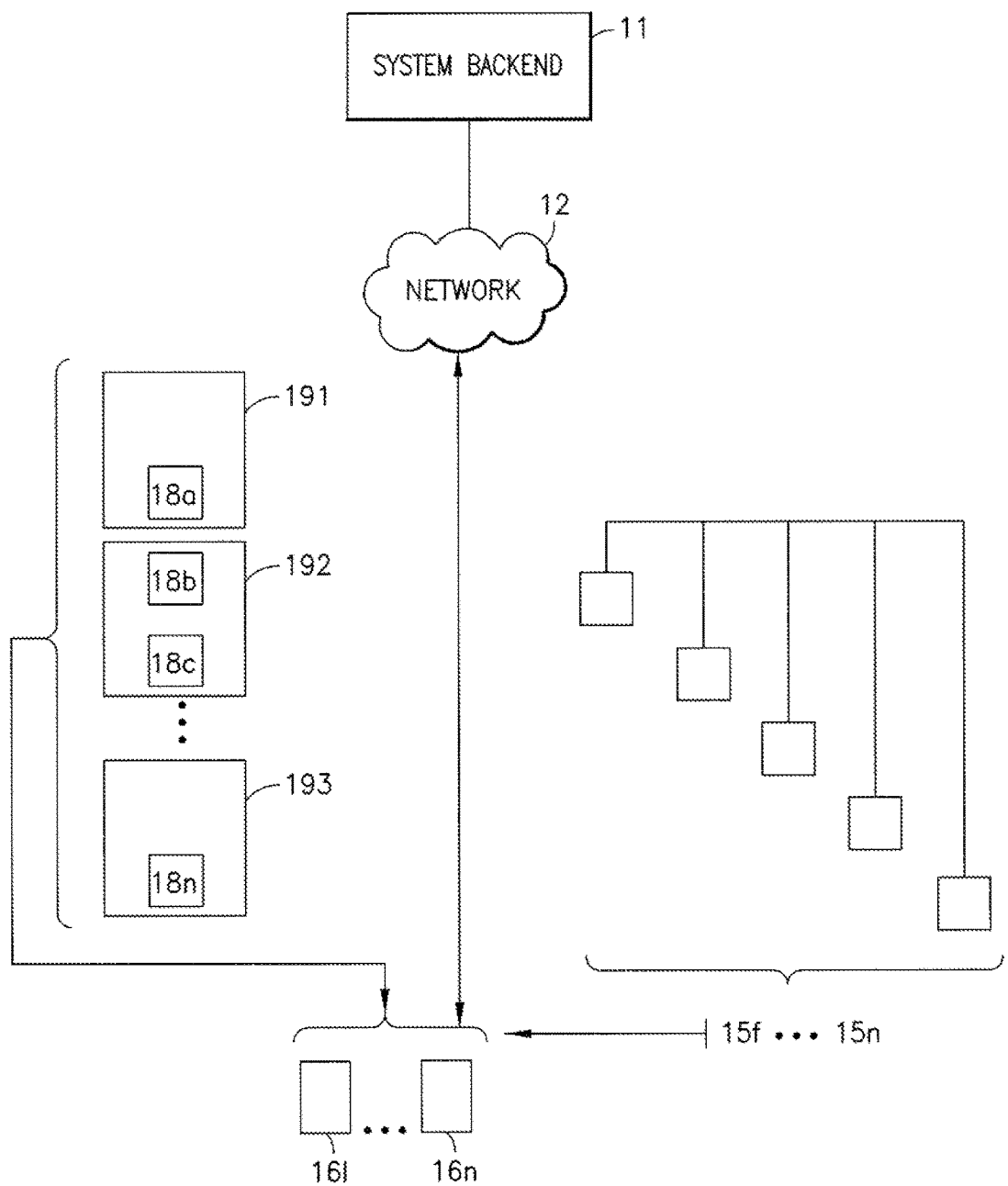
FIG. 17 illustrates a schematic representation of an overview of the system for dynamically tracking a patient care asset.

Referring now to FIG. 17, beacons 15 may also define a system for substantially real-time asset tracking for moveable assets within a patient care facility. This may be accomplished by a process known as "crowd sourcing." Crowd sourcing allows for large tasks to be performed by leveraging a "crowd" (i.e. a group) of people to perform smaller tasks collectively to contribute to the larger task. In this case, a number of mobile devices 16l-n may enable a substantially real-time and passive tracking of moveable assets based on proximity information detected by mobile devices 16 without a dedicated asset tracking system. This system for asset tracking feature is coincident with providing enhanced patient care team based on resolved proximities. In FIG. 17, the backend 11, network 12, beacons 15f-n, mobile devices 16l-n may substantially correspond to system backend 11, network 12, beacons 15 and mobile devices 16 as previously described. Further, FIG. 17 includes moveable assets 18a-n. Moveable assets may be, for example, medical equipment, gurneys, IV stands or any other equipment within a patient care facility that is moveable (except for consumable supplies like bandages and syringes). Generally, moveable assets 18 are often durable equipment. Patient care facilities often have many pieces of moveable assets comprising of expensive medical equipment and there is a need for a simple way to track the movement of the moveable assets 18a-n. Each of the moveable assets 18a-n may also have their own low energy beacon similar to those of beacons 15. Each of the beacons on the moveable assets 18a-n are differentiable and are distinct from each other to allow for identification of each moveable asset 18a-n.

Referring still to FIG. 17, as mobile devices 16l-n (which, as noted, is associated with a patient care team member) moves within a patient care facility, the mobile devices 16l-n are able to determine and resolve its relative proximity based on the beacons 15f-n of the low energy beacon array. By leveraging the resolved proximity of the mobile devices 16*l-n* to beacons 15*f-n*, the system backend 11 may be able to determine a relative location within a patient care facility for each mobile devices 16*l-n*. Further, the mobile devices 16*l-n* may also detect proximity to beacons of moveable assets 18*a-n* as the moveable assets 18*a-n* are moved around the patient care facility. These moveable assets 18*a-n* may be further subdivided into different asset groups 190, 191, 192. These different asset groups 190, 191, 192 may be comprised of different types of moveable assets 18*a-n*. The mobile devices 16*l-n* may pass information related to detected moveable assets 18*a-n* along to the system backend 11. The system backend 11 may be able to dynamically, and in substantially real time, track the movement of the moveable assets based on the detected proximities from the mobile devices 16*l-n*. This allows for a substantially real-time and dynamic asset tracker without devoting an active tracking system for the moveable assets 18*a-n*. Thus, the asset tracking aspect of the system may be performed passively, and by the "crowd" as each patient care team member passes by the moveable asset 18*a-n*. Further, where the mobile device 16 may be able to determine its relative proximity to moveable assets 18*a-n*, system backend 11 may use the detected proximities for moveable assets 18*a-n* from many mobile devices 16*l-n* to dynamically determine an accurate position for each moveable asset 18*a-n*. For instance, the system backend 11 may use signal triangulation from multiple mobile devices 16*l-n* to pinpoint the relative proximity of a particular moveable asset 18*a-n*. The system backend 11 may also use the detected proximities of moveable assets 18*a-n* from multiple mobile devices 16*l-n* to enable error correction. For instance, system backend 11 may take the detected proximities for one moveable asset 18*a* from multiple mobile devices 16*l-n* to correct for a false signal, a signal reflection or floor bleed through from one of the mobile devices 16*l-n*.

Figure 17A:
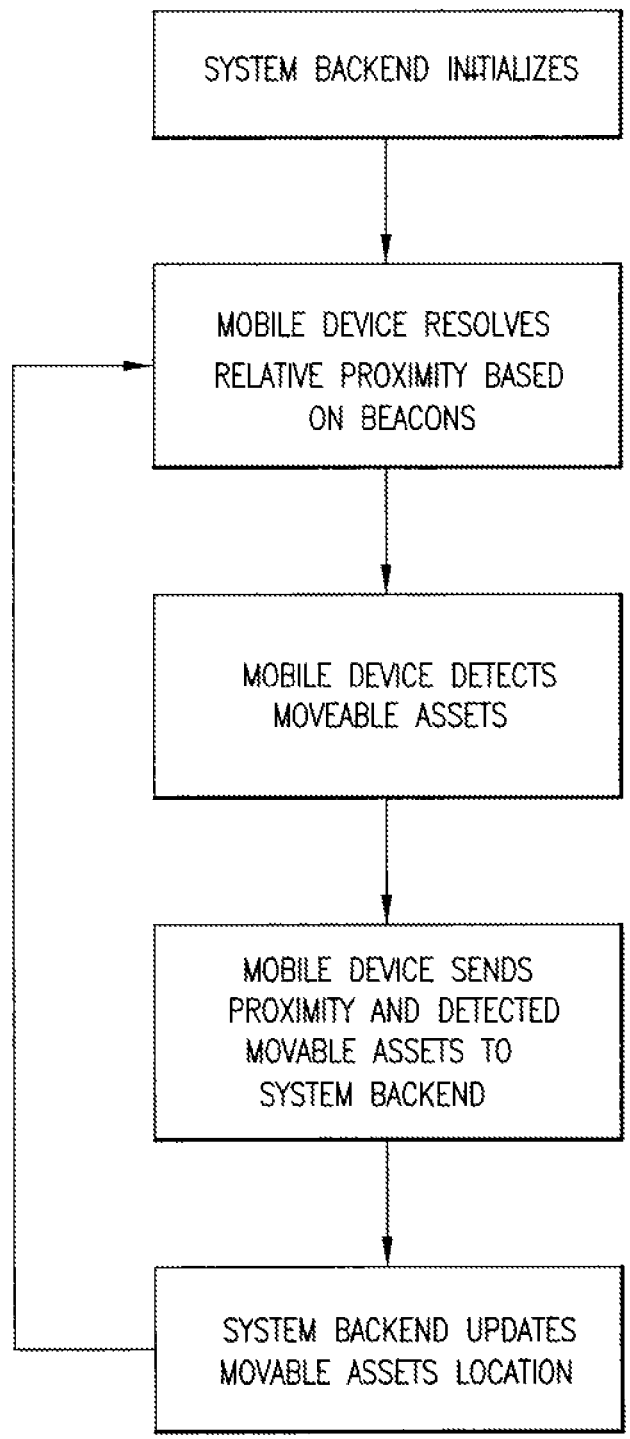
FIG. 17A illustrates an exemplary flow chart of the operation of the system.

Referring now to FIG. 17A, a block diagram illustrating the asset tracking system for moveable assets 18*a-n* is shown. At block 1700, the system backend is initialized. At block 1701, the mobile devices 16*l-n* resolve their relative proximities based on low energy beacons 15*f*-15*n*. At block 1702, the mobile devices 16*l-n* further detects moveable assets 18*a-n*. At block 1703, the mobile device 16*l-n* sends the resolved relative proximity and detected moveable assets 18*a-n* to the system backend 11. At block 1704, the system backend updates the locations for the moveable assets 18*a-n* based on the resolved relative proximities of the mobile devices 16*l-n* and the detected moveable assets 18*a-n*. After the location is updated, the system backend 11 may return to block 1701 and repeat the process to continuously update the locations of the moveable assets 18*a-n*.

It should be noted that the Beacons 15 may be used in additional uses beyond merely localization. For instance, in one alternate aspect, the Beacons 15 may be used to facilitate a substantially one-step or simplified login procedure. This may be similar to the simplified login procedure described in U.S. patent application Ser. No. 13/616,483 filed on Sep. 14, 2012, the disclosure of which was incorporated by reference herein in its entirety previously. For instance, in such an example, the proximity of a device may be used to determine which mobile device 16 to activate or complete a login procedure. A mobile device 16 within a certain proximity may be logged in a simplified manner where the login procedure is initiated in a known proximity. Thus, the correlation between where the login procedure is initiated and where a mobile device 16 is may be used to simplify the action of login.

Figure 8:
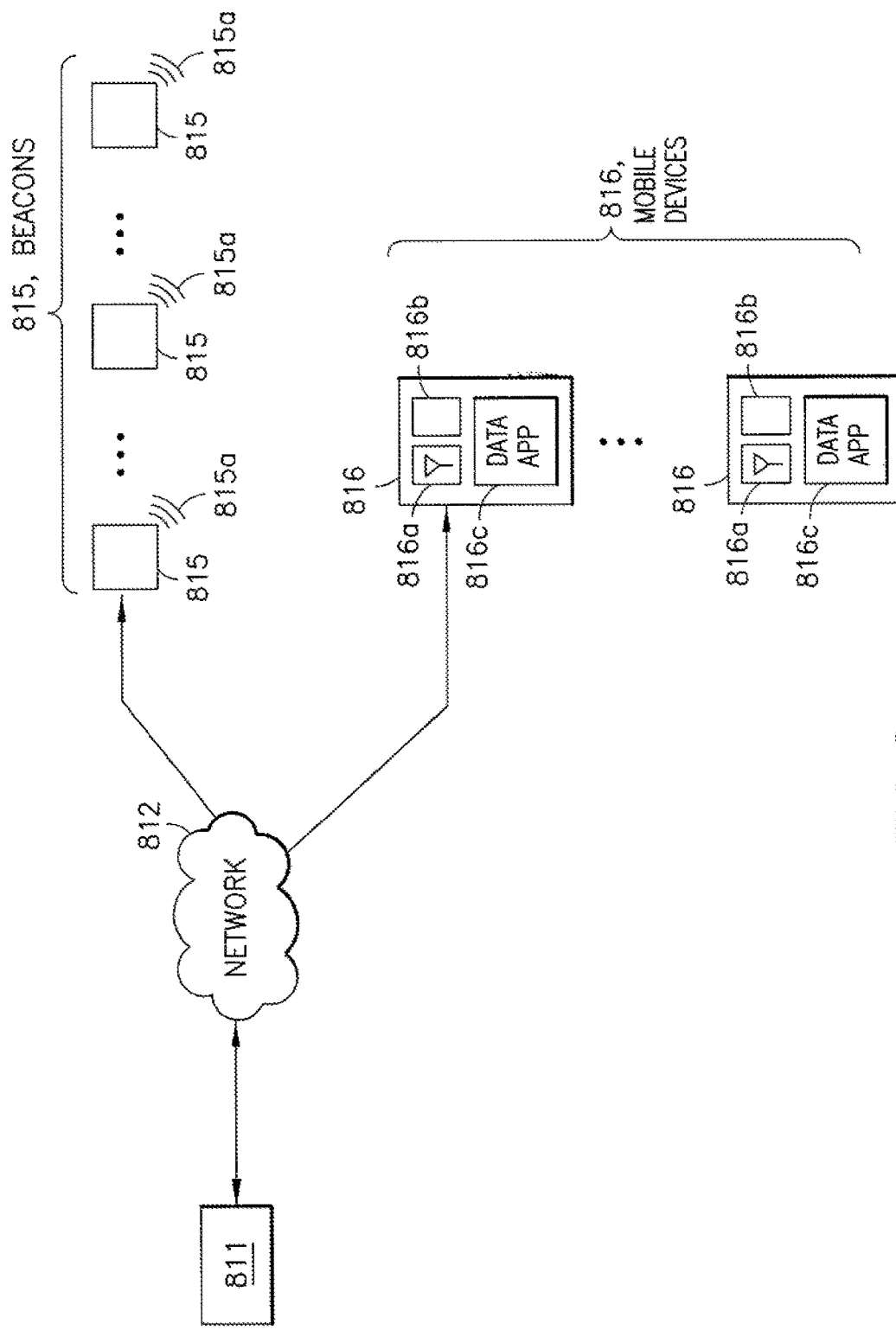
FIG. 8 illustrates a schematic representation illustrating an overview of the system utilizing a system for setting and controlling the functionalities of mobile devices.

Referring now to FIG. 8, another exemplary block illustration of the system is shown. The system shown in FIG. 8 may correspond substantially with the system shown in FIG. 1. In FIG. 8, there may be a system backend 811, which may substantially correspond with to the system backend 11. The system backend 811 may communicate over network 812, which may substantially correspond with network 12 in FIG. 1. Network 812 further may connect with a low energy beacon array comprised of beacons 815. The beacons 815 may also substantially correspond to the beacons 15 shown in FIG. 1. The beacons 815 may have a beacon transceiver 815*a* which may be substantially similar to the beacon transceiver 15*a* shown in FIG. 1. Each of the beacons 815 may emit a beacon signal with the beacon transceiver 15*a*, the beacon signal may be periodic and may contain some identifying information which may facilitate resolving proximities or localizing a mobile device. In alternate aspects, the beacon signals may also be substantially continuous instead of periodic. In yet alternate aspects, any suitable means of transmitting the beacon signal may be implemented. Additionally, the beacon signals may further include additional data. In one aspect of the disclosed embodiment, the beacon signals may include data regarding beacon status, such as battery percentage or other status messages for the beacon. In alternate aspects, the beacon signals may include any other suitable data.

Referring again to FIG. 8, a number of mobile devices 816 are shown connected to the system backend 811 via the network 812 via a communications transceiver 816*b*. The mobile devices 816's communications transceiver 816*b* may communicate over any suitable communications protocol with the network 812, including an 802.11 network (i.e. WiFi), Bluetooth, Bluetooth LE, GSM, RF or any other suitable form of network. In another embodiment, the communications transceiver 816*b* may communicate with any other suitable means include any other suitable means of communication, including through hardwired data connections or wired networking connections. The mobile devices 816 may also have a beacon signal receiver 816*a*. The beacon signal receiver 816*a* may substantially correspond with the beacon signal receiver 16*a* shown in FIG. 1. The beacon signal receiver 816*a* may be configured to receive a beacon signal. The mobile device 816 may further have a Data Application 816*c* substantially similar to the Data Application 16*c* disclosed in FIG. 1.

Each mobile device 816 may further have two operational modes. One mode may be an awake mode, where the mobile device's communications transceiver 816*b* is activated and the mobile device 816 is in a state where it is capable of receiving data from the system backend 811—for instance, alerts, notifications or clinical processes related to a clinical task. The mobile device 816 may also have a sleep mode where the mobile device's communication transceiver 816*b* is deactivated and the mobile device 816 is no longer in a state where it is capable of receiving data from the system backend 811. This may be, for instance, activated after a predetermined period of time, specifically during periods of inactivity by the device. Certain mobile devices may have features or operating system where the device may be sent into a sleep mode to preserve battery. However, this may influence the ability of the mobile device 816 from receiving necessary data from the system backend 811 such as alerts, notifications and clinical tasks.

Figure 9:
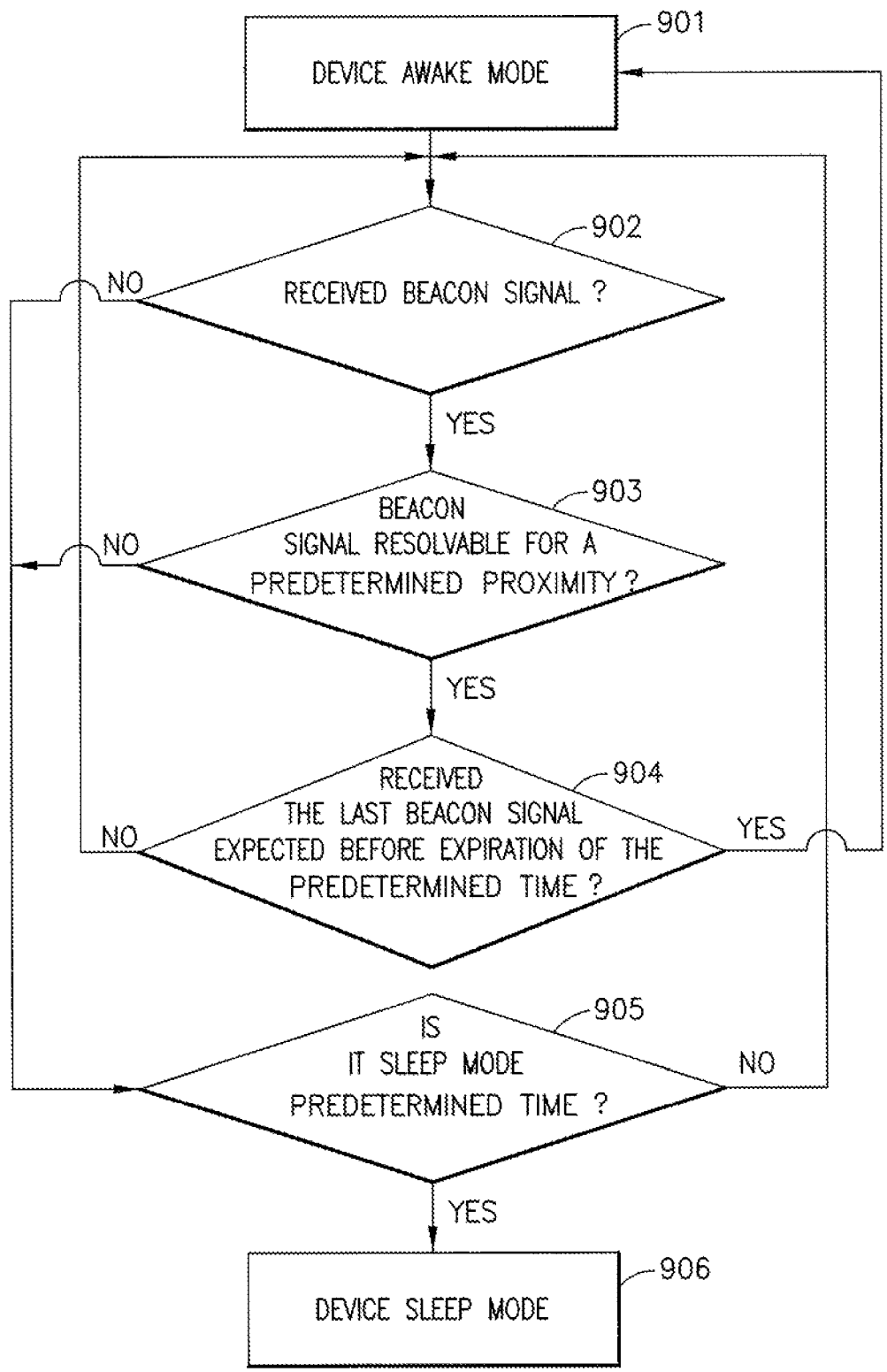
FIG. 9 illustrates another exemplary flowchart of the operation of the system.

Referring to FIG. 9, a flowchart diagram illustrating a means of preserving system readiness is shown. At block 901, a mobile device 816 is in an awake mode where the communications transceiver 816*b* is activated and the mobile device 816 is in a state to receive alerts, notifications or clinical tasks. At block 902, the mobile device 816 determines whether a beacon signal was received by the mobile device 816. The mobile device 816 may receive this beacon signal by means of, for instance, a beacon signal receiver. In one aspect of the disclosed embodiment, this may include a Bluetooth Low Energy transceiver, but in alternate embodiments, any suitable beacon signal receiver may be used. If a beacon signal was received at block 902, the mobile device 816 may determine whether it can resolve its proximity relative to a predetermined location based on the beacon signal at block 903. In one aspect of the disclosed embodiment, this may involve resolving the proximity of the mobile device 816 based on the beacon signal and determining whether the beacon signal indicates that the mobile device 816 is within a predetermined location. For example, the predetermined location may be a hospital or a section of a hospital in a medical context that a particular caretaker or nurse is assigned to work in. If a nurse or caretaker is assigned to ward A, a detected beacon signal that resolves proximity to a beacon in or near ward B would mean that the mobile device is not proximate to the predetermined location. If the beacon signal does resolve to being proximate relative to the predetermined location, then the flow continues to block 904 where the mobile device 816 determines whether the last beacon signal expected before the expiration of a predetermined period of time. The predetermined time, in this case, may be derived from the predetermined period of time that it takes for a mobile device 816 to enter a sleep mode. Specifically, this predetermined time may be less than the sleep mode predetermined period of time so that the mobile device may be still in the awake mode. Where the mobile device 816 determines that it is the last beacon signal expected before the expiration of the predetermined period of time (i.e. because the expiration of the predetermined period of time may occur between beacon signals), the mobile device 816 may return the flow to 901, where the awake mode is maintained. If, however, at block 904, it is not the predetermined time, then the flow returns to block 902 and repeats until the predetermined time is satisfied. If, in the case of either block 902 or block 903 that the beacon signal is not received or the resolved proximity is not proximate to the predetermined location, then the flow goes to block 905 where it is checked whether the predetermined period of time needed to go into sleep mode has been reached. If it has, then the flow progresses to block 906 where the mobile device 816 enters the sleep mode and the communication transceiver is deactivated. If it has not, then the flow returns to block 902 from block 905 and the query flow begins again.

It should be noted that whenever the conditions in block 904 where it is determined that a predetermined time is satisfied may include additional actions such as sending along the status of a beacon which was transmitted with the beacon signal as disclosed above. As previously noted, the beacon signal may include status information such as battery percentage or other suitable beacon status. The predetermined action may include the mobile device 816 passing the beacon status information to the system backend 811. The predetermined action may further include, for instance, passing along a mobile device readiness signal to the system backend 811. For instance, this may be a "heartbeat" sent to the system backend 811 so that the system backend 811 knows the availability of the mobile device to receive data such as alerts, notifications or clinical process. The predetermined action may further include passing along a status of the mobile device 816 to the system backend 811. In alternate aspects, any suitable predetermined action may be performed.

Figure 10:
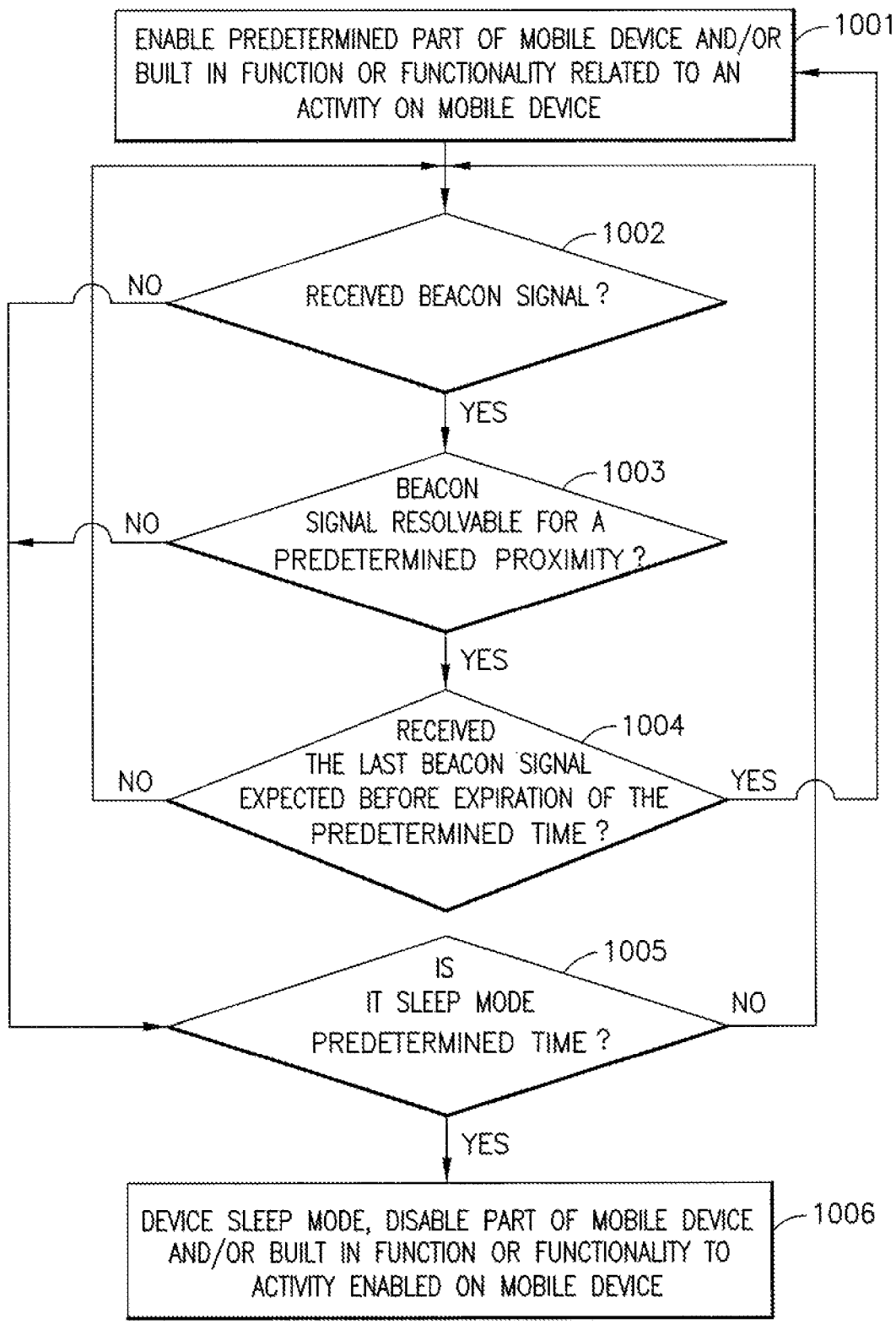
FIG. 10 illustrates another exemplary flowchart of the operation of the system.

Referring now to FIG. 10, a flowchart diagram illustrating a device proximity-based control of a predetermined part of a mobile device and/or a built in function or functionality related to an activity is shown. In certain aspects of the disclosed embodiment, a mobile device's proximity to a beacon may affect or augment the built in functionalities of a mobile device or a functionality of a mobile device related to an activity or the functions and operation of a predetermined part of a mobile device. For instance, in a medical context, for example a hospital or a healthcare clinic, a built in function or a functionality of the mobile device related to an activity may behave differently according to whether the mobile device 816 is proximate to a beacon. For the purposes of this application, a built in function or a functionality of the mobile device related to an activity may be substantially similar to the built in functions as described in SYSTEM FOR SETTING AND CONTROLLING FUNCTIONALITIES OF MOBILE DEVICES, U.S. Provisional Patent Application 61/939,104 filed on Feb. 12, 2014, and U.S. patent application Ser. No. 14/621,281, filed on Feb. 12, 2015, the disclosures of which were incorporated by reference herein in their entirety previously. The built in functions may relate to photographic, videographic or multimedia functions of the mobile device 816, however in other aspects, any other suitable built in functions may be used. Similarly, the functionality of the mobile device related to an activity may be similar to a functionality of the mobile device related to a specific clinical process as substantially described in U.S. Provisional patent application 61/939,104.

Referring again to FIG. 10, at block 1001, a predetermined part of a mobile device, and/or a built in function or functionality related to an activity on a mobile device 816 is enabled. In this mode, the mobile device 816 allows for certain built in functions or functionality related to an activity (i.e. a specific clinical process) or some predetermined part of a mobile device 816 to be enabled and accessible by a user of the mobile device 816. At block 1002, the mobile device 816 may determine whether a beacon signal is detected by the mobile device 816. If a beacon signal is detected by the mobile device, the flow proceeds to block 1003 where the mobile device 816 may be configured to determine whether the mobile device 816 can resolve proximity to a beacon 815 according to the beacon signal and determine the proximity relative to a predetermined location. If the mobile device 816 can determine that it is in proximity to a predetermined location (for instance, a specific hospital), then the flow goes to block 1004 and the mobile device 816 may determine whether it is the last beacon signal expected before the expiration of a predetermined time. The predetermined time may be derived from the sleep mode predetermined period of time that the mobile device 816 may enter into a sleep mode form an awake mode. In one aspect of the disclosed embodiment, the predetermined time may be any suitable period of time less than the sleep mode predetermined period of time. If the predetermined time was reached at block 1004, the flow returns to block 1001 and the steps of inquiry begins again.

However, if no beacon signal is detected by the mobile device 816 at block 1002 or if the mobile device 816 cannot resolve its proximity based on a beacon signal at block 1003 then the flow proceeds to block 1005, where the mobile device 816 may determine whether a sleep mode predetermined period of time is reached. If the sleep mode period of time is reached, then the mobile device may enter a sleep mode at block 106 where the predetermined part of the mobile device and/or built in functions or functionality related to an activity is disabled on the mobile device 816. This may be done, for instance, by the mobile device 816 itself, but it may also be performed by a command or other instruction from the system backend 811. For instance, the mobile device 816 may report that the it no longer detects a beacon signal and may send this information to the system backend 811, whereupon, the system backend 811 may command the mobile device 816 to disable the built in functions or functionalities related to an activity being displayed on the mobile device 816. In alternate aspects, the system backend 811 may also alter the information being sent to the mobile device 816 upon receiving information that the mobile device 816 does not detect a beacon signal. In yet other aspects, any suitable means by which the built in function or functionality related to an activity is disabled may be used. If, however, the sleep mode predetermined period of time has not yet been reached, then the flow returns to block 1002 and the query begins again.

This process may be described by means of an example. If a user of the mobile device 816, for instance, a physician based at predetermined hospital, is at the predetermined hospital location, the mobile device 816 may enable all built in functions and functionalities related to an activity (for instance a clinical process related to the treatment of a patient, in a medical context) may be enabled. In this case, the physician may be able to take advantage of the full functionalities and built in functions of the mobile device within the data application. For example, a physician may be able to take photos or videography of a patient for the clinical process related to that patient. This information may be used, for instance, for diagnosis or recordkeeping purposes. The physician may also be able to pull up various data related to the clinical process associated with the patients— for instance, billing or clinical charts or any other suitable form of data related to the clinical process. While a physician is in the premises of the predetermined hospital, the mobile device 816 being used by the physician may be detecting the beacon signals of the various low energy beacons 815 distributed around the hospital in the low energy beacon array 815. The mobile device 816 may, thus, resolve its proximity to one or more low energy beacons according to the beacon signals received by the mobile device 816 and determine that it is still in proximity to a predetermined region, in this case, the predetermined hospital. However, if the physician leaves the premises of the hospital, the mobile device 816 may no longer detect the beacon signals from the low energy beacons 815 of the hospital's low energy beacon array. Thus, the mobile device 816's built in functions and functionalities related to the clinical process associated with the physician may be disabled. Thus, the physician's mobile device 816 may no longer be able to access all built in functions, for instance, the ability to take photographs, videography or access the multi-media functions of the mobile device through the data application, nor would the physician's mobile device 816 be able to access the various data related to the clinical process associated with the patient. This helps protect confidentiality and lessens the ability for information to be accessed when outside of a predetermined location or premises. Alternately, if the physician is in a different hospital with a low energy beacon array and other beacons, if the mobile device 816 used by the physician can determine that it is not in proximity to a predetermined region (i.e. the original predetermined hospital), the built in functions and functionality related to activities (i.e. the clinical process) may also be disabled or otherwise inaccessible to the physician through the mobile device 816 and its data application.

Figure 11:
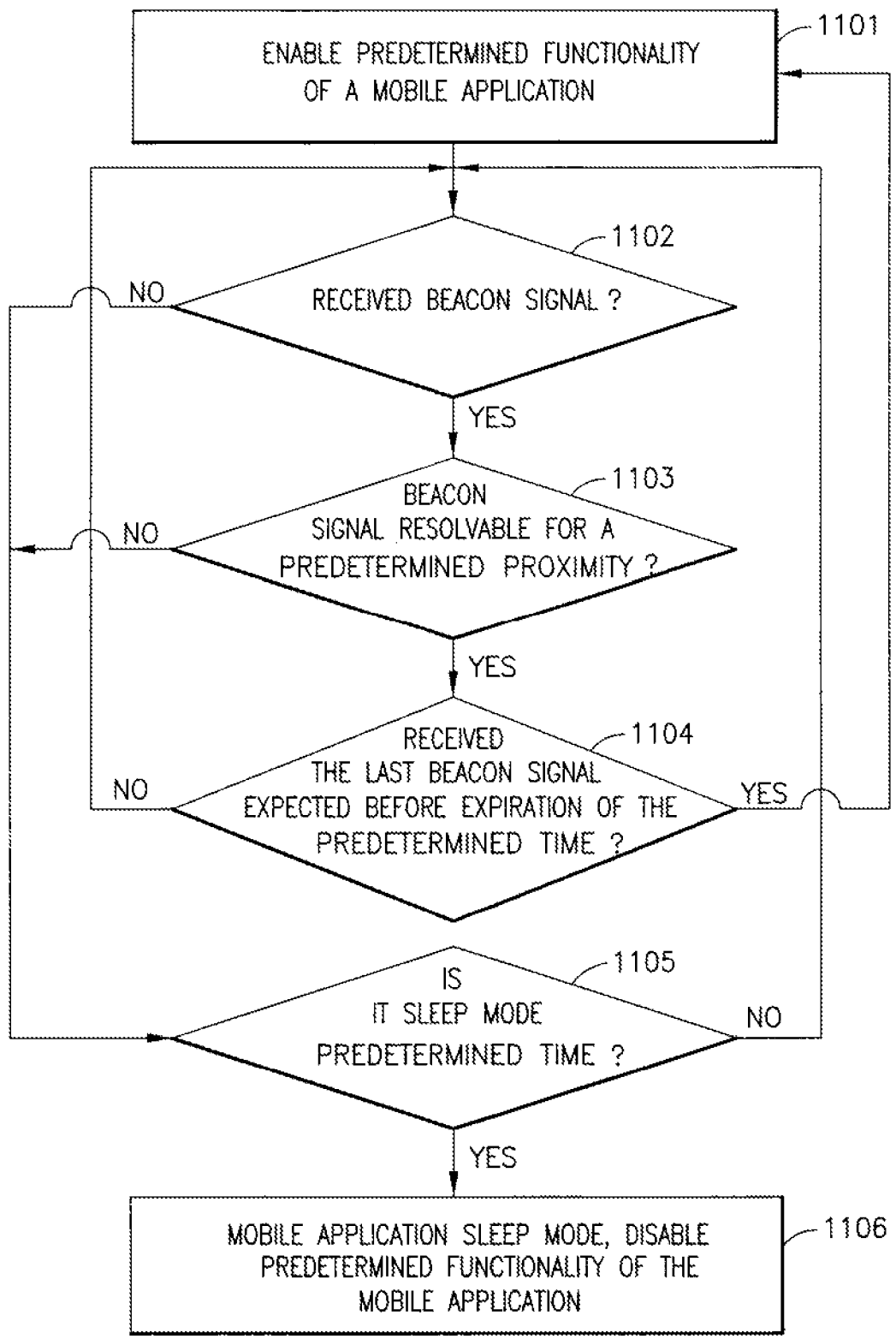
FIG. 11 illustrates another exemplary flowchart of the operation of the system.

Similarly, such a proximity-based system may also be configured to effect a change in the user interface of a mobile device 816. This may be, for instance, the user interface of the Data Application 816c shown in FIG. 8. Referring now to FIG. 11, a flowchart illustrating an exemplary proximity-based control of user interface for a mobile device 816 may be shown. At block 1101, a user interface mode related to an activity is enabled on a mobile device 816. At block 1102, the user interface mode related to an activity (i.e. clinical process) is enabled to display information related to the activity via a predetermined characteristic. For instance, the predetermined characteristic may affect the display of information on the mobile device 816's user interface mode. For instance, as substantially described in U.S. Provisional patent application 61/939,104, which was incorporated by reference in its entirety, this may be a change between a restricted user interface mode or an unrestricted user interface mode of a Data Application 816c. However in alternate aspects, any predetermined characteristic which may change some aspect of the user interface mode and, for instance, change the display of information or change the appearance or user interface options and layout may be implemented. At block 1102, the mobile device 816 may determine whether a beacon signal is detected by the mobile device 816. If there is a beacon signal detected by the mobile device 816, then the mobile device 816 may attempt to determine if the mobile device 816 may resolve its proximity to a predetermined location based on the beacon signal at block 1103. If the mobile device 816 can resolve the proximity based on the beacon signal, the flow may proceed to block 1104, where the mobile device may be determine whether it is the last beacon signal expected before the expiration of a predetermined period of time. The predetermined time may be derived from the sleep mode predetermined period of time that the mobile device 816 may enter into a sleep mode form an awake mode. In one aspect of the disclosed embodiment, the predetermined time may be derived from the sleep mode predetermined period of time, for instance any suitable period of time less than the sleep mode predetermined period of time. If it is the predetermined period of time, the flow returns to block 1101 where the process begins again. If it does not, then it returns to block 1102 and the second user interface mode related to the activity remains configured to display information related to the activity via the predetermined characteristic. If, however, at any of the blocks 1102, 1103, the inquiry fails, then the flow proceeds to block 1105, the mobile device 816 is configured to determine whether it is a sleep mode predetermined period of time. If it is, then the flow progresses to block 1106 where the first user interface mode is enabled and the predetermined functionality related to the activity is displayed via a changed predetermined characteristic. If, however, it is not the sleep mode predetermined period of time, the flow returns to block 1102 and the process of checking begins again.

It should be noted that the change in user interface based on a predetermined characteristic may be performed on a system backend, the system front end or, a hybrid system. For instance, the mobile device 816 may, if the inquiry fails at blocks 1103, 1104 and 1105, signal a system backend 811 as to the resolved proximity based on the beacon signal received by the mobile device 816. In response to a detected change in mobile device proximity, the system backend 811 may be configured to change the predetermined characteristic of the data being sent to the mobile device 816 and visible through the mobile device 816's user interface. Alternatively, in another aspect, the entire operation may be done entirely on the front-end. For instance, where a mobile device 816 may detect a change in proximity, the mobile device may be configured to change the predetermined characteristic accepted or may only accept certain data based on a changed predetermined characteristic. Alternatively, in yet another aspect, a hybrid system may be accomplished wherein the mobile device 816 may involve the mobile device 816 signaling a proximity change to the system backend 811, which then signals the mobile device 816 to change the predetermined characteristic accepted or only accept certain data based on a changed predetermined characteristic. In practical usage, the changed predetermined characteristic limits the data available on the display of a mobile device 816.

Figure 11A:
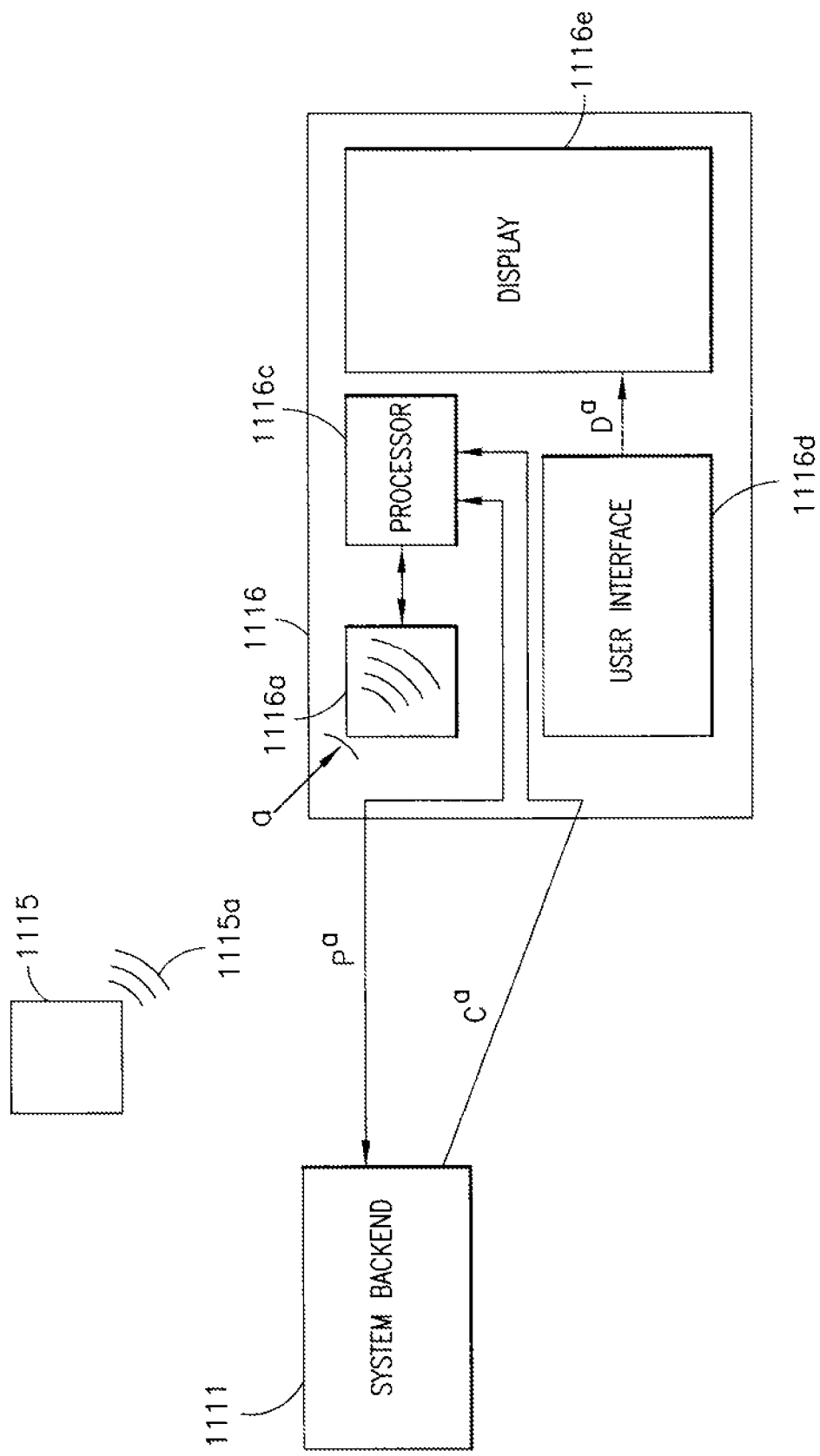
FIGS. 11A-11B illustrates an exemplary block diagram of the system.
Figure 11B:
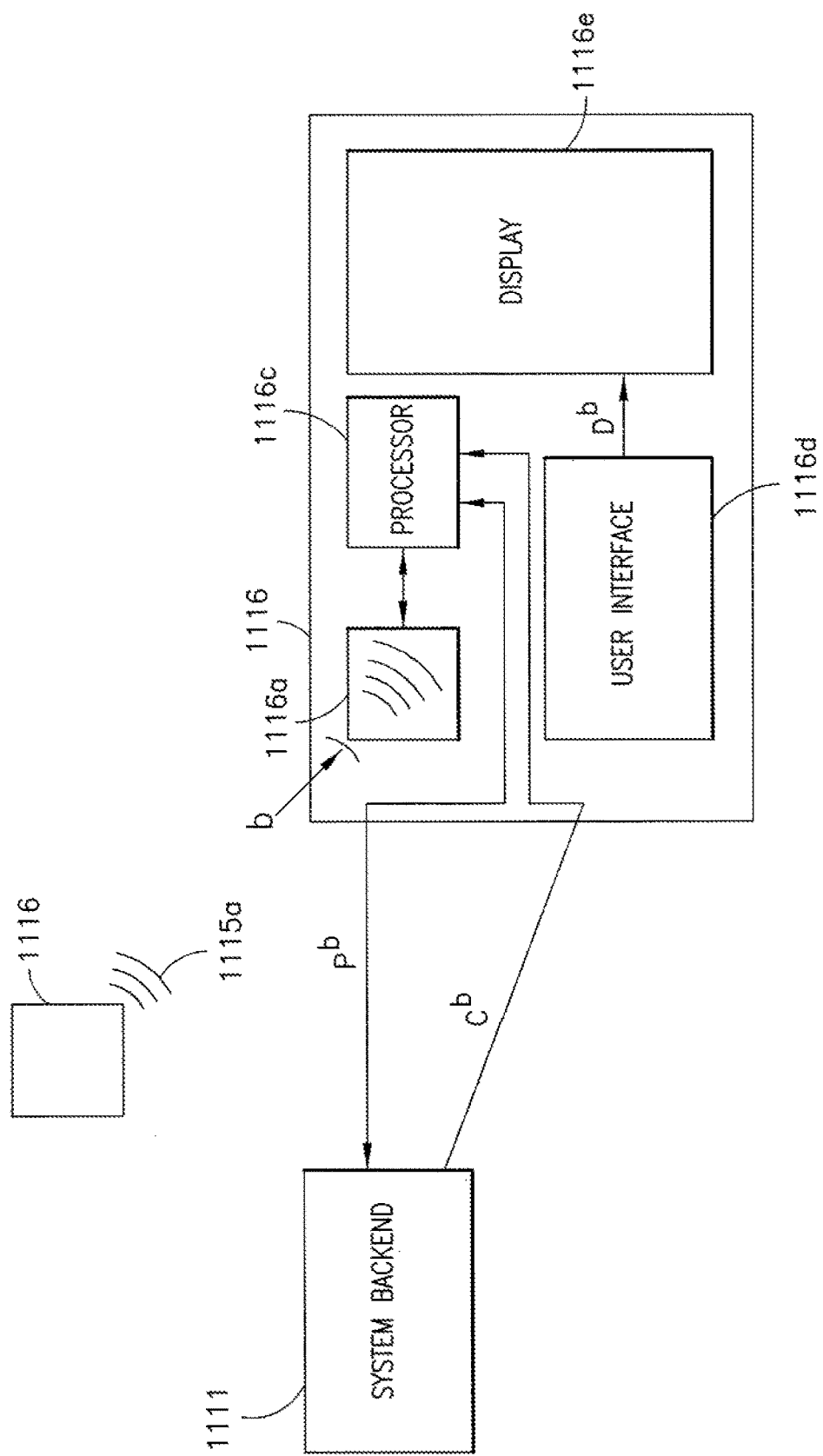

A block diagram of the system may further be shown in FIGS. 11A and 11B which may further illustrate the system described in FIG. 11. FIGS. 11A and 11B show a system backend 1111 which may be substantially similar to the system backend 11 and 811 shown in FIGS. 1 and 8. FIGS. 11A and 11B may also show a low energy beacon 1115 which may be substantially similar to the low energy beacons 15 and 815 shown in FIGS. 1 and 8, each beacon also having a beacon signal transceiver 1115a which may be similar to the beacon signal transceivers 15a and 815a shown in FIGS. 1 and 8. FIGS. 11A and 11B also show a mobile device 1116 which may substantially correspond with the mobile devices 16 and 816 shown in FIGS. 1 and 8. The mobile device 1116 may further have a beacon signal receiver 1116a, which may substantially correspond with the beacon signal receiver 16a and 816a shown in FIGS. 1 and 8. The mobile device 1116 may also have a processor 1116c, a user interface module 1116d and a display 1116e. The beacon signal receiver 1116a can communicate with the mobile processor 1116c. The mobile processor may also communicate with the user interface module 1116d which is able to generate a user interface shown on the display 1116e.

Referring now specifically to FIG. 11A, the beacon signal receiver 1116a may receive a beacon signal a received from the low energy beacon 1115 and broadcasted by the beacon signal transceiver 1115a. The beacon signal receiver 1116a may pass the beacon signal a to the processor 1116c, which may resolve its proximity based on the beacon signal a received by the beacon signal receiver 1116a. The processor 1116c may further communicate the proximity $p^a$ resolved by the processor 1116c based on beacon signal a. The proximity $p^a$ is received by the system backend 1111 which may send a predetermined characteristic $c^a$ back to the processor 1116c. The processor may receive the predetermined characteristic $c^a$ and alter some aspect of the user interface 1116d based on the predetermined characteristic $c^a$. The display $d^a$ based on the predetermined characteristic $c^a$ is then outputted and visible via the mobile device display 1116e.

Referring now specifically to FIG. 11B, the beacon signal receiver 1116a may receive a different beacon signal b received from the low energy beacon 1115 and broadcasted by the beacon signal transceiver 1115a. The beacon signal receiver 1116a may pass the beacon signal b to the processor 1116c, which may resolve its proximity based on the beacon signal b received by the beacon signal receiver 1116a. The proximity based on beacon signal b may result in a different proximity $p^b$ compared to the proximity $p^a$ shown in FIG. 11A (i.e. there was a change in the proximity resolved by the mobile device processor 1116c). The processor 1116c may further communicate the changed proximity $p^b$ resolved by the processor 1116c based on beacon signal a. The changed proximity $p^b$ is received by the system backend 1111 which may send different predetermined characteristic $c^a$ back to the processor 1116c. The processor may receive the changed predetermined characteristic $c^b$ and alter some aspect of the user interface 1116d based on changed predetermined characteristic $c^b$ so that the user interface 1116d may show a different set of data or a limited set of data according to the predetermined device. The display $d^b$ based on the changed predetermined characteristic $c^b$ is then outputted and visible via the mobile device display 1116e.

Figure 12:
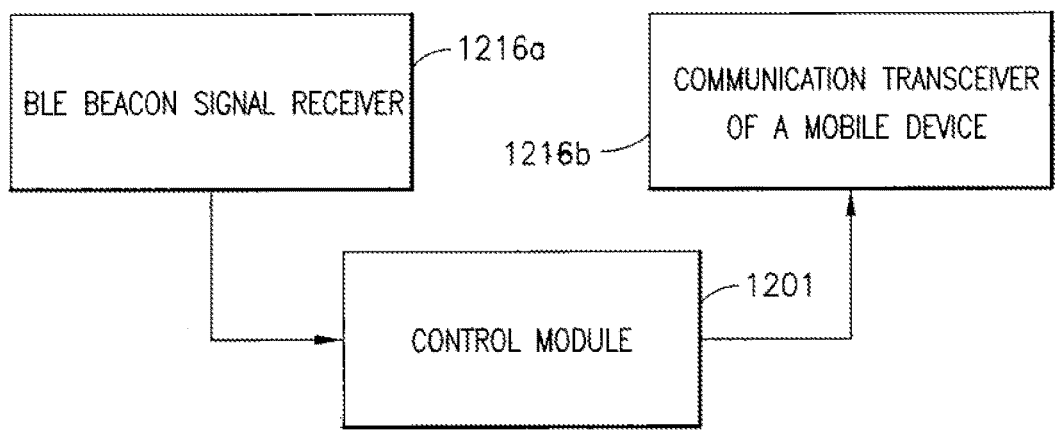
FIG. 12 illustrates another exemplary block diagram of a portion of the mobile device.

Referring now to FIG. 12, it should be noted that in conjunction to FIG. 9 there may be a system wherein there is a control module which communicatively links the Beacon signal receiver 1216a of a mobile device, which may substantially correspond with the beacon signal receiver 16a and 816a of FIGS. 1 and 8, to the communications transceiver 1216b, which may substantially correspond with the communication transceiver 16b, 816b of the mobile device 16, 816 of FIGS. 1 and 8, via the control module 1201. The control module 1201 may be configured to control the operation of the communications transceiver 1216b by performing some function—for instance, maintaining activation of the communications transceiver 1216b based on a predetermined state of the beacon signal receiver. For instance, this predetermined state may include whether a beacon signal was received by the beacon signal receiver 1216a. In alternate aspects, other suitable states may include whether a beacon signal was received by the beacon signal receiver 1216a at a predetermined time—for instance a time period less than the time a mobile device enters a sleep mode. In alternate aspects, any other suitable states may be used.

Figure 13:
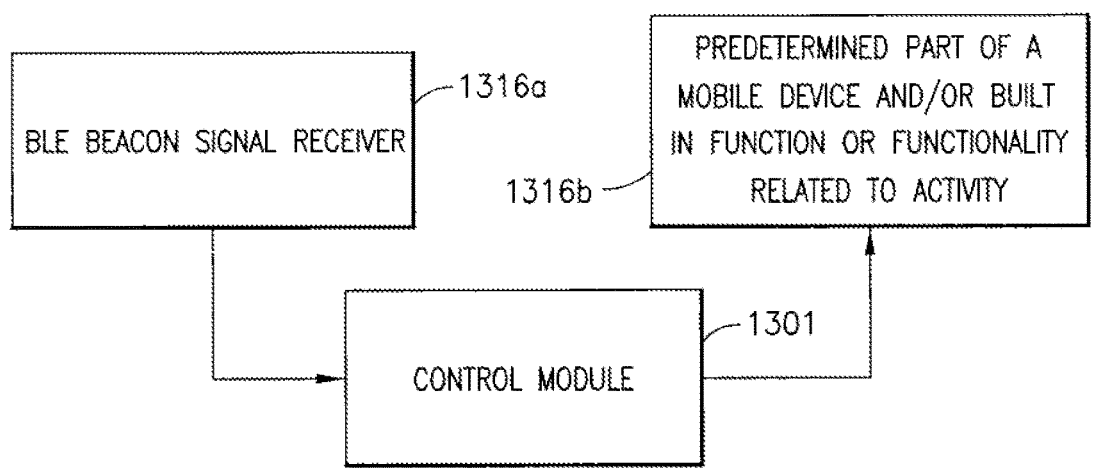
FIG. 13 illustrates another exemplary block diagram of a portion of the mobile device.

Referring now to FIG. 13, it should be noted that in conjunction to FIG. 10 there may be a system wherein there is a control module which communicatively links the Beacon signal receiver 1316a of a mobile device, which may substantially correspond with the beacon signal receiver 16a and 816a of FIGS. 1 and 8, a built in function, functionality related to an activity or a predetermined part of the mobile device 1316b, via the control module 1301. The built in function may include, for instance, any built in function of the mobile device 16, 816. For instance, this may include photography, videography or multimedia functions, but in alternate aspects, any suitable built in functions may be available. The functionality related to an activity may be any functionality related to an activity, for instance, a function related to a clinical process. This may include, for instance, data which may be presented related to a clinical process. In alternate aspects, any suitable functionality may be available. For the purposes of this application, a built in function or a functionality of the mobile device related to an activity may be substantially similar to the built in functions as described in SYSTEM FOR SETTING AND CONTROLLING FUNCTIONALITIES OF MOBILE DEVICES, U.S. Provisional Patent Application 61/939,104 filed on Feb. 12, 2014, and U.S. application Ser. No. 14/621,281, filed Feb. 12, 2015, the disclosures of which were previously incorporated by reference in their entirety. The predetermined part of a mobile device 16, 816 may be any predetermined part, including any suitable physical or software part of the mobile device. This may include software modules, but may also include mobile device 16, 816 functionalities like telephony, cameras, data connections, etc. The control module 1301 may be configured to control the operation of the built in function, functionality related to an activity or a predetermined part of the mobile device 1316b by performing some function—for instance, maintaining activation of the built in function, functionality related to an activity or a predetermined part of the mobile device 1316b based on a predetermined state of the beacon signal receiver. For instance, this predetermined state may include whether a beacon signal was received by the beacon signal receiver 1316a. In alternate aspects, other suitable states may include whether a beacon signal was received by the beacon signal receiver 1316a at a predetermined time—for instance a time period less than the time a mobile device enters a sleep mode. In alternate aspects, any other suitable states may be used.

Figure 14:
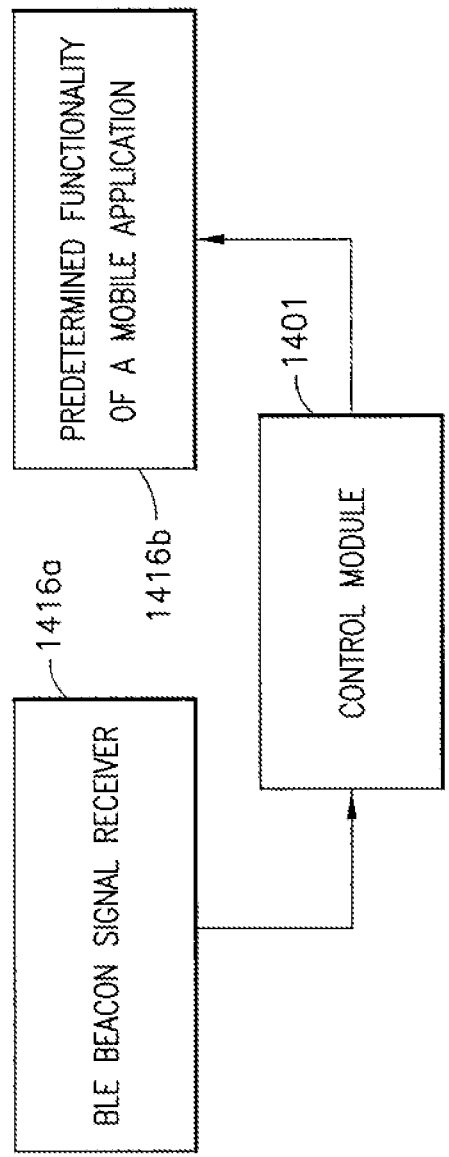
FIG. 14 illustrates another exemplary block diagram of a portion of the mobile device.

Referring now to FIG. 14, it should be noted that in conjunction to FIG. 11 there may be a system wherein there is a control module which communicatively links the Beacon signal receiver 1416a of a mobile device, which may substantially correspond with the beacon signal receiver 16a and 816a of FIGS. 1 and 8, and predetermined functionality of the mobile application 1416b, via the control module 1401. The predetermined functionality of the mobile application 1416b related to an activity may be any functionality of a mobile application, for instance, a user interface or user interface mode. This may include, for instance, data which may be presented in the mobile application. In alternate aspects, any suitable functionality may be available. For the purposes of this application, predetermined functionality of the mobile application 1416b may be substantially similar to the user interface modes as described in SYSTEM FOR SETTING AND CONTROLLING FUNCTIONALITIES OF MOBILE DEVICES, U.S. Provisional Patent Application 61/939,104 filed on Feb. 12, 2014, and U.S. application Ser. No. 14/621,281, filed Feb. 12, 2015, the disclosures of which were previously incorporated by reference in their entirety. The predetermined part of a mobile device 16, 816 may be any predetermined part, including any suitable physical or software part of the mobile device. The control module 1401 may be configured to control the operation of the predetermined functionality 1416b by performing some function—for instance, maintaining activation of the built in function, functionality related to an activity or a predetermined functionality of the mobile application 1416b based on a predetermined state of the beacon signal receiver. For instance, this predetermined state may include whether a beacon signal was received by the beacon signal receiver 1416a. In alternate aspects, other suitable states may include whether a beacon signal was received by the beacon signal receiver 1316a at a predetermined time—for instance a time period less than the time a mobile device enters a sleep mode. In alternate aspects, any other suitable states may be used.

It should also be noted that the low energy beacons 15, 815 may also be incorporated or included as part of a system referred to here for description purposes. For instance, the low energy beacons 15, 815 may also facilitate an automated login, for example in a "Quick Launch" system as described in Automated Login Initialization On Detection of Identifying Information as described in U.S. patent application Ser. No. 13/616,483 filed on Sep. 14, 2012, the disclosure of which was incorporated by reference herein in its entirety. For example, referring now to FIG. 15, a backend 11 is provided (the system described here may be generally similar to that illustrated in FIG. 1 and similar features are similarly numbered). The backend 11 may substantially correspond to the backends 11 and 811 provided in FIGS. 1 and 8. A network 12 is also provided which may substantially correspond to the networks 12 and 812 provided in FIGS. 1 and 8. A number of mobile devices 16 may be provided as well which correspond substantially to the mobile devices 16 and 816 shown in FIGS. 1 and 8. Each of the mobile devices may be connected to a docking station 23A-N with status indicators 24A-N. The docking stations 23A-N may further be connected to reader devices 21A-N which may have processors 21CA-CN and a reader 21BA-BN. Each reader device 21A-N may further have a low energy beacon 15. The low energy beacons 15 may help facilitate an automated login procedure. For instance, when a user uses the complementary identification device 22 on the reader device 21A's reader 21BA and picks up a mobile device 16 from the docking station 23A, the mobile device 16 may be able to determine its relative proximity based on the low energy beacons 15 which is part of the reader device 21A. Because, as previously noted, a mobile device 16 may use also use the low energy beacon 15 to remain in an awake mode. In the system presently described, if the mobile device 16 mobile device 16 is in a sleep mode while in the docking station 23A, then no automated login may occur. Further, in the system currently described, if no proximate beacon signal is detected by the mobile device 16, there may also be no automated login action. An automated login action may require the ability to detect and resolve a relative proximity based on a beacon signal from a low energy beacon 15. The reader device 21A may receive credential information from the complementary identification device 22, which is communicated to the login manager 114 on the backend 11. The login manager 114 may further receive information such as a resolved proximity based on the low energy beacon 15 received by a mobile device 16 which has been removed from the docking station 23A. The login manager 114 may complete the automated login operation based on the combined information between the credentials received and the received resolved proximity from a mobile device 16 to automatically log the user with the complementary identification device 22 onto the mobile device 16 that was removed from the dock. In alternate aspects, any suitable way where a low energy beacon may be used to facilitate an automated login operation may be employed. For instance, a mobile device 16 may be automatically logged in based on a resolved proximity of a low energy beacon 15 at a predetermined location. For instance, a mobile device 16 may automatically log in when it resolves its proximity as to be near a predetermined location. This may take the form of an individual's mobile device 16 automatically logging in once it enters the individual's office or other location. In other aspects, the mobile device 16 may also automatically log out unless the mobile device 16 is able to detect a proximate beacon signal. For instance, if a mobile device 16 leaves the premises of an array space, the mobile device 16 may automatically log out when no beacon signal is detected by the mobile device 16. In yet other aspects, if the mobile device 16 is returned to the docking station 23A and can resolve a proximity from the low energy beacon 15 associated with the reader 21A, the mobile device 16 may also automatically log out. In yet other aspects, any suitable automated login operation using a low energy beacon may be employed.

A first aspect of the disclosed embodiment for system for controlling process pathways is disclosed. The system having a system backend having a processor configured to manage a physical process that comprises a series of physical tasks, each with an associated physical location and at least one of which is different than another physical location of a different one of the physical tasks, each of the different physical tasks in the series corresponding to different points along an associated process pathway so that each point represents a different physical task and its location, a group of mobile devices communicably connected via a network to the system backend, each of the mobile devices having a different predetermined characteristic related to effecting at least one of the physical tasks and altering a state of the corresponding pathway point, a low energy (LE) beacon array arranged in a predetermined relationship with and differentiating between different physical task locations, and communicably connected to each of the mobile devices that is configured to resolve its proximity, from the beacon array, relative to the at least one physical task location and signal the device proximity to the backend processor. The processor is configured to register the device proximity and initiate a predetermined action associated with the state of a pathway point based on the registered device proximity.

In accordance with the first aspect of the disclosed embodiment wherein each of the mobile devices is configured to receive communications from the backend related to the process pathway.

In accordance with the first aspect of the disclosed embodiment wherein the predetermined action is registering the real time proximity of the mobile device relative to the location represented by the process pathway point.

In accordance with the first aspect of the disclosed embodiment wherein the predetermined action is selecting between sending and not sending a communication to the mobile device based on registering the mobile device real time proximity at the location represented by the process pathway point.

In accordance with the first aspect of the disclosed embodiment wherein the communication is an alarm generating signal, or a signal turning off an alarm on the mobile device.

In accordance with the first aspect of the disclosed embodiment wherein the predetermined action is escalating an alarm to another of the mobile devices based on the real time proximity of the mobile device and the other mobile device.

In accordance with the first aspect of the disclosed embodiment wherein the beacon array is a Bluetooth® low energy (BLE) beacon array.

In accordance with the first aspect of the disclosed embodiment wherein the process pathway embodies the physical process and the processor is configured to manage the process pathway changing states of the pathway point based on the registered device proximity.

In accordance with the first aspect of the disclosed embodiment wherein the action is mapping proximities of the group of mobile devices.

In accordance with the first aspect of the disclosed embodiment wherein the map defines both track and real time proximity of each of mobile device with respect to the corresponding pathway point.

In accordance with the first aspect of the disclosed embodiment wherein the action is registering a track of each mobile device proximity and real time proximity relative to the corresponding pathway point.

In accordance with the first aspect of the disclosed embodiment wherein the processor initiates the predetermined action based on registering a change in proximity.

In accordance with the first aspect of the disclosed embodiment wherein the processor initiates the predetermined action based on registering a change in proximity of more than one of the mobile devices.

In accordance with the first aspect of the disclosed embodiment wherein each mobile device has a device processor resident therein configured to resolve the proximity of the device, from the beacon array, and initiate a predetermined action based on the proximity.

A second aspect of the disclosed embodiment for a system for controlling process pathways is disclosed. The system having a network, a system backend communicably connected with the network, the backend having a processor configured to manage a physical process that comprises a series of physical tasks, each with an associated physical location and at least one of which is different than another physical location of a different one of the physical tasks, and to manage an associated process pathway embodying the physical process, each of the different physical tasks in the series corresponding to different points along the pathway so that each point represents a different physical task and its location, a group of mobile devices communicably connected to the system backend to receive communications related to the process pathway, each of the mobile devices having a different predetermined characteristic related to effecting at least one of the physical tasks and altering a state of the corresponding pathway point. The processor is configured to determine whether each of the mobile devices is available to receive a communication related to the corresponding pathway point based on proximity signals from the mobile devices with respect to the pathway point.

In accordance with the second aspect of the disclosed embodiment, the system further having a Bluetooth® low energy (BLE) beacon array communicably connected to the mobile devices.

In accordance with the second aspect of the disclosed embodiment wherein the BLE beacon array is arranged to effect mobile device proximity discrimination between different physical task locations.

In accordance with the second aspect of the disclosed embodiment wherein each of the mobile devices is configured to resolve its proximity with respect to the at least one physical task location with BLE beacon discrimination.

A third aspect of the disclosed embodiment for a system for controlling process pathways. The system having a network, a system backend communicably connected with the network, the backend having a processor configured to manage a physical process that comprises a series of physical tasks, each with an associated physical location and at least one of which is different than another physical location of a different one of the physical tasks, and to manage an associated process pathway embodying the physical process, each of the different physical tasks in the series corresponding to different points along the pathway so that each point represents a different physical task and its location, a group of mobile devices communicably connected to the system backend, each of the mobile devices having a different predetermined characteristic related to effecting at least one of the physical tasks and altering a state of the corresponding pathway point, a BLE beacon array arranged in a predetermined relationship with and differentiating between different physical task locations, and communicably connected to each of the mobile devices that is configured to resolve its proximity, from the beacon array, relative to the at least one physical task location and signal the device proximity to the backend processor. The processor is configured to register the device location and map the mobile devices, wherein the map is configured to define both proximity track and a real time proximity of each mobile device with respect to the corresponding pathway point.

In accordance with the third aspect of the disclosed embodiment wherein more than one of the mobile devices are associated with at least one common pathway point, and the processor is configured to map the associated mobile devices relative to each other and the at least one common pathway point.

In accordance with the third aspect of the disclosed embodiment wherein the processor is configured to initiate a predetermined action associated with the state of a pathway point based on the real time proximity of at least one mobile device.

A fourth aspect of the disclosed embodiment for a system for controlling a mobile device, the system having a system backend with a backend processor configured to manage an activity in a predetermined region, at least one mobile device communicably connected via a network to the backend, and having a processor and at least one built in function, or a functionality related to the activity, controlled by the processor, and a low energy (LE) beacon array arranged in a predetermined relationship with and differentiating between different locations in the predetermined region, and communicably connected to the mobile device, the processor of which is configured to resolve, from the beacon array, the device's proximity to a predetermined one of the different locations. The processor is further configured so that it disables the built in function or the functionality based on proximity to the predetermined location.

In accordance with the fourth aspect of the disclosed embodiment wherein the processor effects a change in state of the built in function between enabled to disabled upon resolution of proximity.

In accordance with the fourth aspect of the disclosed embodiment wherein the built in function is a photograph, videography or multi-media function.

In accordance with the fourth aspect of the disclosed embodiment wherein the processor is configured to signal the device proximity to the backend processor.

In accordance with the fourth aspect of the disclosed embodiment wherein the backend processor registers a change of device proximity and in response changes predetermined characteristic of data, communicated to the device and related to the device functionality, that changes the device functionality.

In accordance with the fourth aspect of the disclosed embodiment wherein in response to a change in device proximity, the backend processor sends a communication to the processor that effects a change in the state of the functionality between disabled to enabled in response to the communication.

In accordance with the fourth aspect of the disclosed embodiment wherein the processor effects a change in the state of the built in function between disabled and enabled based on a change in proximity.

A fifth aspect of the disclosed embodiment, a system for controlling a mobile device is disclosed. The system having a system backend with a backend processor configured to manage an activity in a predetermined region, at least one mobile device communicably connected via a network to the backend, and a low energy (LE) beacon array arranged in a predetermined relationship with and differentiating between different locations in the predetermined region, and communicably connected to the mobile device that is configured to resolve its proximity, from the beacon array, relative to a predetermined one of the different locations, and signal the device proximity to the backend processor, the mobile device having a mobile processor and a display, the mobile processor configured to provide, on the display, a user interface mode, related to the activity, via which predetermined data, with predetermined characteristic embodying information related to the activity, is available on the display from the backend processor. The mobile processor is configured to signal the device proximity to the backend processor, and in response to a change in the device proximity the backend processor changes the predetermined characteristic of the data available on the display.

In accordance with the fifth aspect of the disclosed embodiment wherein the changed predetermined characteristics limits the data available on the display.

A sixth aspect of the disclosed embodiment, a system for maintaining system readiness is disclosed. The system having a system backend, a low energy beacon array having at least one beacon configured to transmit a beacon signal, a group of mobile devices, each communicably connected via a network to the system backend with a communications transceiver and each mobile device further configured to receive the beacon signal and resolve a proximity relative to a predetermined location, wherein each of the mobile devices further having a sleep mode and an awake mode, where the mobile device's communications transceiver is deactivated in the sleep mode and the mobile device's communication transceiver is activated in the awake mode and the mobile device is further configured to enter the sleep mode from the awake mode in a sleep mode predetermined period of time. The mobile device is configured to receive the beacon signal and, in response to the received beacon signal and based on the resolved proximity relative to a predetermined location, the mobile device is further configured to maintain activation of the awake mode.

In accordance with the sixth aspect of the disclosed embodiment, wherein the mobile device is configured to receive the beacon signal at a predetermined period of time derived from the sleep mode predetermined period of time and in response to the received beacon signal, the mobile devices are further configured to maintain the activation of the awake mode based on the beacon signal received at the predetermined period of time.

In accordance with the sixth aspect of the disclosed embodiment, wherein the beacon signal further comprises a beacon status.

In accordance with the sixth aspect of the disclosed embodiment, wherein the mobile device is further configured to initiate a predetermined action in response to the received beacon signal.

In accordance with the sixth aspect of the disclosed embodiment, wherein the predetermined action is transmitting a signal signifying readiness to the system backend.

In accordance with the sixth aspect of the disclosed embodiment, wherein the predetermined action further comprises at least one status data of the mobile device.

In accordance with the sixth aspect of the disclosed embodiment, wherein the predetermined action further comprises the beacon status of the at least one beacon which transmitted the received beacon signal.

In accordance with the sixth aspect of the disclosed embodiment, wherein the mobile device is configured to maintain activation of the awake mode based on the received beacon signal at a second predetermined period of time.

In accordance with the sixth aspect of the disclosed embodiment, wherein the mobile device is further configured to maintain an activation of the awake mode based on the received beacon signal at the predetermined period of time derived from the sleep mode predetermined period of time.

In accordance with the sixth aspect of the disclosed embodiment, wherein the mobile device further comprises a beacon signal receiver and a control module, wherein the beacon signal receiver is communicably linked via the control module with the mobile device's communication transceiver, the control module is configured control the operation of the mobile device's communication transceiver based on a predetermined state of the beacon signal receiver and based on the resolved proximity relative to a predetermined location.

In accordance with the sixth aspect of the disclosed embodiment, wherein the control module is further configured to control the operation of the mobile device's communication transceiver by maintaining activation of the mobile device's communication transceiver based on the predetermined state of the beacon signal receiver A seventh aspect of the disclosed embodiment, a system for maintaining system readiness is disclosed. The system having a system backend, a low energy beacon array having at least one beacon configured to transmit a beacon signal, a group of mobile devices, at least one of the mobile devices communicably connected via a network to the system backend with a communications transceiver and the at least one mobile device further configured to receive the beacon signal and resolve a proximity relative to a predetermined location, wherein the at least one mobile device further having a sleep mode and an awake mode, where a predetermined part of the at least one mobile device and/or a built in function or functionality related to an activity of the at least one mobile device is deactivated in the sleep mode and the predetermined part of the mobile device is activated in the awake mode and the at least one mobile device is further configured to enter the sleep mode from the awake mode in a sleep mode predetermined period of time. The at least one mobile device is configured to receive the beacon signal, where, in response to the received beacon signal and based on the resolved proximity relative to a predetermined location, the at least one mobile device is further configured to maintain activation of the awake mode.

In accordance with the seventh aspect of the disclosed embodiment, wherein the mobile device is configured to receive the beacon signal at a predetermined period of time derived from the sleep mode predetermined period of time and in response to the received beacon signal and based on the resolved proximity relative to a predetermined location, the mobile devices are further configured to maintain the activation of the awake mode based on the beacon signal received at the predetermined period of time.

In accordance with the seventh aspect of the disclosed embodiment, wherein the mobile devices are configured to receive the beacon signal at a predetermined period of time and in response to the received beacon signal, the mobile devices are further configured to maintain the activation of the awake mode based on the beacon signal received at the predetermined period of time.

In accordance with the seventh aspect of the disclosed embodiment, wherein the beacon signal further comprises a beacon status.

In accordance with the seventh aspect of the disclosed embodiment, wherein the at least one mobile device is further configured to initiate a predetermined action in response to the received beacon signal.

In accordance with the seventh aspect of the disclosed embodiment, wherein the predetermined action is transmitting a signal signifying readiness to the system backend.

In accordance with the seventh aspect of the disclosed embodiment, wherein the predetermined action further comprises at least one status data of the at least one mobile device.

In accordance with the seventh aspect of the disclosed embodiment, wherein the predetermined action further comprises the beacon status of the at least one beacon which transmitted the received beacon signal.

In accordance with the seventh aspect of the disclosed embodiment, wherein the at least one mobile device is configured to maintain activation of the awake mode based on the received beacon signal at a predetermined period of time.

In accordance with the seventh aspect of the disclosed embodiment, wherein the at least one mobile device is further configured to maintain an activation of the awake mode based on the received beacon signal at the predetermined period of time derived from the sleep mode predetermined period of time.

In accordance with the seventh aspect of the disclosed embodiment, wherein the at least one mobile device further comprises a beacon signal receiver and a control module, wherein the beacon signal receiver is communicably linked via the control module with the at least one mobile device's communication transceiver, the control module is configured to control the operation of the predetermined part of the at least one mobile device and/or the built in function or functionality related to an activity of the at least one mobile device based on a predetermined state of the beacon signal receiver and based on the resolved proximity relative to a predetermined location.

In accordance with the seventh aspect of the disclosed embodiment, wherein the control module is further configured to control the operation of the predetermined part of the at least one mobile device and/or the built in function or functionality related to an activity of the at least one mobile device by maintaining activation of the predetermined part of the at least one mobile device and/or the built in function or functionality related to an activity of the at least one mobile device based on the predetermined state of the beacon signal receiver An eighth aspect of the disclosed embodiment, a system for maintaining system readiness is disclosed. The system having a system backend, a low energy beacon array having at least one beacon configured to transmit a beacon signal, and a group of mobile devices, at least one of the mobile devices communicably connected via a network to the system backend with a communications transceiver and the at least one mobile device further having a beacon signal receiver configured to receive the beacon signal and resolve a proximity relative to a predetermined location. The at least one mobile device further comprising a mobile application having a first user interface mode and an second user interface mode, where a predetermined functionality of the mobile application is deactivated in the first user interface mode and the predetermined functionality of the mobile application is activated in the second user interface mode and the mobile application is further configured to enter the first user interface mode from the second user interface mode in a sleep mode predetermined period of time. The mobile application further comprising a control module, where the beacon signal receiver is communicably connected to the predetermined functionality of the mobile application via the control module, the control module further configured to control an operation of the predetermined functionality based on a predetermined state of the beacon signal receiver and the resolved proximity relative to the predetermined location.

In accordance with the eighth aspect of the disclosed embodiment, wherein the control module is configured to control the operation of the predetermined functionality when the beacon signal receiver is in the predetermined state at a predetermined period of time derived from the sleep mode predetermined period of time.

In accordance with the eighth aspect of the disclosed embodiment, wherein the module is enabled whenever the mobile application is in the second user interface mode.

In accordance with a ninth aspect of the disclosed embodiment, a system for tracking physical assets within an enclosed facility is shown, the system having a system backend comprising a backend processor configured to track a physical asset location of at least one physical asset within the enclosed facility, a group of mobile devices communicably connected via a network to the system backend, a low energy (LE) beacon array arranged in a predetermined relationship with and differentiating between different physical locations within the enclosed facility, and communicably connected to each of the mobile devices that is configured to resolve its mobile device proximity to the physical locations within the enclosed facility, from the beacon array, the at least one physical asset having a low energy (LE) beacon and detectable by each of the mobile devices, where the low energy (LE) beacon associated with each of the at least one physical asset being distinct from a different low energy (LE) beacon of another of the at least one physical asset, wherein the backend processor is configured to identify the at least one physical asset and dynamically determine its physical asset location based on the resolved mobile device proximity of the at least one mobile device.

In accordance with a ninth aspect of the disclosed embodiment, wherein the backend processor determines the physical asset location of the detected at least one physical asset based on the resolved mobile device proximity of a plurality of mobile devices.

In accordance with a ninth aspect of the disclosed embodiment, wherein the backend processor dynamically updates the physical asset location of the detected at least one physical asset upon receipt of the resolved mobile device proximity and the detected at least one physical asset.

In accordance with a ninth aspect of the disclosed embodiment, wherein the backend processor is configured to receive the resolved mobile device proximity from at least one mobile device.

In accordance with a ninth aspect of the disclosed embodiment, wherein the backend processor is configured to determine and track changes in physical asset locations.

In accordance with a ninth aspect of the disclosed embodiment, wherein the backend processor is configured to dynamically update the status of the physical asset.

In accordance with a ninth aspect of the disclosed embodiment wherein the backend processor is configured to update a characteristic of the physical asset.

In accordance with a ninth aspect of the disclosed embodiment, wherein the backend processor is configured to track inventory and availability of at least one consumable asset.

In accordance with a tenth aspect of the disclosed embodiment, a system for tracking physical assets within a healthcare facility is disclosed, the system having a system backend comprising of a backend processor configured to manage a patient care process that comprises a series of patient care tasks, each with an associated location and at least one of which is different than other locations of a different one of the patient care tasks, each of the different patient care tasks in the series corresponding to different points along an associated patient care process pathway so that each point represents a different patient care task and its location; a group of mobile devices communicably connected via a network to the system backend, a low energy (LE) beacon array arranged in a predetermined relationship with and differentiating between different patient care task locations, and communicably connected to each of the mobile devices that is configured to resolve its proximity, from the beacon array, relative to the at least one patient care task location and signal the device proximity to the backend processor, a group of moveable patient care assets having a low energy (LE) beacon and communicably connected to each of the mobile devices, where the low energy (LE) beacon associated with each patient care asset is distinct from a different low energy (LE) beacon of at least another patient care asset of the group, wherein the backend processor is configured to dynamically track each patient care asset within the healthcare facility based on a detection of the at least one patient care asset's low energy (LE) beacon by at least one of the mobile devices.

In accordance with a tenth aspect of the disclosed embodiment, wherein the backend processor is configured to resolve a patient care asset location associated with the at least one patient care asset based on a resolved proximity of the at least one of the mobile devices based on the low energy beacon array.

In accordance with a tenth aspect of the disclosed embodiment, wherein the backend processor may track the patient care asset location of the detected at least one physical asset using multiple mobile devices.

In accordance with a tenth aspect of the disclosed embodiment, wherein the backend processor dynamically updates the physical asset location of the detected at least one patient care asset upon receipt of the resolved mobile device proximity and the detected at least one patient care asset.

In accordance with a tenth aspect of the disclosed embodiment, wherein the patient care asset is associated with at least one patient care task of a patient care process.

In accordance with a tenth aspect of the disclosed embodiment, wherein the backend processor is configured to update the status of the patient care process status on the patient care asset location.

In accordance with an eleventh aspect of the disclosed embodiment, a system for controlling patient care process in a healthcare facility is disclosed, the system having a system backend comprising a processor configured to define a patient care team associated with a patient care process comprising of a series of patient care tasks effected within the healthcare facility, each patient care task with an associated patient care task location within the healthcare facility; a group of mobile devices communicably connected via a network to a system backend, each mobile device being associated with and configured for use by at least one of the members of the patient care team; a low energy (LE) beacon array arranged in a predetermined relationship with and differentiating between different patient care task locations, and communicably connected to each of the mobile devices that is configured to resolve its proximity, from the beacon array, relative to the at least one patient care task location; wherein the processor is configured to dynamically enhance the patient care team by dynamically changing in real-time a predetermined characteristic of the patient care team based on the resolved proximity of each mobile device associated with each member of the patient care team.

In accordance with an eleventh aspect of the disclosed embodiment, wherein the backend processor is further configured to resolve members of the patient care team for each patient care task based on the resolved proximity of each mobile device associated with each member of the patient care team.

In accordance with an eleventh aspect of the disclosed embodiment, wherein the backend processor is configured to dynamically route communication links between team members and content links between patient care team members based on the resolved proximity of each mobile device associated with each member of the patient care team.

In accordance with an eleventh aspect of the disclosed embodiment, wherein the backend processor is configured to dynamically route asynchronous secure messaging based on the resolved proximity of each mobile device associated with each member of the patient care team.

In accordance with an eleventh aspect of the disclosed embodiment, wherein the backend processor is configured to dynamically route notifications and alerts associated with a patient care process based on the resolved proximity of each mobile device associated with each member of a patient care team.

In accordance with an eleventh aspect of the disclosed embodiment, wherein the notification and alerts are dynamically escalated by the backend processor based on the resolved proximity of each mobile device associated with each member of the patient care team.

In accordance with an eleventh aspect of the disclosed embodiment, wherein the backend processor is configured to filter access to at least one patient information associated with the patient care process based on the resolved proximity of each mobile device associated with each member of the patient care team.

In accordance with an eleventh aspect of the disclosed embodiment, wherein the backend processor is configured to filter access to at least one clinical information associated with the patient care pathway based on the resolved proximity of each mobile device associated with each member of the patient care team.

In accordance with an eleventh aspect of the disclosed embodiment, wherein the backend processor is configured to filter access to at least one laboratory information associated with the patient care process based on the resolved proximity of each mobile device associated with each member of the patient care team.

In accordance with an eleventh aspect of the disclosed embodiment, wherein the backend processor is further configured to generate a patient care process-specific patient care team directory based on the resolved proximity of each mobile device associated with each member of the patient care team.

In accordance with an eleventh aspect of the disclosed embodiment, wherein the backend processor is further configured to group each member of the patient care team according to a functional group.

In accordance with an eleventh aspect of the disclosed embodiment, wherein the dynamic change in predetermined characteristic of the patient care team is effected by filtering team members.

In accordance with an eleventh aspect of the disclosed embodiment, wherein the predetermined characteristic is a selection of the members of the patient care team forming the patient care team.

A twelfth aspect of the disclosed embodiment, the system having a system backend having a backend processor configured to define a patient clinical team associated with a patient clinical process comprising of a series of patient clinical tasks effected within the healthcare facility, each patient clinical task with an associated patient clinical task location within the healthcare facility, a group of mobile devices communicably connected via a network to the system backend, each mobile device being associated with and configured for use by at least one care member of the patient clinical team, a low energy (LE) beacon array arranged in a predetermined relationship with and differentiating between different patient clinical task locations, and communicably connected to each of the mobile devices that is configured to resolve its proximity, from the beacon array, relative to the at least one patient clinical task location. The backend processor is configured to dynamically enhance the patient clinical team by dynamically changing in real-time a predetermined characteristic of the patient clinical team based on the resolved proximity of each mobile device associated with each care member of the patient clinical team.

In accordance with a twelfth aspect of the disclosed embodiment, wherein the backend processor is further configured to resolve care members of the patient clinical team for each patient clinical task based on the resolved proximity of each mobile device associated with each care member of the patient clinical team.

In accordance with a twelfth aspect of the disclosed embodiment, wherein the backend processor resolves care members of the patient clinical team by dynamically updating a care team directory associated with each patient clinical task, the care team directory comprising one or more selectable elements, presented on each mobile device, each of the one or more selectable elements associated with each care member of the patient clinical team.

In accordance with a twelfth aspect of the disclosed embodiment, wherein the backend processor dynamically changes a state of at least one of the one or more selectable elements within the care team directory on each mobile device, the state of the at least one of the one or more selectable elements indicating availability of the associated care member of the patient care team, for each patient clinical task, based on the resolved proximity of each mobile device associated with each care member.

In accordance with a twelfth aspect of the disclosed embodiment, wherein the state of the at least one of the one or more selectable elements within the care team directory is presented to a third party user via an Application Programming Interface (API) module of the system backend.

In accordance with a twelfth aspect of the disclosed embodiment, wherein the backend processor is configured to dynamically route communication links between care members and content links between care members based on the resolved proximity of each mobile device associated with each care member of the patient clinical team.

In accordance with a twelfth aspect of the disclosed embodiment, wherein the backend processor is configured to dynamically route asynchronous secure messaging based on the resolved proximity of each mobile device associated with each care member of the patient clinical team.

In accordance with a twelfth aspect of the disclosed embodiment, wherein the backend processor is configured to dynamically route notifications and alerts associated with a patient clinical process based on the resolved proximity of each mobile device associated with each care member of a patient clinical team.

In accordance with a twelfth aspect of the disclosed embodiment, wherein the notification and alerts are dynamically escalated by the backend processor based on the resolved proximity of each mobile device associated with each care member of the patient clinical team.

In accordance with a twelfth aspect of the disclosed embodiment, wherein the backend processor is configured to filter access to at least one patient information associated with the patient clinical process based on the resolved proximity of each mobile device associated with each care member of the patient clinical team.

In accordance with a twelfth aspect of the disclosed embodiment, wherein the backend processor is configured to filter access to at least one clinical information associated with the patient clinical process based on the resolved proximity of each mobile device associated with each care member of the patient clinical team.

In accordance with a twelfth aspect of the disclosed embodiment, wherein the backend processor is configured to filter access to at least one laboratory information associated with the patient care process based on the resolved proximity of each mobile device associated with each care member of the patient clinical team.

In accordance with a twelfth aspect of the disclosed embodiment, wherein the backend processor is further configured to generate a patient care process-specific patient care team directory based on the resolved proximity of each mobile device associated with each care member of the patient clinical team.

In accordance with a thirteenth aspect of the disclosed embodiment, a system for controlling a patient clinical process in a healthcare facility, the system having a system backend having a backend processor configured to define a patient clinical team associated with a patient clinical process comprising of a series of patient clinical tasks effected within the healthcare facility, each patient clinical task having an associated patient clinical task location within the healthcare facility, the backend processor further configured to generate a care team directory for each patient clinical task, the care team directory comprising one or more selectable elements associated with one or more care members of the patient care team, a group of mobile devices communicably connected via a network to the system backend and configured to present the one or more selectable elements associated with the care team directory for each patient clinical task, each mobile device being associated with and configured for use by the one or more care members of the patient clinical team, and a low energy (LE) beacon array arranged in a predetermined relationship with and differentiating between different patient clinical task locations, and communicably connected to each of the mobile devices that is configured to resolve its proximity, from the beacon array, relative to the at least one patient clinical task location. The backend processor is further configured to dynamically update and enhance the care team directory for each patient clinical task.

In accordance with a thirteenth aspect of the disclosed embodiment, wherein the backend processor is further configured to dynamically update and enhance the care team directory by dynamically changing a state of at least one of the one or more selectable elements within the care team directory, the state of the at least one of the one or more selectable elements reflecting the availability of each care member, of the patient care team for each patient clinical task, based on the resolved proximity of each mobile device associated with each care member.

In accordance with a thirteenth aspect of the disclosed embodiment, wherein the state of the at least one of the one or more selectable elements within the care team directory is presented to a third party user via an Application Programming Interface (API) module of the system backend.*

In accordance with a thirteenth aspect of the disclosed embodiment, wherein the backend processor is configured to dynamically route communication links between care members and content links between care members based on the resolved proximity of each mobile device associated with each care member of the patient clinical team.

In accordance with a thirteenth aspect of the disclosed embodiment, wherein the backend processor is configured to dynamically route asynchronous secure messaging based on the resolved proximity of each mobile device associated with each care member of the patient clinical team.

In accordance with a thirteenth aspect of the disclosed embodiment, wherein the backend processor is configured to dynamically route notifications and alerts associated with a patient clinical process based on the resolved proximity of each mobile device associated with each care member of a patient clinical team.

In accordance with a thirteenth aspect of the disclosed embodiment, wherein the notification and alerts are dynamically escalated by the backend processor based on the resolved proximity of each mobile device associated with each care member of the patient clinical team.

In accordance with a thirteenth aspect of the disclosed embodiment, wherein the backend processor is configured to filter access to at least one clinical information associated with the patient clinical process based on the resolved proximity of each mobile device associated with each care member of the patient clinical team.

A fourteenth aspect of the disclosed embodiment, a system for controlling clinical processes, the system having a system backend having a backend processor configured to manage a clinical process that comprises a series of clinical tasks for care of a common patient, each clinical tasks having an associated location and at least one of associated location is different than another associated location of a different one of the clinical tasks, each of the different clinical tasks in the series corresponding to different selectable elements within a clinical process directory so that each selectable element represents a different clinical task and its location, a group of mobile devices communicably connected via a network to the system backend, each of the mobile devices having a different predetermined characteristic related to effecting at least one of the clinical tasks and altering a state of the corresponding selectable element within the clinical process directory, and a low energy (LE) beacon array arranged in a predetermined relationship with and differentiating between different locations, and communicably connected to each of the mobile devices that is configured to resolve its proximity, from the beacon array, relative to the at least one location and signal the device proximity to the backend processor. The backend processor is configured to register the device proximity and initiate a predetermined action associated with the state of the corresponding selectable element within the clinical process directory based on the resolved device proximity.

In accordance with a fourteenth aspect of the disclosed embodiment, wherein each of the mobile devices is configured to receive communications from the backend related to the clinical process.

In accordance with a fourteenth aspect of the disclosed embodiment, wherein the predetermined action is registering the real time proximity of the mobile device relative to the location associated with the clinical task and the corresponding selectable element within the clinical process directory.

In accordance with a fourteenth aspect of the disclosed embodiment, wherein the predetermined action is selecting between sending and not sending a communication to the mobile device based on resolving the mobile device real time proximity at the location associated with the clinical task and the corresponding selectable element within the clinical process directory.

In accordance with a fourteenth aspect of the disclosed embodiment, wherein the communication is an alarm generating signal, or a signal turning off an alarm on the mobile device.

In accordance with a fourteenth aspect of the disclosed embodiment, wherein the predetermined action is escalating an alarm to another of the mobile devices based on the real time proximity of the mobile device and the other mobile device.

In accordance with a fourteenth aspect of the disclosed embodiment, wherein the beacon array is a Bluetooth® low energy (BLE) beacon array.

In accordance with a fourteenth aspect of the disclosed embodiment, wherein the backend processor is configured to manage the clinical process by changing a state of the selectable element within the clinical process directory based on the resolved device proximity.

In accordance with a fourteenth aspect of the disclosed embodiment, wherein the action is mapping proximities of the group of mobile devices.

In accordance with a fourteenth aspect of the disclosed embodiment, wherein the map defines both track and real time proximity of each of mobile device with respect to the corresponding selectable element within the clinical process directory.

In accordance with a fourteenth aspect of the disclosed embodiment, wherein the action is registering a track of each mobile device proximity and real time proximity relative to the corresponding a clinical task and its corresponding selectable element within the clinical process directory.

In accordance with a fourteenth aspect of the disclosed embodiment, wherein the processor initiates the predetermined action based on registering a change in proximity.

In accordance with a fourteenth aspect of the disclosed embodiment, wherein the processor initiates the predetermined action based on registering a change in proximity of more than one of the mobile devices.

In accordance with a fourteenth aspect of the disclosed embodiment, wherein each mobile device has a device processor resident therein configured to resolve the proximity of the device, from the beacon array, and initiate a predetermined action based on the proximity.

In accordance with a fourteenth aspect of the disclosed embodiment, wherein the state of each selectable element within the clinical process directory is presented to a third party user via an Application Programming Interface (API) module of the system backend.

A fifteenth aspect of the disclosed embodiment system for controlling a mobile device having a system backend with a backend processor configured to manage a clinical process in a predetermined region, the clinical process comprises a series of clinical tasks for care of a common patient, each clinical tasks in the series corresponding to different selectable elements within a clinical process directory so that each selectable element represents a different clinical task, at least one mobile device communicably connected via a network to the backend, and having a processor, the at least one mobile device having at least one built in function, or a functionality, related to effecting at least one of the clinical tasks of the clinical process and altering a state of the corresponding selectable element within the clinical process directory, controlled by the processor, and a low energy (LE) beacon array arranged in a predetermined relationship with and differentiating between different locations in the predetermined region, and communicably connected to the at least one mobile device. The processor of the at least one mobile device is configured to resolve, from the beacon array, the mobile device's proximity to a predetermined one of the different locations. The processor is further configured to disable the built in function or the functionality related to effecting at least one of the clinical tasks of the clinical process, and disable the ability of the at least one mobile device to alter the state of the corresponding selectable elements within the clinical process directory, based on the mobile device's proximity to the predetermined location.

In accordance with a fifteenth aspect of the disclosed embodiment, wherein the state of each selectable element within the clinical process directory is presented to a third party user via an Application Programming Interface (API) module of the system backend.

A sixteenth aspect of the disclosed embodiment system for maintaining system readiness having a system backend, a low energy beacon array having at least one beacon configured to transmit a beacon signal, a group of mobile devices, each communicably connected via a network to the system backend with a communications transceiver and each mobile device further configured to receive the beacon signal and resolve a proximity relative to a predetermined location. Each of the mobile devices further having a sleep mode and an awake mode, where the mobile device's communications transceiver is deactivated in the sleep mode and the mobile device's communication transceiver is activated in the awake mode and the mobile device is further configured to enter the sleep mode from the awake mode in a sleep mode predetermined period of time. The mobile device is configured to receive the beacon signal and, in response to the received beacon signal and based on the resolved proximity relative to a predetermined location, the mobile device is further configured to maintain activation of the awake mode.

A seventeenth aspect of the disclosed embodiment system for tracking physical assets within an enclosed facility having a system backend comprising a backend processor configured to track a physical asset location of at least one physical asset within the enclosed facility, a group of mobile devices communicably connected via a network to the system backend, a low energy (LE) beacon array arranged in a predetermined relationship with and differentiating between different physical locations within the enclosed facility, and communicably connected to each of the mobile devices that is configured to resolve its mobile device proximity to the physical locations within the enclosed facility, from the beacon array, the at least one physical asset having a low energy (LE) beacon and detectable by each of the mobile devices, where the low energy (LE) beacon associated with each of the at least one physical asset being distinct from a different low energy (LE) beacon of another of the at least one physical asset. The backend processor is configured to identify the at least one physical asset and dynamically determine its physical asset location based on the resolved mobile device proximity of the at least one mobile device.

A third aspect of the disclosed embodiment for a system for controlling process pathways. The system having a network, a system backend communicably connected with the network, the backend having a processor configured to manage a physical process that comprises a series of physical tasks, each with an associated physical location and at least one of which is different than another physical location of a different one of the physical tasks, and to manage an associated process pathway embodying the physical process, each of the different physical tasks in the series corresponding to different points along the pathway so that each point represents a different physical task and its location, a group of mobile devices communicably connected to the system backend, each of the mobile devices having a different predetermined characteristic related to effecting at least one of the physical tasks and altering a state of the corresponding pathway point, a BLE beacon array arranged in a predetermined relationship with and differentiating between different physical task locations, and communicably connected to each of the mobile devices that is configured to resolve its proximity, from the beacon array, relative to the at least one physical task location and signal the device proximity to the backend processor. The processor is configured to register the device location and map the mobile devices, wherein the map is configured to define both proximity track and a real time proximity of each mobile device with respect to the corresponding pathway point.

It should be understood that the foregoing description is only illustrative of the aspects of the disclosed embodiment. Various alternatives and modifications can be devised by those skilled in the art without departing from the aspects of the disclosed embodiment. It should also be understood that the flowcharts disclosed within are only illustrative of the aspects of the disclosed embodiment. The actions described in the flowcharts may not be performed strictly in the sequence disclosed within each flowchart. Various alternatives and modifications can be devised by those skilled in the art without departing from the aspects of the disclosed embodiment shown in the flowcharts. Accordingly, the present aspects of the disclosed embodiment are intended to embrace all such alternatives, modifications and variances.

What is claimed is:

1. A system for controlling a patient clinical process in a healthcare facility, the system comprising:
    a system backend comprising: a backend processor configured to define a patient care team associated with the patient clinical process for administering medical care to a patient within the healthcare facility, the patient clinical process comprising of a series of patient clinical tasks effected within the healthcare facility and assigned to individual care members of the patient care team, each patient clinical task associated with a physically localized patient clinical task location within the healthcare facility, each physically localized patient clinical task location comprising a physical location within the healthcare facility at which a particular patient clinical task of the series of patient clinical tasks is to be performed with respect to administering the medical care to the patient;
    a group of mobile devices communicably connected via a network to the system backend, each mobile device comprising a device processor and being fungible with another mobile device of the group of mobile devices, wherein logging into a mobile device comprises associating and configuring the mobile device of the group of mobile devices for use by a particular care member of the patient care team;
    a low energy (LE) beacon array comprising a plurality of LE beacons, each LE beacon being arranged in a predetermined physical locational relationship relative to the other LE beacons of the plurality LE beacons and differentiating between a plurality of physically localized patient clinical task locations based on the predetermined physical locational relationship, each LE beacon broadcasting a self-identifying signal, and each mobile device being configured to resolve its device physical location within a single physically localized patient clinical task location of the plurality of physically localized patient clinical task locations by at least:
        receiving one or more self-identifying signals from individual LE beacons of the plurality of LE beacons;
        determining a proximity to each of the individual LE beacons from which the mobile device received the one or more self-identifying signals based at least in part on analyzing signal strength of the one or more self-identifying signals;
        determining a particular LE beacon that is closest in proximity to the mobile device by comparing the determined proximities; and
        resolving its device physical location as being within the single physically localized patient clinical task location that is associated with the particular LE beacon;
    wherein the backend processor is further configured to dynamically enhance the patient care team and the patient clinical process by at least:
        automatically changing a login state of the mobile device of the group of mobile devices from a first login state to a second login state based at least in part on (i) a credential information of the particular care member of the patient care team and (ii) the resolved device physical location of the mobile device, wherein the system backend receives the credential information; and
        dynamically changing in real-time a first predetermined characteristic of the patient care team and a second predetermined characteristic of the patient clinical process based on the resolved device physical location of each mobile device associated with each care member of the patient care team.

2. The system of claim 1, wherein the backend processor is further configured to resolve care members of the patient care team for each patient clinical task based on the resolved device physical location of each mobile device associated with each care member of the patient care team.

3. The system of claim 2, wherein the backend processor resolves care members of the patient care team by dynamically updating a care team directory associated with each patient clinical task, the care team directory comprising one or more selectable elements, presented on each mobile device, each of the one or more selectable elements associated with each care member of the patient care team.

4. The system of claim 3, wherein the backend processor dynamically changes a state of at least one of the one or more selectable elements within the care team directory on each mobile device, the state of the at least one of the one or more selectable elements indicating availability of the associated care member of the patient care team, for each patient clinical task, based on the resolved device physical location of each mobile device associated with each care member.

5. The system of claim 4, wherein the state of the at least one of the one or more selectable elements within the care team directory is presented to a third party user via an Application Programming Interface (API) module of the system backend.

6. The system of claim 1, wherein the backend processor is further configured to dynamically route communication links between the care members and content links between the care members based on the resolved device physical location of each mobile device associated with each care member of the patient care team.

7. The system of claim 1, wherein the backend processor is further configured to dynamically route asynchronous secure messaging based on the resolved device physical location of each mobile device associated with each care member of the patient care team.

8. The system of claim 1, wherein the backend processor is further configured to dynamically route notifications and alerts associated with the patient clinical process based on the resolved device physical location of each mobile device associated with each care member of a patient care team.

9. The system of claim 8, wherein the notification and the alerts are dynamically escalated by the backend processor based on the resolved device physical location of each mobile device associated with each care member of the patient care team.

10. The system of claim 1, wherein the backend processor is further configured to filter access to at least one patient information associated with the patient clinical process based on the resolved device physical location of each mobile device associated with each care member of the patient care team.

11. The system of claim 1, wherein the backend processor is further configured to filter access to at least one clinical information associated with the patient clinical process based on the resolved physical location of each mobile device associated with each care member of the patient care team.

12. The system of claim 1, wherein the backend processor is further configured to filter access to at least one laboratory information associated with the patient care process based on the resolved device physical location of each mobile device associated with each care member of the patient care team.

13. The system of claim 1, wherein the backend processor is further configured to generate a patient care process-specific patient care team directory based on the resolved device physical location of each mobile device associated with each care member of the patient care team.

14. The system of claim 1, wherein associating and configuring the mobile device comprises at least one of: (i) causing personalized settings and data of the particular care member to be accessible on the mobile device, and (ii) enabling at least one built in function of the mobile device related to effecting at least one of the clinical tasks of the clinical process, the at least one of the clinical tasks being assigned to the particular care member.

15. A system for controlling a patient clinical process in a healthcare facility, the system comprising:
a system backend comprising: a backend processor configured to define a patient care team associated with the patient clinical process for administering medical care to a patient within the healthcare facility, the patient clinical process comprising of a series of patient clinical tasks effected within the healthcare facility and assigned to individual care members of the patient care team, each patient clinical task associated with a physically localized patient clinical task location within the healthcare facility, each physically localized patient clinical task location comprising a physical location within the healthcare facility at which a particular patient clinical task of the series of patient clinical tasks is to be performed with respect to administering medical care to the patient, the backend processor further configured to generate a care team directory for each patient clinical task, the care team directory comprising one or more selectable elements associated with one or more care members of the patient care team;
a group of mobile devices communicably connected via a network to the system backend, each mobile device comprising a device processor and being fungible with another mobile device of the group of mobile devices, wherein logging into a mobile device comprises associating and configuring the mobile device of the group of mobile devices for use by a particular care member of the patient care team, the configuring further comprising presenting the one or more selectable elements associated with the care team directory for each patient clinical task;
and a low energy (LE) beacon array comprising a plurality of LE beacons, each LE beacon being arranged in a predetermined physical locational relationship relative to the other LE beacons of the plurality of LE beacons and differentiating between a plurality of physically localized patient clinical task locations based on the predetermined physical locational relationship, each LE beacon broadcasting a self-identifying signal, and each mobile device being configured to resolve its device physical location within a single physically localized patient clinical task location of the plurality of physically localized patient clinical task locations by at least:
receiving one or more self-identifying signals from individual LE beacons of the plurality of LE beacons;
determining a proximity to each of the individual LE beacons from which the mobile device received the one or more self-identifying signals based at least in part on analyzing signal strength of the one or more self-identifying signals;
determining a particular LE beacon that is closest in proximity to the mobile device by comparing the determined proximities; and
resolving its device physical location as being within the single physically localized patient clinical task location that is associated with the particular LE beacon;
wherein the backend processor is further configured to at least:
automatically change a login state of the mobile device of the group of mobile devices from a first login state to a second login state based at least in part on (i) a credential information of the particular care member of the patient care team and (ii) the resolved device physical location of the mobile device, wherein the system backend receives the credential information;
dynamically update and enhance the care team directory for each patient clinical task by dynamically changing a first predetermined characteristic of the patient care team based on the resolved device physical location of each mobile device; and
dynamically update the patient clinical process by dynamically changing a second predetermined characteristic of the patient clinical process based on the resolved device physical location of each mobile device.

16. The system of claim 15, wherein the backend processor is further configured to dynamically update and enhance the care team directory by dynamically changing a state of at least one of the one or more selectable elements within the care team directory, the state of the at least one of the one or more selectable elements reflecting an availability of each care member, of the patient care team for each patient clinical task, based on the resolved device physical location of each mobile device associated with each care member.

17. The system of claim 15, wherein the backend processor is further configured to dynamically route communication links between the care members and content links between the care members based on the resolved device physical location of each mobile device associated with each care member of the patient care team.

18. The system of claim 15, wherein the backend processor is further configured to dynamically route asynchronous secure messaging based on the resolved device physical location of each mobile device associated with each care member of the patient care team.

19. The system of claim 15, wherein the backend processor is further configured to dynamically route notifications and alerts associated with the patient clinical process based on the resolved device physical location of each mobile device associated with each care member of a patient care team.

20. The system of claim 19, wherein the notifications and the alerts are dynamically escalated by the backend processor based on the resolved device physical location of each mobile device associated with each care member of the patient care team.

21. The system of claim 15, wherein the backend processor is further configured to filter access to at least one clinical information associated with the patient clinical process based on the resolved device physical location of each mobile device associated with each care member of the patient care team.

22. A system for controlling clinical processes, the system comprising:
a system backend having a backend processor configured to manage a clinical process for administering medical care to a common patient within a healthcare facility, the clinical process comprising a series of clinical tasks for care of the common patient and being assigned to individual care members of a patient care team, each clinical task associated with a physical location within the healthcare facility at which a particular clinical task of the series of clinical tasks is to be performed with respect to administering the medical care to the common patient, at least one associated physical location is different than another associated physical location of a different one of the clinical tasks, each of the different clinical tasks in the series corresponding to different selectable elements within a clinical process directory so that each selectable element represents a different clinical task and its physical location;
a group of mobile devices communicably connected via a network to the system backend, each of the mobile devices comprising a device processor and being fungible with another mobile device of the group of mobile devices, wherein logging into a mobile device comprises associating and configuring the mobile device of the group of mobile devices for use by a particular member of the patient care team, the configuring further comprising causing the mobile device to have a different predetermined characteristic related to effecting at least one of the clinical tasks and altering a state of the corresponding selectable element within the clinical process directory; and
a low energy (LE) beacon array comprising a plurality of LE beacons, each LE beacon being arranged in a predetermined physical locational relationship relative to the other LE beacons of the plurality LE beacons and differentiating between a plurality of physically localized patient clinical task locations based on the predetermined physical locational relationship, each LE beacon broadcasting a self-identifying signal, and the mobile device being configured to resolve its device physical location within a single physically localized patient clinical task location of the plurality of physically localized patient clinical task locations by at least:
receiving one or more self-identifying signals from individual LE beacons of the plurality of LE beacons;
determining a proximity to each of the individual LE beacons from which the mobile device received the one or more self-identifying signals based at least in part on analyzing signal strength of the one or more self-identifying signals;
determining a particular LE beacon that is closest in proximity to the mobile device by comparing the determined proximities; and
resolving its device physical location as being within the single physically localized patient clinical task location that is associated with the particular LE beacon;
wherein, upon the mobile device resolving its device physical location and signaling the resolved device physical location to the backend processor, the backend processor is further configured to register the resolved device physical location and at least:
automatically change a login state of the mobile device of the group of mobile devices from a first login state to a second login state based at least in part on (i) a credential information of the particular care member of the patient care team and (ii) the resolved device physical location of the mobile device, wherein the system backend receives the credential information; and
initiate a predetermined action associated with the state of the corresponding selectable element within the clinical process directory based on the resolved device physical location, wherein the predetermined action comprises at least one of dynamically changing a first predetermined characteristic of the patient care team or dynamically changing a second predetermined characteristic of the clinical process.

23. The system of claim 22, wherein each of the mobile devices is configured to receive communications from the system backend related to the clinical process.

24. The system of claim 22, wherein the predetermined action is registering a real time device physical location of the mobile device relative to the physical location associated with the clinical task and the corresponding selectable element within the clinical process directory.

25. The system of claim 22, wherein the predetermined action is selecting between sending and not sending a communication to the mobile device based on resolving a real time device physical location of the mobile device at a particular clinical task location associated with the particular clinical task and the corresponding selectable element within the clinical process directory.

26. The system of claim 25, wherein the communication is an alarm generating signal, or a signal turning off an alarm on the mobile device.

27. The system of claim 22, wherein the predetermined action is escalating an alarm to another of the mobile devices based on a real time device physical location of the mobile device and the another mobile device.

28. The system of claim 22, wherein the low energy beacon array is a Bluetooth™ low energy (BLE) beacon array.

29. The system of claim 22, wherein the backend processor is further configured to manage the clinical process by changing the state of the corresponding selectable element within the clinical process directory based on the resolved device physical location.

30. The system of claim 22, wherein the predetermined action is mapping device physical locations of the group of mobile devices.

31. The system of claim 30, wherein the mapping defines both a track and a real time device physical location of each mobile device with respect to the corresponding selectable element within the clinical process directory.

32. The system of claim 22, wherein the predetermined action is registering a track of the resolved device physical location and a real time device physical location of the mobile device relative to the corresponding clinical task and its corresponding selectable element within the clinical process directory.

33. The system of claim 22, wherein the backend processor initiates the predetermined action based on registering a change in the resolved device physical location.

34. The system of claim 22, wherein the backend processor initiates the predetermined action based on registering a change in a resolved device physical location of more than one of the mobile devices of the group of mobile devices.

35. The system of claim 22, wherein the device processor is configured to resolve the device physical location of the mobile device, from the LE beacon array, and initiate a different predetermined action based on the resolved device physical location.

36. The system of claim 22, wherein a state of each selectable element within the clinical process directory is presented to a third party user via an Application Programming Interface (API) module of the system backend.

37. A system for controlling a mobile device comprising:
a system backend with a backend processor configured to manage a clinical process in a predetermined region, the clinical process comprising a series of clinical tasks for administering medical care to a common patient within the predetermined region and by a patient care team, each clinical task assigned to an individual care member of the patient care team, each clinical task in the series associated with a physically localized patient clinical task location within the predetermined region at which a particular clinical task of the series of clinical tasks is to be performed with respect to administering the medical care to the common patient, and corresponding to different selectable elements within a clinical process directory so that each selectable element represents a different clinical task;
a mobile device of a group of mobile devices communicably connected via a network to the system backend, and having a device processor, the mobile device being fungible with another mobile device of the group of mobile devices, wherein logging into the mobile device comprises associating and configuring the mobile device of the group of mobile devices for use by a particular member of the patient care team, the configuring further comprising enabling at least one built in function, or a functionality, related to effecting at least one of the clinical tasks of the clinical process and altering a state of the corresponding selectable element within the clinical process directory, controlled by the device processor; and
a low energy (LE) beacon array comprising a plurality of LE beacons, each LE beacon being arranged in a predetermined physical locational relationship relative to the other LE beacons of the plurality LE beacons and differentiating between a plurality of physically localized patient clinical task locations based on the predetermined physical locational relationship, each LE beacon broadcasting a self-identifying signal, and the device processor of the mobile device being configured to resolve its device physical location within a single physically localized patient clinical task location of the plurality of physically localized patient clinical task locations by at least:
receiving one or more self-identifying signals from individual LE beacons of the plurality of LE beacons;
determining a proximity to each of the individual LE beacons from which the mobile device received the one or more self-identifying signals based at least in part on analyzing signal strength of the one or more self-identifying signals;
determining a particular LE beacon that is closest in proximity to the mobile device by comparing the determined proximities; and
resolving its device physical location as being within the single physically localized patient clinical task location that is associated with the particular LE beacon, wherein the backend processor is further configured to at least:
automatically change a login state of the mobile device from a first login state to a second login state based at least in part on (i) a credential information of the particular care member of the patient care team and (ii) the resolved device physical location of the mobile device, wherein the system backend receives the credential information;
disable or enable the at least one built in function or the functionality related to effecting at least one of the clinical tasks of the clinical process based at least in part on the login state; and
disable or enable the ability of the mobile device to alter the state of the corresponding selectable elements within the clinical process directory, based on the mobile device's resolved device physical location within the single physically localized patient clinical task location.

38. The system of claim 37, wherein a state of each selectable element within the clinical process directory is presented to a third party user via an Application Programming Interface (API) module of the system backend.

\* \* \* \* \*